US008986983B2

(12) United States Patent
Montagu et al.

(10) Patent No.: US 8,986,983 B2
(45) Date of Patent: Mar. 24, 2015

(54) ASSAYS BASED ON LIQUID FLOW OVER ARRAYS

(75) Inventors: Jean I. Montagu, Brookline, MA (US); Herman Deweerd, Bedford, MA (US); Roger Dowd, Natick, MA (US); Natalia Rodionova, Waltham, MA (US); Peter Maimonis, Westwood, MA (US); Nathan Tyburczy, Arlington, MA (US)

(73) Assignee: Courtagen Life Sciences, Inc., Woburn, MA (US)

( * ) Notice: Subject to any disclaimer, the term of this patent is extended or adjusted under 35 U.S.C. 154(b) by 287 days.

(21) Appl. No.: 12/876,883

(22) Filed: Sep. 7, 2010

(65) Prior Publication Data

US 2011/0319279 A1 Dec. 29, 2011

Related U.S. Application Data

(62) Division of application No. 11/262,115, filed on Oct. 27, 2005, now abandoned.

(60) Provisional application No. 60/688,269, filed on Jun. 6, 2005.

(51) Int. Cl.
*C12M 1/34* (2006.01)
*B01L 3/00* (2006.01)
(Continued)

(52) U.S. Cl.
CPC ..... *B01L 3/502746* (2013.01); *B01L 3/502715* (2013.01); *B01L 3/502723* (2013.01);
(Continued)

(58) Field of Classification Search
USPC ............... 422/504, 505; 435/288.5; 436/52
See application file for complete search history.

(56) References Cited

U.S. PATENT DOCUMENTS 4,643,713 A 2/1987 Viitala
4,695,431 A 9/1987 Farrell
(Continued)

FOREIGN PATENT DOCUMENTS

DE 197 36-641 A1 3/1999
WO WO 2004/009840 A1 1/2004
(Continued)

OTHER PUBLICATIONS

Notification of Transmittal of the International Search Report and the Written Opinion of the International Searching Authority for PCT/US2005/039020; date of mailing Mar. 28, 2006.
(Continued)

*Primary Examiner* — Melanie Y Brown
*Assistant Examiner* — Erik B Crawford
(74) *Attorney, Agent, or Firm* — Hamilton, Brook, Smith & Reynolds, P.C.

(57) ABSTRACT

Cassette (50) performs assays, e.g. multiplexed protein biomarker assays. Wide, bubble-free, slow flows are produced from liquids stored on cassette (50), flowing over wide array (20) of ligand receptors on a capture surface. Flows of Reynolds Number less than about 1, preferably $1 \times 10^{-1}$ to $5 \times 10^{-3}$, are heated in region (34) preceding and including bubble removal system (128). Analyte is introduced through compressed septum (32). External actuations of displacement pumps (30, 37) and valves (137 A, B, and C) produce flows in response to flow-front optical sensors (150, 152). Elastic sheet provides pump and valve diaphragms and resilient expansion of mixing volume (131). Break-away cover portions are pistons. Heating is by conduction through cassette from external contact heater. Planar cassette body, when tilted from horizontal, enables upward flow from pumped storage (134, 135) to reaction (133) to waste (139), with buoyancy bubble removal before reaction. Reading of fluorescence is by external reader, employing calibration, control and reference features on capture surface. Extensive set of calibration features of differing intensities enables self-calibration.

77 Claims, 28 Drawing Sheets

(51) Int. Cl.
  *B01L 7/00* (2006.01)
  *B01L 9/00* (2006.01)

(52) U.S. Cl.
  CPC ....... *B01L3/50273* (2013.01); *B01L 3/502738*
    (2013.01); *B01L 7/00* (2013.01); *B01L 9/527*
    (2013.01); *B01L 2200/027* (2013.01); *B01L*
    *2200/0684* (2013.01); *B01L 2200/16* (2013.01);
    *B01L 2300/0636* (2013.01); *B01L 2300/0654*
    (2013.01); *B01L 2300/0672* (2013.01); *B01L*
    *2300/0816* (2013.01); *B01L 2300/0867*
    (2013.01); *B01L 2300/0877* (2013.01); *B01L*
    *2300/1827* (2013.01); *B01L 2400/0481*
    (2013.01); *B01L 2400/0487* (2013.01); *B01L*
    *2400/0655* (2013.01); *B01L 2400/0683*
    (2013.01); *B01L 2400/0688* (2013.01)
  USPC ........... 435/288.5; 422/504; 422/505; 436/52

(56) References Cited

U.S. PATENT DOCUMENTS

| | | | |
|---|---|---|---|
| 4,734,269 A | 3/1988 | Clarke et al. | |
| 4,756,884 A | 7/1988 | Hillman et al. | |
| 5,028,535 A | 7/1991 | Buechler et al. | |
| 5,053,197 A | 10/1991 | Bowen | |
| 5,089,391 A | 2/1992 | Buechler et al. | |
| 5,096,669 A | 3/1992 | Lauks et al. | |
| 5,143,854 A | 9/1992 | Pirrung et al. | |
| 5,160,702 A | 11/1992 | Kopf-Sill et al. | |
| 5,230,866 A | 7/1993 | Shartle et al. | |
| 5,478,751 A | 12/1995 | Oosta et al. | |
| 5,554,339 A | 9/1996 | Cozzette et al. | |
| 5,746,184 A | 5/1998 | Ekstam | |
| 5,798,215 A | 8/1998 | Cathey et al. | |
| 5,821,399 A | 10/1998 | Zelin | |
| 5,834,319 A | 11/1998 | Ekins | |
| 5,863,801 A | 1/1999 | Southgate et al. | |
| 5,912,134 A | 6/1999 | Shartle | |
| 5,945,334 A * | 8/1999 | Besemer et al. | 435/287.2 |
| 6,143,248 A | 11/2000 | Kellogg et al. | |
| 6,143,576 A | 11/2000 | Buechler | |
| 6,168,948 B1 * | 1/2001 | Anderson et al. | 435/287.2 |
| 6,184,029 B1 | 2/2001 | Wilding et al. | |
| 6,192,168 B1 | 2/2001 | Feldstein et al. | |
| 6,197,599 B1 | 3/2001 | Chin et al. | |
| 6,207,369 B1 | 3/2001 | Wohlstadter et al. | |
| 6,215,894 B1 | 4/2001 | Zeleny et al. | |
| 6,221,677 B1 | 4/2001 | Wu et al. | |
| 6,274,872 B1 | 8/2001 | Katerkamp | |
| 6,296,020 B1 | 10/2001 | McNeely et al. | |
| 6,391,265 B1 | 5/2002 | Buechler et al. | |
| 6,391,541 B1 | 5/2002 | Petersen et al. | |
| 6,440,748 B1 | 8/2002 | Katerkamp et al. | |
| 6,472,671 B1 | 10/2002 | Montagu | |
| 6,488,827 B1 | 12/2002 | Shartle | |
| 6,508,859 B1 | 1/2003 | Zia et al. | |
| 6,537,505 B1 | 3/2003 | LaBudde et al. | |
| 6,576,478 B1 | 6/2003 | Wagner et al. | |
| 6,589,779 B1 | 7/2003 | McDevitt et al. | |
| 6,591,852 B1 | 7/2003 | McNeely et al. | |
| 6,602,702 B1 | 8/2003 | McDevitt et al. | |
| 6,634,741 B2 | 10/2003 | Kataoka et al. | |
| 6,637,463 B1 | 10/2003 | Lei et al. | |
| 6,663,833 B1 | 12/2003 | Stave et al. | |
| 6,673,533 B1 | 1/2004 | Wohlstadter et al. | |
| 6,680,206 B1 | 1/2004 | McDevitt et al. | |
| 6,682,186 B2 | 1/2004 | Smith et al. | |
| 6,686,208 B2 | 2/2004 | Meusel et al. | |
| 6,692,696 B1 | 2/2004 | Alberte | |
| 6,713,298 B2 | 3/2004 | McDevitt et al. | |
| 6,759,009 B2 | 7/2004 | Law | |
| 6,767,194 B2 | 7/2004 | Jeon et al. | |
| 6,767,510 B1 | 7/2004 | Buechler | |
| 6,767,706 B2 | 7/2004 | Quake et al. | |
| 6,767,733 B1 | 7/2004 | Green | |
| 6,793,753 B2 | 9/2004 | Unger et al. | |
| 6,843,281 B1 | 1/2005 | Barth et al. | |
| 6,861,251 B2 | 3/2005 | Green | |
| 6,877,528 B2 | 4/2005 | Gilbert et al. | |
| 6,893,879 B2 | 5/2005 | Petersen et al. | |
| 6,908,770 B1 | 6/2005 | McDevitt et al. | |
| 6,949,377 B2 | 9/2005 | Ho | |
| 7,022,157 B2 | 4/2006 | Tsai | |
| 2002/0003001 A1 | 1/2002 | Weigl et al. | |
| 2002/0019018 A1 * | 2/2002 | Christopherson et al. | 435/7.23 |
| 2002/0039280 A1 | 4/2002 | O'Connor et al. | |
| 2002/0045272 A1 | 4/2002 | McDevitt et al. | |
| 2002/0086309 A1 | 7/2002 | Benn et al. | |
| 2002/0102613 A1 | 8/2002 | Hoogenboom | |
| 2002/0127736 A1 | 9/2002 | Chou et al. | |
| 2002/0182241 A1 | 12/2002 | Borenstein et al. | |
| 2002/0197622 A1 | 12/2002 | McDevitt et al. | |
| 2003/0020910 A1 * | 1/2003 | Peterson et al. | 356/338 |
| 2003/0032199 A1 | 2/2003 | Meusel et al. | |
| 2003/0096310 A1 | 5/2003 | Hansen et al. | |
| 2003/0124589 A1 * | 7/2003 | Piper | 435/6 |
| 2003/0156992 A1 | 8/2003 | Anderson et al. | |
| 2003/0157503 A1 | 8/2003 | McGarry et al. | |
| 2003/0162283 A1 | 8/2003 | Kuno et al. | |
| 2003/0164296 A1 | 9/2003 | Squires et al. | |
| 2003/0170881 A1 | 9/2003 | Davies et al. | |
| 2003/0228637 A1 | 12/2003 | Wang | |
| 2004/0035792 A1 | 2/2004 | Rauch et al. | |
| 2004/0063217 A1 | 4/2004 | Webster et al. | |
| 2004/0163970 A1 | 8/2004 | Sin et al. | |
| 2004/0189311 A1 | 9/2004 | Glezer et al. | |
| 2004/0228734 A1 | 11/2004 | Jeon et al. | |
| 2004/0228769 A1 | 11/2004 | Taylor et al. | |
| 2004/0258571 A1 | 12/2004 | Lee et al. | |
| 2004/0262223 A1 | 12/2004 | Strook et al. | |
| 2005/0000364 A1 | 1/2005 | Kraemer et al. | |
| 2005/0009101 A1 | 1/2005 | Blackburn | |
| 2005/0019902 A1 | 1/2005 | Mathies et al. | |
| 2005/0022895 A1 | 2/2005 | Barth et al. | |
| 2005/0052502 A1 | 3/2005 | Chung et al. | |
| 2005/0066812 A1 | 3/2005 | Vesper et al. | |
| 2005/0089863 A1 * | 4/2005 | Karlsen et al. | 435/6 |
| 2006/0019319 A1 | 1/2006 | Billadeau et al. | |
| 2006/0257992 A1 | 11/2006 | McDevitt et al. | |
| 2006/0275852 A1 | 12/2006 | Montagu et al. | |
| 2008/0014114 A1 | 1/2008 | Van Atta et al. | |
| 2011/0207621 A1 | 8/2011 | Montagu et al. | |
| 2011/0208205 A1 * | 8/2011 | Thor et al. | 606/127 |
| 2012/0132527 A1 * | 5/2012 | Kayyem | 204/409 |

FOREIGN PATENT DOCUMENTS

| | | |
|---|---|---|
| WO | WO 2004/018632 A2 | 3/2004 |
| WO | WO 2004/059299 A1 | 7/2004 |
| WO | WO 2004/061418 A2 | 7/2004 |
| WO | WO 2004061418 A2 * | 7/2004 |
| WO | WO 2005/085855 A2 | 9/2005 |
| WO | WO 2006/013266 A1 | 2/2006 |
| WO | WO 2009/105711 A1 | 8/2009 |

OTHER PUBLICATIONS

Boguskavsky, "Biomarkers as Checkpoints", downloaded Sep. 2004, URL: www.dddmag.com.

Brody, J.P., et al., "Biotechnology at Low Reynolds Numbers", *Biophysical Journal*, 17: 3430-3441 (1996).

Golden, J.P., et al., "A Portable Array Biosensor for Food Safety", *Proc. of SPIE*, 5587: 241-244 (2004).

Golden, J.P., et al., "Array Biosensor: Recent Developments", *SPIE Conference on Advances In Fluorescence Sensing Technology IV*, 3602: 132-138 (1999).

Groisman, A., et al., "Microfluidic Memory and Control Devices", *Science*, 300: 955-958 (2003).

i-STAT, Product info-Cartridges, retrieved on line Mar. 7, 2003, URL: http://www.i-stat.com/products/cartridges.asp.

(56) References Cited

OTHER PUBLICATIONS

Kamholz, A.E., et al., "Quantitative Analysis of Molecular Interaction in a Microfluidic Channell: The T-Sensor", *Anal. Chem.,* 71: 5340-5347 (1999).

Kim, E. and Whitesides, G.M., "Imbibition and Flow of Wetting Liquids in None rcular Capillaries", *J. Phys. Chem.,* B 101: 855-863 (1997).

Ko, J.S., et al., "A Polymer-Based Microfluidic Device for Immunosensing Biochip", *Lab Chip,* 3: 106-113 (2003).

Martynova, L., et al., "Fabrication of Plastic Microfluid Channels by Imprinting Methods", *Anal. Chem.,* 69: 4783-4789 (1997).

Noerholm, M., et al., "Polymer Microfluidic Chip for Online Monitoring of Microarray Hybridizations", *Lab Chip,* 4: 28-37 (2004).

Unger, M.A., et al., "Monolithic Microfabricated Valves and Pumps by Multilayer Soft Lithography", *Science,* 288: 113-116 (2000).

Woias, P., et al., "Micropumps—Summarizing the First Two Decades", *Proc. of SPIE,* 4560: 39-52 (2001).

Zeng, J., et al., "Design Analyses of Capillary Burst Valve in Centrifugal Microfluidics", Technical Proceedings of Micro Total Analysis Systems, Micro TAS, Enschede, The Netherlands, pp. 493-496 (2000).

Zeng, J., et al., "MEMS-18A: Numerical Approaches to Microfluidic Device Development, Fluidic Capacitance Model of Capillary-Driven Stop Valves", $5^{th}$ Micro-Fluidics Symposium IMECE, pp. 1-6, (2000).

Notification Concerning Transmittal of International Preliminary Report on Patentability for PCT/US2005/039020, "Assays Based on Liquid Flow Over Arrays"; date of mailing Dec. 21, 2007.

Notification of Transmittal of the International Search Report and the Written Opinion of the International Searching Authority for PCT/US2009/034777, "Assay Based on Liquid Flow Over Arrays"; date of mailing Jun. 12, 2009.

Notification Concerning Transmittal of International Preliminary Report on Patentability for PCT/US2009/034777, "Assay Based on Liquid Flow Over Arrays"; date of mailing Sep. 2, 2010.

\* cited by examiner

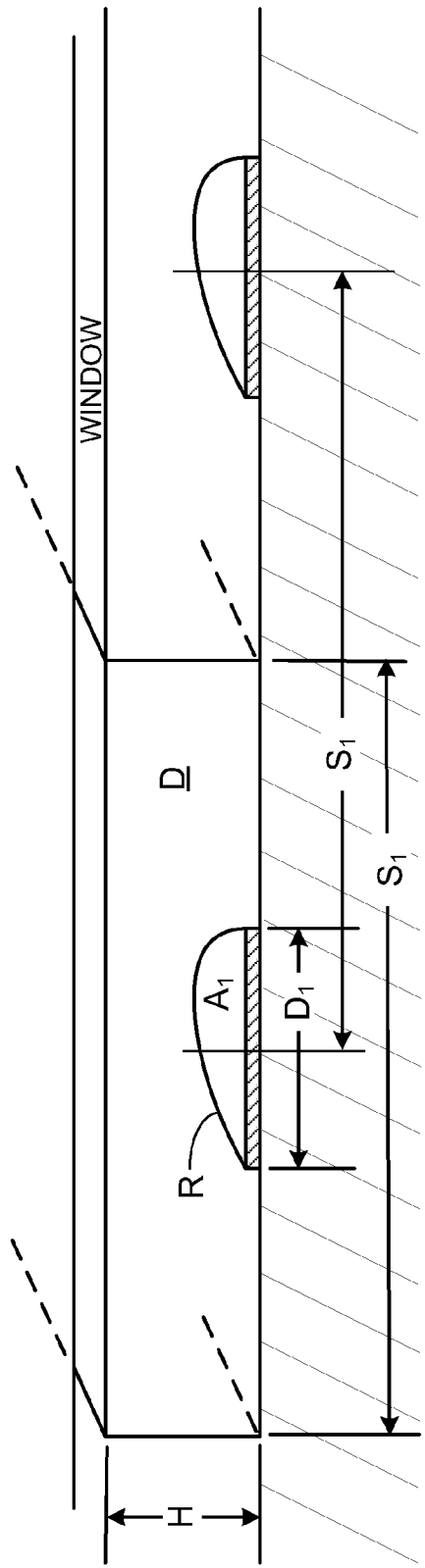
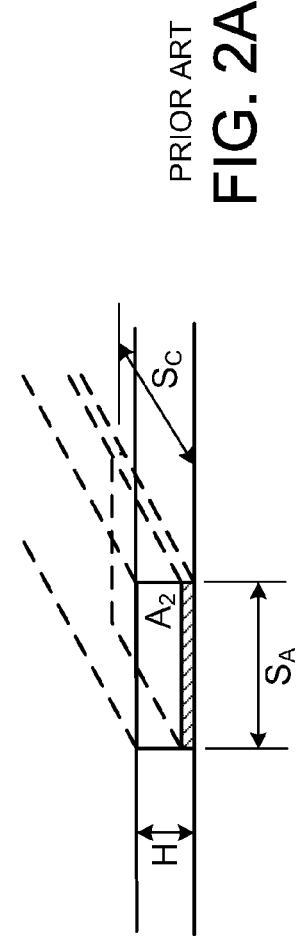
FIG. 1A
FIG. 2A
PRIOR ART

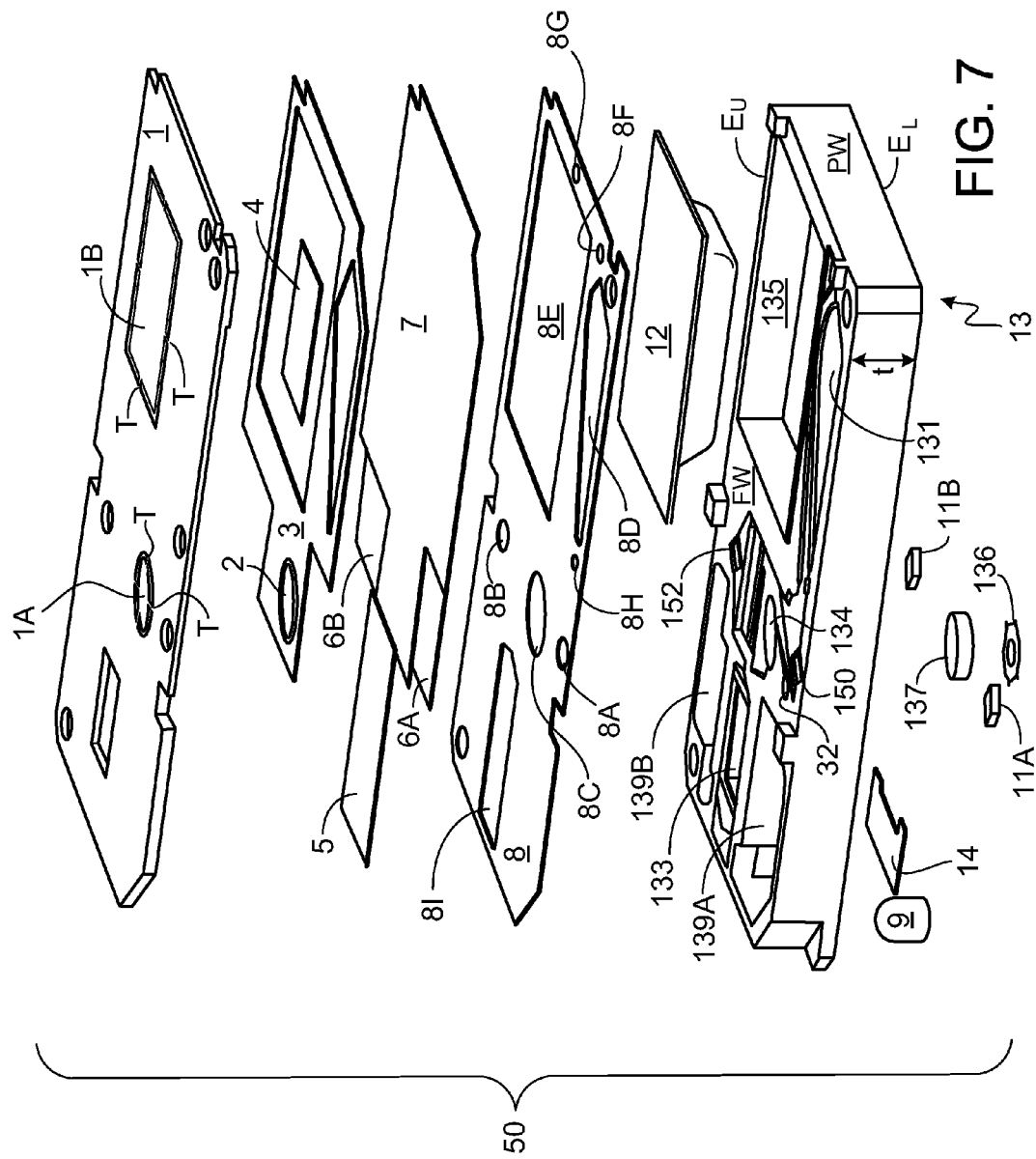

A = Microscope / viewing opening over biochip
B = Plunger of reagent pump
C = bar code scanner opening
D = Plunger of analyte pump
E = Opto-sensor opening
F = Valve stem
G = Alignment pins

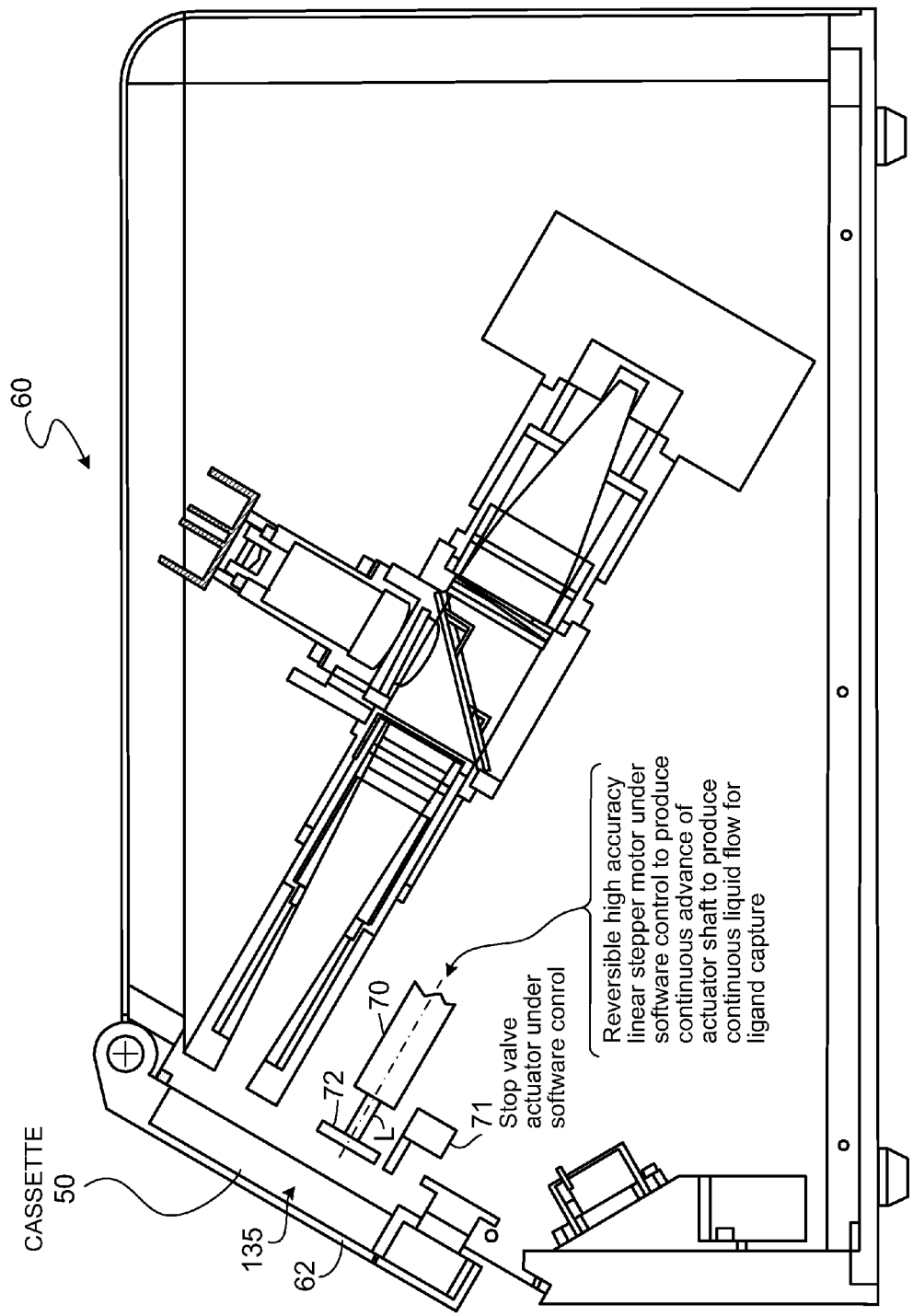

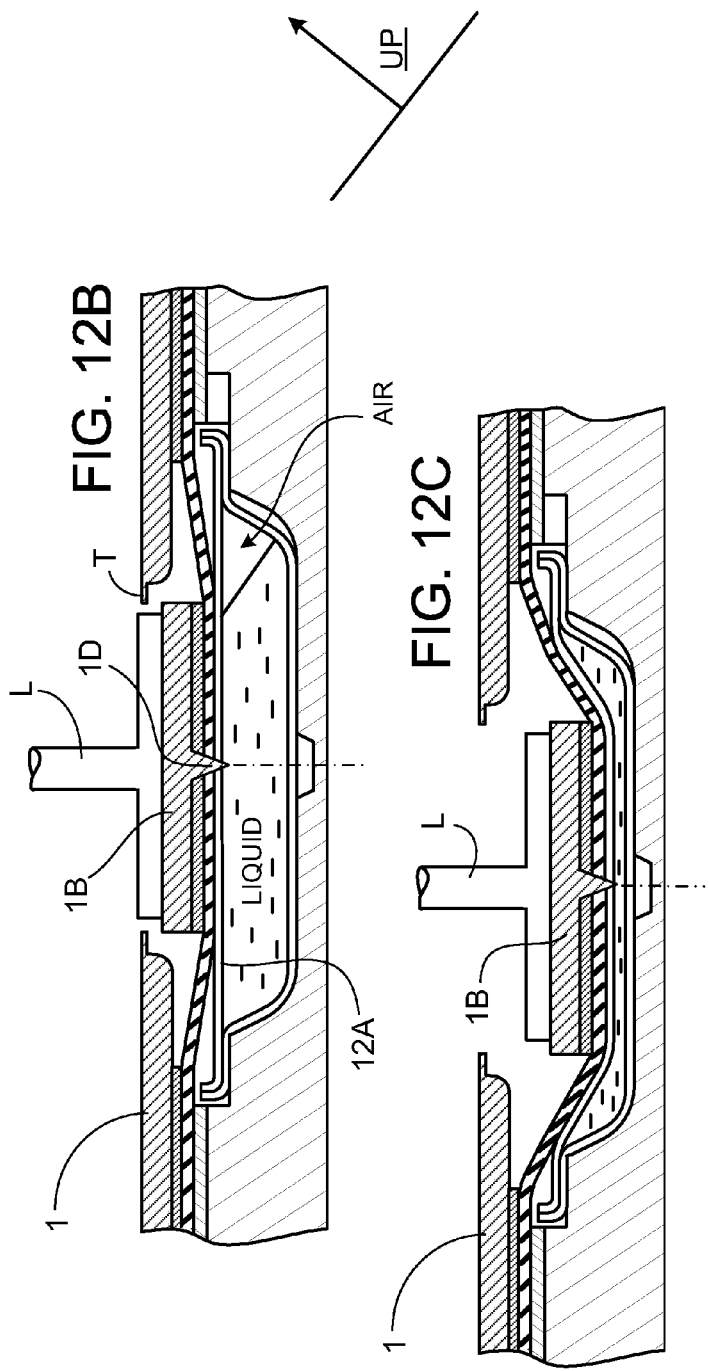

Analyte 1    O O O O O O O O O      O O O O O O O O O O  Analyte 2
Calibration 1A   O O O O O O O O O      O O O O O O O O O  Calibration 2A
Calibration 1B  O O O O O O O O O O    O O O O O O O O O O Calibration 2B
Calibration 1C   O O O O O O O O O      O O O O O O O O O  Calibration 2C
Calibration 1D  O O O O O O O O O O    O O O O O O O O O O Calibration 2D
Calibration 1F   O O O O O O O O O      O O O O O O O O O  Calibration 2F
Calibration 1G  O O O O O O O O O O    O O O O O O O O O O Calibration 2G Analyte 3    O O O O O O O O O      O O O O O O O O O O  Analyte 4
Calibration 3A   O O O O O O O O O      O O O O O O O O O  Calibration 4A
Calibration 3B  O O O O O O O O O O    O O O O O O O O O O Calibration 4B
Calibration 3C   O O O O O O O O O      O O O O O O O O O  Calibration 4C
Calibration 3D  O O O O O O O O O O    O O O O O O O O O O Calibration 4D
Calibration 3E   O O O O O O O O O      O O O O O O O O O  Calibration 4E
Calibration 3F  O O O O O O O O O O    O O O O O O O O O O Calibration 4F Analyte 5    O O O O O O O O O      O O O O O O O O O O  Analyte 6
Calibration 5A   O O O O O O O O O      O O O O O O O O O  Calibration 6A
Calibration 5B  O O O O O O O O O O    O O O O O O O O O O Calibration 6B
Calibration 5C   O O O O O O O O O      O O O O O O O O O  Calibration 6C
Calibration 5D  O O O O O O O O O O    O O O O O O O O O O Calibration 6D
Calibration 5E   O O O O O O O O O      O O O O O O O O O  Calibration 6E
Calibration 5F  O O O O O O O O O O    O O O O O O O O O O Calibration 6F Analyte 7    O O O O O O O O O      O O O O O O O O O O  Analyte 8
Calibration 7A   O O O O O O O O O      O O O O O O O O O  Calibration 8A
Calibration 7B  O O O O O O O O O O    O O O O O O O O O O Calibration 8B
Calibration 7C   O O O O O O O O O      O O O O O O O O O  Calibration 8C
Calibration 7D  O O O O O O O O O O    O O O O O O O O O O Calibration 8D
Calibration 7E   O O O O O O O O O      O O O O O O O O O  Calibration 8E
Calibration 7F  O O O O O O O O O O    O O O O O O O O O O Calibration 8F Control A    O O O O O O O O O      O O O O O O O O O  Control B

Analyte 1   O O O O O O O O O      O O O O O O O O O O  Analyte 2
Reference 1A  o o o o o o o o o      o o o o o o o o o  Reference 2A
Reference 1B  o o o o o o o o o o    o o o o o o o o o o  Reference 2B Analyte 3   O O O O O O O O O      O O O O O O O O O  Analyte 4
Reference 3A  o o o o o o o o o      o o o o o o o o  Reference 4A
Reference 3B  o o o o o o o o o o    o o o o o o o o o o  Reference 4B Analyte 5   O O O O O O O O O      O O O O O O O O O  Analyte 6
Reference 5A  o o o o o o o o o      o o o o o o o o o  Reference 6A
Reference 5B  o o o o o o o o o o    o o o o o o o o o o  Reference 6B Analyte 7   O O O O O O O O O      O O O O O O O O O  Analyte 8
Reference 7A  o o o o o o o o o      o o o o o o o o o  Reference 8A
Reference 7B  o o o o o o o o o o    o o o o o o o o o o  Reference 8B Analyte 9   O O O O O O O O O      O O O O O O O O O  Analyte 10
Reference 9A  o o o o o o o o o      o o o o o o o o o  Reference 10A
Reference 9B  o o o o o o o o o o    o o o o o o o o o o  Reference 10B Analyte 11  O O O O O O O O O      O O O O O O O O O  Analyte 12
Reference 11A  o o o o o o o o o      o o o o o o o o o  Reference 12A
Reference 11B  o o o o o o o o o o    o o o o o o o o o o  Reference 12B Analyte 13  O O O O O O O O O      O O O O O O O O O  Analyte 14
Reference 13A  o o o o o o o o o      o o o o o o o o o  Reference 14A
Reference 13B  o o o o o o o o o o    o o o o o o o o o o  Reference 14B Analyte 15  O O O O O O O O O      O O O O O O O O O  Analyte 16
Reference 15A  o o o o o o o o o      o o o o o o o o o  Reference 16A
Reference 15B  o o o o o o o o o o    o o o o o o o o o o  Reference 16B

FIG. 16B

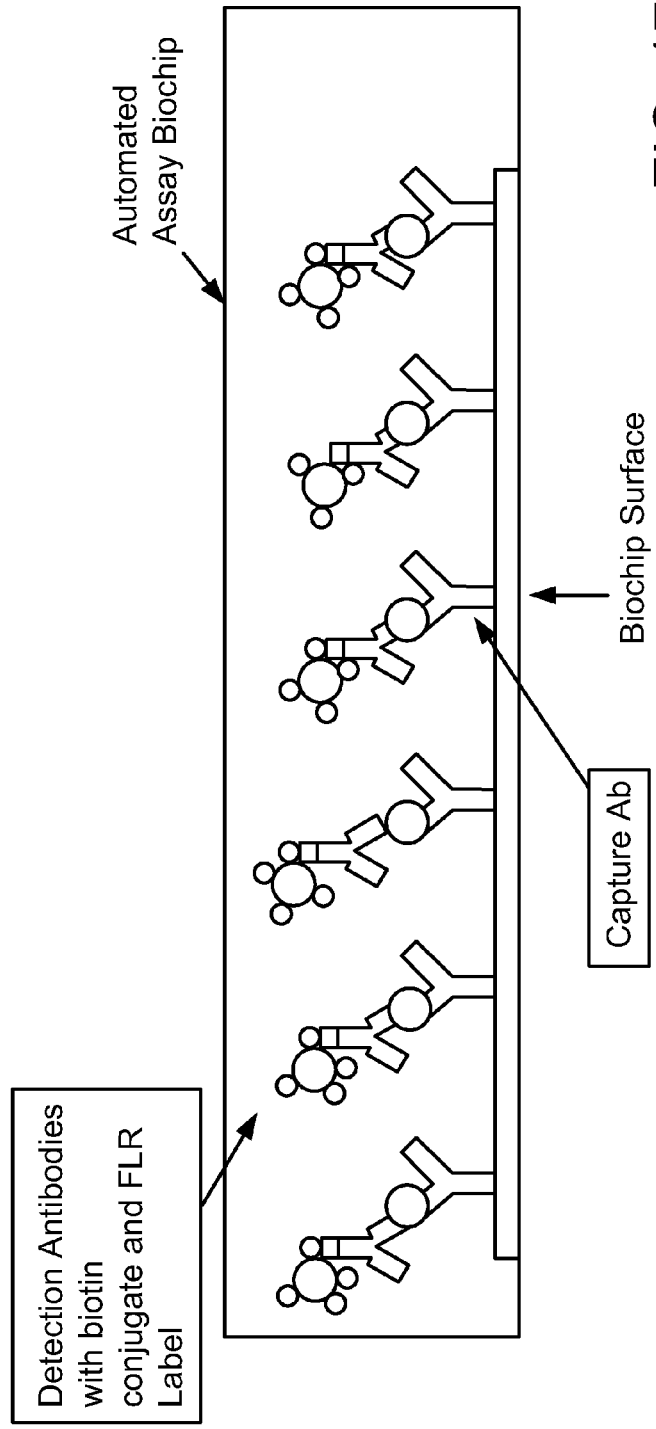

ASSAYS BASED ON LIQUID FLOW OVER ARRAYS

CROSS-REFERENCE TO RELATED APPLICATION

This application is a divisional of U.S. Ser. No. 11/262,115, filed Oct. 27, 2005, which claims the benefit under 35 U.S.C. §119(e)(1) of U.S. provisional application Ser. No. 60/688,269, filed Jun. 6, 2005, both of which are incorporated by reference herein in their entireties.

FIELD OF INVENTION

The field of invention relates to solid phase assays for the detection of analytes in liquid samples.

BACKGROUND

Ligand receptor-ligand assays on solid surfaces, such as sandwich assays, have been a standard tool in chemical and biological research and in diagnostics for many decades. For instance, Enzyme-Linked Immunoabsorbent Assays (ELISA) have been standard for quantitative analysis of protein in blood and other body fluids. Assay results have often been read by quantitative measurement of fluorescence from tags associated with ligand receptor-ligand complexes on the solid surface.

In the recent decade there has been a strong effort to perform multiple ligand receptor-ligand assays simultaneously within a small geometry, in order to reduce reagents, labor and sample sizes. In the context of genetic research and elsewhere, especially where qualitative results are all that are required, microarray technology employing spotted arrays within portable cassettes has been adopted for the assays.

However, significant obstacles have confronted development of miniaturized quantitative assay formats that are both highly sensitive and highly reproducible, for which there is great need. The obstacles have been even greater when further desired features are sought, such as simplicity, rapidity, economy and broad range applicability.

In particular, in the area of protein analytes, significant obstacles have confronted development of miniaturized, multiplexed immunoassays that enable direct comparison to or substitution for the results of standard ELISA of analytes in body fluids, especially, blood. For qualification of drugs for human use and for medical diagnostics, such assays are required to be very precise, preferably with a coefficient of variation (CV) less than 10. (The coefficient of variation (CV), defined as the percent ratio between the standard deviation of a set of values from repeated testing of a given sample and the mean of those values, provides an estimate of the degree of variability among those values. The lower the CV, the more precise the assay and the more confidence one has in the results.)

Without attempting to be exhaustive in listing the obstacles to the development of precise miniaturized assays, a few examples will be mentioned.

Some workers in the field have suggested that conditions of equilibrium are prerequisite for achieving high sensitivity and low coefficient of variation in an assay. But, use of very small samples is particularly difficult in an equilibrium assay, because such an assay is generally volume-dependent. Accuracy and repeatability depend on controlling the accuracy of the sample volume. Unfortunately, when the sample volume is very small, an assay that depends on maintaining an accurate sample volume is prone to variation from assay to assay. Even if the sample size is controlled by an automated metering system, there is such variation.

Another proposal has been to detect analytes by a method based on an ambient analyte theory that requires particularly small spots of ligand receptors. This size requirement challenges the capabilities of conventional instruments used in producing spotted microarrays. Furthermore, very small spots present the difficulty, when reading the results, of lack of sufficient resolution and of sufficiently low background noise. Furthermore, such assays take long to perform, typically well over one hour.

Various approaches to the design of miniaturized multiplexed assays have employed microfluidic technology, with flow channels and reaction chambers having flow cross-section typically less than 0.02 mm$^2$. Numerous uncontrolled phenomena can influence the results in such a system. Liquid temperature change, as well as atmospheric pressure change, and localized liquid pressure change as liquids encounter sharp edges, space discontinuities, or variation of surface properties such as surface roughness or different surface tension properties, can all produce gas micro-bubbles that, we have realized, have heretofore not been adequately recognized or taken into account in the context of assay cassettes.

Other approaches, such as those employing capillary or osmotic forces for moving liquids through an assay, have been highly sensitive to the characteristics of the particular fluids and passage materials involved, and have required custom development for narrow groups of analytes. With some such approaches, a requirement of intersections with discrete lanes of migrating liquid has limited the amount of data obtainable in a desirable geometry and has prevented achieving desired coefficient of variation in quantitative results.

Still other approaches have suffered from complexity, high cost, requirement of skilled operators, or lack of suitability for implementation in disposable cassettes.

In general, the ability to measure analyte concentrations in miniaturized, multiplex assays suffers from what has appeared to be necessary tradeoffs between sensitivity, repeatability, performance, cost and ability to compare results with standardized assays.

Developers of biological assays have made various attempts to escape some of the constraints associated with conventional assay techniques. An example is by reading an assay by electrical measurement. Effort has been expended in the development of chemical sensors that can measure the presence or the concentration of chemical species in blood or other biological fluids in this manner. One of the drawbacks of such methods is the inability to enable direct comparison to standard ELISA results. Other drawbacks are the requirement of accurately controlled liquid volume, and the difficulty of performing the assay on multiple analytes simultaneously. Besides, there is the drawback of having to make electrical connection with an assay cassette; over time, the electrical terminals may introduce inaccuracies or require maintenance. Designs of this category, as well, may suffer from uncontrolled phenomena mentioned above, to which aspects of present invention offer solution.

In view of the limitations and drawbacks of prior approaches, there is considerable need for improved approaches to the problems of miniaturized quantitative assays using arrays on solid surfaces, both with respect to assays that employ ligand receptor-ligand systems, very generally, and in particular, with respect to immunoassays, especially immunoassays for protein in body fluids such as blood.

There is special need for miniaturized assays that can be analyzed using fluorescent detection and are otherwise comparable to standard ELISA results. There is particular need for sensitive, precise multiplex assays to enable simultaneous evaluation of multiple markers that may indicate disease, the effectiveness of a drug, toxic reactions to a drug, or suitability of subjects as candidates for a drug or drug study.

There is particular need for an assay technique (or "platform") for protein biomarkers which, above all, is robust. An assay technique is needed that produces highly credible results with low coefficients of variation, is immune to interferences, and performs its function with sufficient margins that it is useful over a wide range of analytes, levels of dilution, and starting conditions. It is especially desirable that the technique also be sensitive, have significant throughput, be capable of conducting multiple assays at once and employ equipment which is easy to use. It would be beneficial, as well, for such a technique to enable simple design of particular assays and to require little sample or reagent and little handling of the sample.

SUMMARY OF INVENTION

According to one aspect of invention, an assay cassette is provided which comprises a capture surface that carries an array of spaced-apart regions of ligand receptors, and a liquid passage system constructed to direct over the array a slow flow of assay-supporting liquids having Reynolds numbers less than about 1, preferably, between about $1 \times 10^{-1}$ and $5 \times 10^{-3}$, the liquids including a ligand-containing liquid, the cassette including a gas bubble removal system to which the liquids are exposed, the gas bubble removal system constructed and arranged to remove gas micro-bubbles from the liquids prior to exposure of the liquids to the array.

According to another aspect of invention, the assay cassette as just described further incorporates heat transfer surfaces to which flows of the liquids are exposed for heating the liquids prior to exposure of the liquids to the gas bubble removal system, whereby gas micro-bubbles produced in the liquids by heat delivered via the heat transfer surfaces of the cassette can be removed before the liquids are exposed to the array. For instance, the cassette may be configured to receive heat from a heater member of an external device (e.g., the device constructed to operate the cassette), the cassette constructed and arranged to enable heat to flow through substance of the cassette to the heat transfer surfaces, thence to the liquid.

According to another aspect of invention, the assay cassette, in either of the arrangements just described, also includes a site for storage of an agent useful in the assay, the cassette constructed to enable combining a liquid with the agent to produce an assay-supporting liquid, and, respectively, to enable flow of the assay-supporting liquid through the liquid passage system, or through the passage system with exposure to a heat transfer surface, the cassette constructed to enable exposure of the assay-supporting liquid to the gas bubble removal system prior to reaching the array, whereby gas micro-bubbles previously produced in the liquid can be removed before the assay-supporting liquid is directed over the array. Preferably, the cassette separately stores a liquid and a desiccated agent, which can be combined to solubilize (or otherwise liquefy) the agent. Alternatively, the cassette may store a liquid agent in concentrated form which can be diluted by a stored buffer liquid.

It is recognized that a bubble removal system incorporated in such cassettes, preceding the capture surface, enables the liquid flow over the capture surface to be free of detrimental gas micro-bubbles that could otherwise attach to and effectively obscure a region of ligand receptors from the analyte or agent in the liquid. In particular, it is realized that harmful gas micro-bubbles may occur in a liquid merely by the act of bringing the liquid up to assay temperature, owing to the decrease in solubility of dissolved gases in liquids as the temperature of the liquids rises. Likewise, it is realized that agent-combining action and other activities in the cassette may produce gas micro-bubbles that impair the interaction of the analyte-containing liquid with the capture regions.

The gas bubble removal system on the cassette thus can minimize the consequences of bubble-producing effects of critical steps performed on liquid in the cassette, as well as of uncontrolled phenomena such as atmospheric pressure changes and localized liquid pressure changes as liquids within the cassette encounter either microscopic sharp edges, space discontinuities, or variation of surface properties such as surface roughness or different surface tension properties in the fluidic system of the cassette. Gas micro-bubbles produced by fluid displacement pumps and actuation of displacement valves of a cassette can be removed prior to the liquid reaching the capture surface of a reaction chamber, and therefore, simple designs of mechanical components can be employed.

The system for removing gas bubbles from liquids within cassette devices may avoid denaturing of analytes reagents as well as prevent micro-bubbles from interfering with binding.

Various kinds of gas bubble removal systems may be employed. As another aspect of invention, however, advantages are found in providing a passive gas bubble removal system based on the principle of buoyancy. Such a system is made possible in a cassette design by establishing the orientation of the cassette at a predetermined angle to horizontal during performance of the assay. Buoyancy forces bubbles of gas out of the liquid within the cassette and into a trap of suitable dimensions. This passive process is thus able to separate and capture detrimental gas bubbles present within a fixed volume of one or many liquids on the cassette device during liquid transport within the device. Gas bubbles can be extracted from a laminar flow at extremely low Reynolds number ($N_{Re}$), such as $N_{Re}$ less than about 1. A selected duration in the bubble escape region, e.g. between about one and five seconds, can assure removal of detrimental bubbles. Such a device can be used to perform biological assays, such as sandwich immunoassays, with low CV, preferably a CV of less than 10%.

In the context of these aspects of invention, it is recognized that the slow flow of liquids, at Reynolds numbers $N_{Re}$ of less than about 1, preferably between about $1 \times 10^{-1}$ and $5 \times 10^{-3}$, enables flow velocity and reaction chamber dimensions to have variation within reasonable tolerances, and the liquid and analyte to be of a wide selection, with negligible effect on the sensitivity and coefficient of variation of the assay. At such low Reynolds numbers, diffusion is the principal mechanism by which uniformity of distribution of the analyte in the liquid is maintained in the vicinity of the ligand receptors, hence modest local flow velocity variation over the capture surface is only of secondary effect. Transition from a narrow channel from the bubble removal system to a widened flow in the reaction chamber, e.g. to a flow width of 0.5 or 1 cm, enables a sheet-form, low Reynolds number flow of liquid over a capture surface that bears an array of many sets of spots of different ligand receptors. Each set may contain at least 3, preferably, 10, replicate spots of a ligand receptor, the spots preferably in rows oriented transversely to the direction of flow. This enables operations to be performed on the data to improve the sensitivity and coefficient of variation of the determined value with respect to each set of spots.

Other aspects of invention comprise a method of conducting an assay employing a cassette of any of the constructions previously described.

Another aspect of invention is a cassette for conducting an assay, the cassette comprising a solid surface carrying an array of spots of ligand receptor of diameter between about 50 micron and 500 micron, with spacing between spots at least about equal to the diameter of the spots, the array having a width greater than about 0.5 cm, the solid surface bearing the array constructed and arranged as one side of a flow passage having a width exceeding the width of the array, and a dimension of the gap between the surface bearing the array and an opposed, parallel, flow-confining surface of between about 80 and 300 micron, a pumping and passage system constructed to create a succession of flows through the width of the flow passage at Reynolds number less than about 1 of liquid sample containing ligand of interest and of developing liquid, or a succession of liquids, capable of attaching detectable tags to spots to which ligand of interest has attached, the cassette constructed to enable reading the detectable tags of the array. Preferably the gap is between about 100 and 200 micron and the pumping and passage system is constructed to provide the flows at Reynolds number between about $1 \times 10^{-1}$ and $5 \times 10^{-3}$, for instance the cassette is constructed with a gap of 100 micron, the spots of ligand receptor are of about 150 micron diameter, and the cassette is constructed for flows over the array at Reynolds number of about $2.7 \times 10^{-2}$.

Another aspect of invention is a method of conducting an assay employing an array of spots on a solid surface, the method comprising the steps of (a) providing on a solid surface an array of spots of ligand receptor of diameter between about 50 micron and 500 micron, with spacing between spots at least about equal to the diameter of the spots, the array having a width greater than about 0.5 cm; (b) arranging the solid surface bearing the array as one side of a flow passage having a width exceeding the width of the array, and a dimension of the gap between the surface bearing the array and an opposed, parallel, flow-confining surface of between about 80 and 300 micron; (c) creating a succession of flows through the width of the flow passage at Reynolds number less than about 1 of liquid sample containing ligand of interest and of developing liquid, or a succession of liquids, capable of attaching detectable tags to spots to which ligand of interest has attached; and (d) reading the detectable tags of the array. Preferably the gap is between about 100 and 200 micron and the flows over the array have a Reynolds number between about $1 \times 10^{-1}$ and $5 \times 10^{-3}$, for instance the gap is 100 micron, the spots are of about 150 micron diameter and the Reynolds number is about $2.7 \times 10^{-2}$. Preferably all steps of this method are performed using a cassette to house the liquids and to provide the pumping and passage system.

Assay cassettes and methods of conducting assays employing cassettes having one or more aspects of invention thus-far described can have one or more of the following features:

An agent stored on the cassette for combination with a liquid is a ligand or a substance comprising a detectable tag.

An agent stored in the chamber on the cassette is in dry state, exposed to air, the cassette constructed to enable introduction of the liquid to the chamber in combining action, a gas bubble removal system of the cassette being effective to remove micro-bubbles of the air produced by the combining action.

A chamber of the cassette in which combining of agent and liquid is to occur has an elastically distensible wall portion adapted to elastically expand in response to liquid displaced into the chamber, and to elastically contract when liquid flows out of the chamber.

The assay cassette comprises at least one liquid storage chamber associated with a displacement pump constructed to displace liquid in continuous flow from the storage chamber, to flow through the passage system or through the passage system with exposure to a heat transfer surface, the cassette constructed to enable exposure of the liquid to a gas bubble removal system prior to reaching the array, whereby gas micro-bubbles previously produced in the liquid can be removed before the liquid is directed in continuous flow over the array.

The assay cassette includes a displacement pump in the form of an elastic diaphragm forming a wall portion of a liquid storage chamber which is operable by an external, continuously movable actuator to produce a continuous flow.

The assay cassette comprises at least one liquid storage chamber associated with a displacement pump constructed to displace liquid in continuous flow from the storage chamber, an outlet to the passage system is located at the top of the liquid storage chamber, exposed to air present in the chamber, the cassette and pump, e.g. an elastic diaphragm, being constructed and arranged to expel air from the chamber followed by forcing liquid through the passage system in continuous flow via the gas bubble removal system and over the array.

The assay cassette has a liquid storage chamber constructed to contain a sealed pouch of liquid for the assay, the chamber associated with a device for puncturing the pouch to release the liquid.

The assay cassette has a liquid storage volume constructed to receive and store a liquid introduced to the cassette from the exterior, whereby gas micro-bubbles produced in the liquid by the step of introduction of the liquid to the cassette can be removed by a gas bubble removal system before the liquid flows over the array.

The assay cassette has a liquid storage chamber constructed to receive the liquid from the exterior via a needle or pipette projected through a septum, the septum comprising an elastomeric mass that has a pierced passage, the elastomeric mass mounted under substantial compression relative to the pierced passage, the compression effective to maintain the pierced passage closed but enabling insertion and removal of a plastic liquid-supply needle or pipette through the pierced passage.

The assay cassette has at least one waste chamber to which liquid flows after being pumped in continuous flow by a displacement pump, exposed to a gas bubble removal system and directed over the array, whereby the liquid is contained within the cassette throughout the assay.

The assay cassette is constructed and arranged so that during performance of the assay the capture surface and the liquid flow over it have an upward extent, and a waste chamber is positioned in the cassette to receive gravity flow of liquid that has passed over the capture surface.

The assay cassette is of generally planar extent and constructed to be disposed at a substantial angle to the horizontal during performance of the assay to dispose the capture surface to extend upwardly in the direction of the liquid flow to an upper end, and to locate a waste outlet for gravity flow from the upper end of the capture surface to a waste chamber.

The assay cassette has a liquid passage system which includes at least one actuatable valve through which liquid flows prior to being exposed to a gas bubble removal system, whereby gas micro-bubbles produced in the liquid by passage through the valve can be removed before the liquid is directed over the array.

The assay cassette has a valve comprising a valve seat across which liquid flows, the valve seat defining inlet and outlet passages, and an elastic diaphragm extends over the valve seat and is displaceable to engage the valve seat to interrupt the flow.

The assay cassette has a stop valve followed by a surface-tension burst valve, the burst valve being capable of blocking migrating liquid that may leak past the stop valve when the stop valve is closed, but, at flow pressure, capable of transmitting liquid to flow over the array.

The assay cassette has a flow passage system constructed and arranged to enable more than one slow flow of liquid of Reynolds number less than about 1, preferably, between about $1 \times 10^{-1}$ and $5 \times 10^{-3}$, over the array after exposure of the liquids to a gas bubble removal system.

The assay cassette is constructed to perform a sandwich assay in which liquid flows of the assay are exposed to the bubble removal system, the cassette comprising storage sites for liquid sample and all substances employed in the sandwich assay, the cassette having at least one waste chamber, the cassette being constructed and arranged to contain all liquids throughout the performance of the sandwich assay.

The assay cassette has a capture surface of extended width and carries a two-dimensional array of ligand-receptor regions comprised of spots of characteristic dimension between about 50 µm and 500 µm, and the liquid passage system includes a flow transition section preceding the capture surface that spreads the continuous, slow liquid flow to a width corresponding to the width of the capture surface.

The assay cassette has a capture surface exposed to the slow liquid flow of dimensions of at least about 0.5 cm in the direction of the flow and in the direction transverse to the direction of the flow.

The assay device has a flow transition section preceding the capture surface, the cross-section area of flow preceding the transition section is about 0.25 mm$^2$ or less and the cross-section area of the slow flow over the capture surface is at least 0.75 mm$^2$.

The assay cassette carries at least 3 replicate regions of each of a multiplicity of ligand receptors arrayed transversely to the direction of flow of the liquid over the capture surface, preferably the array on the capture surface also including, in regions in proximity to the regions of a given ligand receptor, reference regions of known quantity of the ligand to which the receptor is specific.

A bubble removal system of the assay cassette preferably comprises at least one buoyancy chamber to which the liquid is exposed.

The assay cassette is of generally planar extent and constructed to be disposed at a substantial angle to the horizontal during performance of the assay to dispose a gas bubble removing buoyancy chamber above a discharge outlet through which the liquid is directed to the capture surface.

The assay cassette is constructed so that when disposed at a substantial angle to the horizontal, the capture surface is located above a flow transition passage that receives liquid from a buoyancy chamber and spreads the liquid flow to a width corresponding with the width of the capture surface, the transition passage constructed to direct the liquid in continuous upward flow over the capture surface. In one preferred form, the assay cassette is constructed so that when disposed at the substantial angle to the horizontal, a waste outlet is located in position to receive the liquid following flow over the capture surface for gravity flow to a waste chamber in the cassette.

The assay cassette comprises a liquid storage chamber having an outlet passage, the cassette is constructed so that when disposed at a substantial angle to the horizontal, the storage chamber is below the capture surface, the storage chamber associated with an externally actuatable displacement pump that is effective to force liquid from the storage chamber in continuous flow through a buoyancy chamber and upwardly over the capture surface to a waste outlet.

The assay cassette, in operating orientation, has a buoyancy chamber with a top and bottom, a liquid inlet and a liquid outlet, both the liquid inlet and outlet being located near the bottom, in flow-aligned relationship.

The assay cassette has a buoyancy chamber and is constructed to enable initial filling of the buoyancy chamber by a liquid stored in the cassette, and to have a plurality of liquids of the cassette flow through the so-filled chamber in sequence, in laminar flow between the inlet and the outlet of the buoyancy chamber.

The assay cassette is constructed to enable exposure of each increment of liquid flow to a buoyancy chamber for a period between about 1 and 5 seconds.

The assay cassette has a buoyancy chamber comprising a depression molded in a face of a plastic body and channels molded in the face of the plastic body for liquid leading to and from the depression, and an adhesive sheet overlies the molded depression and the channels and is adhered to face portions of the molded body bounding the depression and channels.

A bubble removal system includes, in succession, at least two bubble capture zones to which a flow is exposed. Preferably, the bubble capture zones are constructed and arranged to enable bubbles to rise by buoyancy effects. In a preferred form, a buoyancy chamber is constructed for liquid flow from an inlet, along a path exposed to enable bubbles to rise by buoyancy effects for capture, to an outlet, there being at least one divider wall spaced along and above the liquid path to define upstream and downstream bubble capture zones exposed to the path such that a large bubble in liquid flow at the inlet, for instance during original liquid filling of the buoyancy chamber, will tend to be trapped in the upstream capture zone, leaving the downstream capture zone free to receive liquid flow. In one preferred form, the divider wall terminates in an upward region above which liquid entering the downstream zone can fill the upstream zone above any bubble lodged in a lower portion of the upstream zone. In preferred forms, this buoyancy chamber comprises a depression molded in a plastic body, there being a molded upstanding rib defining the divider wall, and an adhesive sheet overlies the molded depression, being adhered to face portions of the molded body bounding the depression, and adhered to an outer edge of the molded rib.

Another aspect of invention is a molded body for an assay cassette, the body defining at least one molded receptacle of depth suitable to hold an assay liquid, and a molded face wall, the molded receptacle being open at a face-side plane and the molded face wall having an outer face generally aligned with the face-side plane, the outer face of the face wall having at least one molded channel forming a liquid passage for directing liquid from the receptacle to an assay region of the cassette the face wall having a thickness substantially less than the depth of the receptacle and having a back surface at a heater cavity that is open from the backside of the body, the heater cavity constructed and arranged to removably receive a cooperatively constructed external heater to engage portions of the back surface of the face wall in surface-to-surface heat-transfer contact to heat liquid flowing in the molded channel by heat conduction through the thickness of the molded face wall.

Preferred embodiments of this aspect have one or more of the following features.

A chip-receiving opening is defined in the face wall to receive and position an assay chip so that the chip bounds a reaction chamber into which a molded channel of the face wall directs liquid, the heater cavity in the molded body extending below the chip-receiving opening to expose the chip for surface-to-surface heat-transfer contact with the external heater to heat liquid in the reaction chamber by heat conduction through the thickness of the assay chip. Preferably a portion of the backside of the chip is exposed to a temperature sensor to control the energization of the heater.

A receptacle is an analyte-receiving receptacle arranged to discharge into a molded channel of heat-exchange contour, preferably a serpentine contour, in a portion of the face wall that is arranged to receive heat from the heater.

One side of at least one liquefying chamber is molded as a depression in a portion of the face wall through which a liquid channel directs liquid, this portion of the face wall having a back surface exposed for engagement by the external heater for surface-to-surface heat transfer contact to heat liquid in the liquefying chamber by heat conduction through the thickness of the molded face wall.

One side of a bubble removal device is molded as a depression in a portion of the face wall through which a liquid channel directs liquid, this portion of the face wall having a back surface exposed for engagement by the external heater for surface-to-surface heat transfer contact to heat liquid in the bubble removal device by heat conduction through the thickness of the molded face wall, preferably this bubble removal device being a liquid-filled bubble trap.

An assay cassette comprises the molded body and a cover assembly secured over the receptacle and the face-wall of the molded body, the cover assembly including an elastic diaphragm portion lying over the receptacle, the diaphragm portion adapted to be deflected to displace liquid from the receptacle through the molded channel. In preferred forms, a portion of the face wall is molded in the form of a valve seat, and the cover assembly includes a diaphragm portion adapted to be deflected to engage the valve seat to stop flow.

The molded body is of generally planar extent and bound, at least substantially, by a perimeter wall of substantially constant depth extending between respective parallel planes.

The back surface of the face wall of the molded body is planar, preferably parallel to face-side and back-side planes of the cassette, and arranged to be engaged by a planar heat-delivering face of a heater. Preferably the heater comprises a flexible, sheet-form resistance heater mounted on a resilient planar pad carried on a rigid, planar plate that is mounted in floating manner enabling the corresponding planar surfaces of the molded body and the heater to self-adjust into face-to-face heat-transfer contact.

Another aspect of invention is a molded body for an assay cassette, the body defining at least one molded receptacle of depth suitable to hold an assay liquid and a molded face wall, the molded receptacle being open at a face-side plane and the molded face wall having an outer face generally aligned with the face-side plane, the outer face of the face wall having at least one molded channel forming a liquid passage for directing liquid from the receptacle to an assay region of the cassette, the front surface of the face wall being planar and adhered to an adhesive side of an adhesive sheet, at least one portion of the adhesive sheet lying over a channel in the face wall, closing the respective side of the channel. In preferred forms the adhesive sheet carries adhesive on its oppositely directed sides, the adhesive sheet having at least one window corresponding to a liquid receptacle or valve seat, one adhesive side of the adhesive sheet being adhered to the face wall and the oppositely directed adhesive side adhered to an elastic diaphragm sheet, a portion of the elastic diaphragm sheet lying over the window defining a deflectable pump diaphragm or valve diaphragm at a respective feature in the molded body. In preferred form, a second adhesive sheet carrying adhesive on its oppositely directed sides is adhered on one side to the outer side of the diaphragm sheet, and the oppositely directed adhesive side adhered to a relatively rigid cover member. In preferred cases, there is a window in the second adhesive sheet overlying a pump receptacle and a breakaway portion of the cover overlying the diaphragm at the pump receptacle is constructed to break from the cover to act as a pump piston head for deflecting the respective portion of the diaphragm in response to externally applied actuation force. In preferred cases the break away portions of the cover are adhered to corresponding outer surface portions of the diaphragm sheet.

The assay cassette is constructed for use with a protocol which produces light-emitting tags associated with complexes of receptor and ligand, the cassette having a window constructed and arranged to enable reading of light emitted from the tags, preferably the capture surface comprising a nitrocellulose layer of less than about 1 micron thickness.

The assay cassette is constructed as a disposable sandwich assay cassette for optical reading, the cassette operable by external apparatus, and having: a liquid storage chamber and associated displacement pump for producing a continuous flow of liquid sample containing an analyte ligand, at least a second liquid storage chamber and an associated displacement pump for producing flows of assay-supporting liquids for completing the assay, a flow-through reaction chamber in which a capture surface of extended width is situated, at least one waste chamber for receiving waste liquid from the reaction chamber, the liquid passage system including a flow transition section which spreads the liquid flow to the width of the capture surface, the capture surface carrying a two-dimensional array which includes spaced-apart replicate regions of ligand receptors, the capture surface being positioned and arranged for optical reading, the liquid passage system comprising a flow network for directing flows of the sample and assay-supporting liquids through the reaction chamber, over the capture surface, a venting arrangement for air displaced by liquid forced through the system, and heat transfer surfaces arranged to receive heat to bring the liquids to about desired assaying temperature prior to entering the bubble removal system and to maintain the reaction chamber at assaying temperature, and the liquid displacement pumps of the storage chambers, the flow network including the associated gas bubble removal system and transition section, and the reaction chamber cooperatively constructed to produce relatively widened flows of Reynolds numbers less than about 1 of a sequence of liquids over the capture surface, thence to the waste chamber.

The assay cassette, constructed as a disposable sandwich assay cassette, has heat transfer surfaces to which the liquids are exposed that are in heat-transfer relationship to an exterior surface of the cassette, the exterior surface of the cassette adapted to be placed in heat-receiving relationship with a heater member of the external apparatus.

The assay cassette has a bubble removal system which, in operating orientation, comprises an upwardly extending buoyancy chamber adapted to contain liquid and having a top, a liquid inlet and a liquid outlet, the outlet located lower than the top of the buoyancy chamber in position adapted to be submerged in liquid of the buoyancy chamber, there being a vent passage from the upper portion of the buoyancy chamber. Two embodiments of this feature are presently preferred. In one embodiment, the buoyancy chamber communicates with an air vent associated with a waste chamber of the cassette until the buoyancy chamber receives liquid, a first surface-tension burst valve being associated with a passage leading from the liquid outlet from the buoyancy chamber, the first burst valve being constructed and arranged to be effective to prevent liquid flow beyond the buoyancy chamber until the chamber is filled with liquid, and the vent passage comprises an air-porous but liquid-blocked element located in the top region of the buoyancy chamber permitting air to exhaust from the chamber but blocking passage of liquid. In another embodiment, the buoyancy chamber communicates with an air vent associated with a waste chamber of the cassette until the buoyancy chamber is initially filled with liquid, a first surface-tension burst valve being associated with a passage leading from the liquid outlet from the buoyancy chamber, and a second surface-tension burst valve communicating with the top of the buoyancy chamber being associated with the vent passage, the first burst valve being constructed and arranged to be effective to prevent liquid flow beyond the buoyancy chamber until the chamber is filled with liquid, and the second burst valve being constructed and arranged to be effective to prevent liquid flow from the top of the buoyancy chamber after the buoyancy chamber is filled with liquid.

According to another aspect of invention, an assay cassette combines, in particular, a capture surface for a receptor ligand, a liquid passage system for liquid flows at Reynolds numbers less than about 1, preferably between about $1\times10^{-1}$ and $5\times10^{-3}$, a temperature control region constructed to enable all liquids associated with the assay to be brought approximately to an assaying temperature, and a gas bubble removal system following the temperature control region to which the liquid is exposed prior to reaching the capture surface, the gas bubble removal system constructed to remove gas micro-bubbles from the liquid to improve capture of a ligand in the liquid, the gas bubble removal system comprising an upwardly extending buoyancy chamber adapted to contain liquid and having a top, a liquid inlet and a liquid outlet, the outlet located lower than the top of the buoyancy chamber in position adapted to be submerged in liquid of the buoyancy chamber, there being a vent passage from the upper portion of the buoyancy chamber.

According to another aspect of invention, in embodiments of the cassette that have a buoyancy chamber, the liquid passage system is constructed to initially fill the buoyancy chamber with liquid from a first storage volume in a manner that a further flow passage to be connected to provide flow of another liquid through the buoyancy chamber can be isolated and remain empty during the filling of the buoyancy chamber, and the buoyancy chamber is sized to receive and contain air displaced from the empty passage when liquid is forced through the further passage on its way to the buoyancy chamber without exposing the liquid outlet from the buoyancy chamber to air filling the top of the buoyancy chamber.

In embodiments of various aspects of invention, the assay cassette comprises a generally planar molded body of rectangular form of length of about 8 cm. or less and width of about 5 cm. or less, constructed to be oriented with its longitudinal axis disposed at a substantial angle to the horizontal during use; in such orientation, substantially the lower half of the body defining, in side-by-side manner, a storage chamber for a pouch of buffer liquid, a chamber for a detection ligand stored therein in desiccated form, and a chamber for a fluorescent tag agent stored therein in desiccated form; a reaction chamber containing the capture surface located adjacent the opposite longitudinal end of the molded body, at least one storage chamber disposed laterally to one side of the reaction chamber, positioned to receive gravity flow of waste from the reaction chamber; and a temperature control region arranged to heat liquids prior to the liquids entering the gas bubble removal system.

According to another aspect of invention, a method of conducting an assay comprises providing an assay cassette, selected from any of the constructions described above, and external apparatus suitable to control the assay, introducing a sample to a sample chamber of the cassette, and, according to a predetermined assay protocol, conducting the assay under control by the external apparatus, including continuously flowing the sample and supporting liquids over the capture surface at Reynolds numbers less than about 1, preferably between about $1\times10^{-1}$ and $5\times10^{-3}$, for selected durations and reading the capture surface of the cassette.

According to another aspect of invention, a method of conducting a sandwich assay comprises providing a sandwich assay cassette selected from any of the types described above for sandwich assays, and external apparatus suitable to control the assay, wherein the capture surface carries an array of replicate regions of ligand receptor specific to a ligand of an analyte molecule, introducing a liquid sample that includes the analyte to the sample chamber and, according to a predetermined sandwich assay protocol suitable for optical reading, under control of the external apparatus, at Reynolds numbers less than about 1, preferably between about $1\times10^{-1}$ and $5\times10^{-3}$, causing, sequentially, continuous flow through the reaction chamber of the sample at a predetermined flow rate for a predetermined time, and continuous flows of assay-supporting liquids for appropriate times, and optically reading the capture surface of the cassette. In some cases the capture surface carries replicate deposits of receptor ligands in the form of an antigen or antibody specific to an analyte molecule, and the sample contains the analyte molecule.

Another aspect of invention is a method for determining the concentration of at least one analyte in a liquid sample employing only liquids contained in a cassette, comprising the steps of: (a) providing a cassette, the cassette including: (i) a capture surface having, for each analyte, immobilized binding agent having replicate binding sites specific for the analyte, the binding agent being divided into a set of at least 3 spatially separated locations on the capture surface; and (ii) a liquid developing system capable of providing at least one liquid for developing the complex of analyte and binding agent by attaching thereto a signal-producing tag in manner to quantitatively indicate by strength of signal the amount of analyte bound to each location; (b) inserting the liquid sample into a storage volume in the cassette; (c) producing from the stored sample a continuous flow at controlled rate of the liquid sample over the capture surface for a predetermined interval to enable binding of the at least one analyte to the respective locations of binding agent; (d) developing the complexes of analyte and binding agent at the sites by producing from the liquid developing system stored on the cassette at least one continuous flow at controlled rate of liquid over the capture surface for predetermined duration, sufficient to bind the tag to complexes at the locations in manner to provide quantitative indication of the amount of analyte bound to each of the locations; (e) with liquid stored on the cassette, washing the capture surface to remove unbound material capable of producing false signal; (f) measuring signal produced by the tag at locations on the capture surface to obtain a value representing the fraction of binding sites occupied by the analyte at each location; and (g) performing an operation on the values for the set of locations to determine a value of the concentration of the analyte in the liquid sample.

Preferred embodiments of this method have one or more of the following features:

Each increment of the liquid flows of the method is exposed to heating, and to a bubble removal region for a period of between about 1 and 5 seconds, before flowing over the capture surface.

Each set of locations of binding agent for the method comprises at least 5 locations and the operation performed on the set of values comprises discarding at least one highest and one lowest value and employing intermediate values to determine a mean value.

The developing system employed in the method comprises a detection agent capable of binding at each location in manner based on the quantity of analyte bound at the location, and a signal-producing tag capable of binding to the detection agent, the method including producing, in sequence, continuous controlled flows of a liquid containing the detection agent and a liquid containing the tag. In many cases, preferably, the binding agent is an antigen or antibody and the analyte is, respectively, an antibody or antigen.

The method employs fluorescent tags and measuring is performed by exciting the tags and measuring the resultant fluorescence.

The method is performed with at least 3 locations of binding agent distributed in a row across the width of a flow path for the continuous flow over the capture surface. In preferred cases, the method includes use of at least one row of locations bearing preformed calibration deposits of analyte of predetermined concentration, which are developed, measured, and employed to correlate the signal with concentration and to determine that the system has performed correctly. In preferred cases, there are calibration locations having analyte deposits of differing known concentrations.

The method is performed with flows over the capture surface at Reynolds numbers of the order of 1 or lower, preferably between about $1 \times 10^{-1}$ and $5 \times 10^{-3}$.

The method is employed to screen serum banks, which are available in only limited quantities. The method reduces the volume of sample required per assay, increasing the utility and value of the serum banks.

Other aspects of invention concern other combinations of cassette features and their method of use.

According to another such aspect, an assay cassette is constructed to perform a predetermined multi-flow assay in response to control by external apparatus, comprising: a reaction chamber having a capture surface of extended width that carries a two dimensional array of spaced-apart regions of ligand receptors, the two dimensional array including at least three replicates each of multiplicity of ligand receptors; a storage chamber for liquid sample, a storage site for at least one substance required by the assay, and at least one waste chamber, the cassette being constructed and arranged to contain all liquids used in the assay throughout the performance of the assay; heat transfer surfaces arranged to receive heat to heat the liquids to about a desired assaying temperature prior to entering the reaction chamber and to maintain the reaction chamber at about such assaying temperature; and a liquid passage system defining a flow network which includes a transition section that spreads liquid flow to a width corresponding to the width of the capture surface, the cassette adapted, under control of the external apparatus, to direct a succession of continuous flows from the storage chamber and storage site over the capture surface of extended width to the waste chamber in accordance with a multi-flow assay protocol. In preferred embodiments, the assay cassette includes a gas bubble removal system, the cassette constructed to enable exposure of the liquid to the gas bubble removal system prior to reaching the array, whereby gas bubbles produced in the liquid by the temperature change can be removed before the liquid is directed over the array.

Embodiments of assay cassettes featuring this aspect can have one or more of the features described above or one or more of the following features:

The assay cassette is constructed for use with a protocol which produces, on the array, light-emitting tags associated with complexes of receptor and ligand, the cassette having a window constructed and arranged to enable reading of light emitted from tags associated with complexes of receptor and ligand on the capture surface.

The assay cassette has a flow network which includes at least one valve operated by actuating motion applied by the external apparatus to alter a flow path in the flow network.

The assay cassette has a flow network which includes at least one sensing station adapted to receive an optical sensing beam and enable the beam to pass through a flow passage and thence to a detector in the manner that the beam at the detector is altered in detectable manner by arrival of a liquid-air interface in the flow passage at the sensing station, the altered beam useful as a control signal by external apparatus during conduct of the assay. In preferred embodiments of this feature the sensing station includes a mirror constructed to reflect the beam after it passes through the passage, to return the beam through the passage to a detector of the external apparatus, or the sensing station defines a path for the beam to reach a detector on the side of the passage opposite from the side at which the beam was received.

The assay cassette contains an assay-supporting liquid stored in a rupturable pouch, the flow network incorporating a combining chamber for desiccated material useful as a detection antibody or antigen and a second combining chamber for a dry fluorescent or luminescent tag agent, the flow network associated with valves operable by the external apparatus for successively causing continuous flow through the reaction chamber of sample, detection antibodies or antigen in buffer, tag agent in buffer, and wash. In preferred embodiments of this feature, the assay cassette is constructed to deliver wash liquid by the flow network via a dedicated wash passage extending from a storage chamber or it is constructed to deliver wash liquid via a detection antibody or antigen flow passage.

According to another aspect of invention, an assay cassette is provided comprising: a capture surface that carries a two-dimensional array of spaced-apart regions of ligand receptors, at least one liquid storage chamber associated with a displacement pump constructed to displace liquid from the storage chamber to flow through a liquid passage system and over the array, a vented waste chamber to which the liquid is directed after being directed over the capture surface, the cassette constructed and arranged so that during performance of the assay the capture surface lies above the waste chamber, and the waste chamber is arranged in the cassette to receive gravity flow of liquid that has passed over the capture surface. Embodiments featuring this aspect can have one or more of the features described above or the following feature:

The assay cassette is constructed to be disposed at an angle in assaying position relative to a rest position, in which a venting arrangement comprises an air vent communicating with the waste chamber, the air vent comprised of material that is permeable to air until wetted, the material located not to be wetted by liquid in the waste chamber when the cassette is in assaying position and to be wetted by liquid from the waste chamber when the cassette is placed in rest position after use.

According to another aspect of invention, an assay cassette is provided comprising: a capture surface that carries a two-dimensional array of spaced-apart regions of ligand receptors, and a liquid passage system defining a flow network constructed to direct a flow of ligand-containing liquid over the array, the assay cassette having a body of generally planar extent defining at least one liquid storage chamber and at least one valve seat associated with a passage of the flow network, the cassette having a generally sheet-form elastic member mated with a first side of the body, the sheet-form elastic member having a portion over-lying the liquid storage chamber to define a displacement diaphragm for displacing fluid from the chamber in response to a linear pump actuator of external apparatus and the sheet form elastic member having a portion overlying the valve seat to define a valve diaphragm responsive to a linear valve actuator of the external apparatus.

Embodiments featuring this aspect can have one or more of the features described above or one or more of the following features:

The assay cassette defines a sample liquid chamber and a buffer liquid chamber, each associated with a pump diaphragm, and at least two valve seats for valves associated with passages of the flow network, portions of the sheet-form elastic member defining pump diaphragms and valve diaphragms respectively for the liquid chambers and the valves.

The assay cassette includes a combining chamber containing a material to be combined with a liquid, the sheet-form elastic member having a portion overlying the chamber to define an elastic diaphragm adapted to distend and restore in response, respectively, to forward and backward flow to and from the combining chamber of liquid from a liquid storage chamber. A relatively rigid molded cover may lie over the diaphragm, the cover having a molded cavity facing the diaphragm, defining an expansion cavity for the diaphragm and liquid during combining action. The combining chamber may be associated with a displacement pump constructed to operate in both pressure-producing and suction-producing directions.

The assay cassette has a molded body defining on one side the liquid passage system, the valve seat and the volume of the liquid storage chamber and defining on its opposite side a heat transfer surface configured to receive heat conducted from a heater member of the external apparatus.

The assay cassette has a cover of relatively rigid material located outside of and extending over a side of the body of the cassette, a break-away portion of the cover over-lying the displacement diaphragm and connected to surrounding portions of the cover by breakable connections, the break-away portion of the cover adapted to be engaged on its outside by a linear actuator of an external apparatus in the manner that initial displacement of the actuator breaks the breakable connections to form a piston surface of the break-away portion, and continued motion of the actuator displaces the break-away portion and engaged diaphragm to displace fluid beneath the diaphragm into a portion of the liquid passage system.

The assay cassette has a viewing window and a cover lying over the viewing window is sized and arranged to form a light baffle that substantially limits light exposure to the spotted array on the capture surface.

The assay cassette has a liquid storage chamber constructed to receive and store a sealed pouch of liquid for the assay, and protruding from the diaphragm, a projection capable of puncturing the pouch to release the liquid for pumping. A break-away portion of a relatively rigid cover of the cassette may carry the projection, exterior actuation force applied to the break-away portion of the cover effective to separate the break-away portion, and force the projection to puncture the pouch. The projection and elastic diaphragm may be united in predetermined manner in which the projection extends through the diaphragm, and a seal extending between the diaphragm and the breakaway portion extends around the projection.

According to another aspect of invention an assay cassette is provided comprising: a capture surface that carries an array of spaced-apart regions of ligand receptors, a liquid passage system constructed to direct a flow of ligand-containing liquid over the array, and at least one liquid storage chamber, the liquid storage chamber associated with a displacement pump in the form of an elastic diaphragm forming a wall of the liquid storage chamber, the diaphragm constructed to displace liquid from the storage chamber to flow through the liquid passage system and over the array, the liquid storage volume constructed to receive and store a sealed pouch of liquid for the assay, and protruding beyond the diaphragm, a projection capable of puncturing the pouch to release the liquid for pumping and flow over the array.

Embodiments featuring this aspect can have one or more of the features described above or one or more of the following features:

The assay cassette has the projection and elastic diaphragm united in predetermined manner in which the projection extends through the diaphragm, and a seal extending between the diaphragm and the breakaway portion extends around the projection.

The pouch, prior to use, is held in position separated from the diaphragm and the projection. The pouch may have spacer members constructed to space the pouch from the diaphragm while leaving the pouch accessible to the diaphragm when the diaphragm is displaced.

According to another aspect of invention, an assay cassette is provided comprising: a capture surface that carries an array of spaced-apart regions of ligand receptors, a liquid passage system constructed to direct a flow of ligand-containing liquid over the array, and a liquid storage chamber constructed to receive the liquid from the exterior via a needle or pipette projected through a septum, the septum comprising an elastomeric mass that has a pierced passage, the elastomeric mass mounted under substantial compression relative to the pierced passage (e.g. mounted under compression transverse to the passage, e.g. radially), the compression effective to maintain the pierced passage closed but enabling insertion and removal of a plastic liquid-supply needle or pipette through the pierced passage.

According to another aspect of invention, an assay cassette is provided which is controllable by external apparatus and comprising: a capture surface that carries an array of spaced-apart regions of ligand receptors, a liquid passage system constructed to direct a flow of ligand-containing liquid over the array, the liquid passage system comprising a flow network which includes at least one sensing station adapted to receive an optical sensing beam and enable the beam to pass through a flow passage and thence to a detector in the manner that the beam at the detector is altered in detectable manner by arrival of a liquid-air interface in the flow passage at the sensing station, the altered beam useful as a control signal by the external apparatus during conduct of the assay. The sensing station may include a mirror constructed to reflect the beam after it passes through the passage, to return the beam through the passage to a detector of the external apparatus, or the sensing station may define a path for the beam to reach a detector on the side of the passage opposite from the side at which the beam was received.

According to another aspect of invention, an assay cassette comprises: a capture surface that carries an array of spaced-apart regions of ligand receptors, a liquid passage system constructed to direct a flow of ligand-containing liquid over the array, and a liquid storage chamber arranged to discharge via a portion of the liquid passage system into a combining chamber containing a material to be combined with liquid, the chamber having a wall defined by an elastic diaphragm adapted to distend and restore in response respectively to forward and backward flow of the liquid from its storage chamber. The material to be combined with liquid may be desiccated detection antibody, antigen or tag agent stored in the chamber prior to use. A relatively rigid molded cover may lie over the diaphragm, the cover having a molded cavity facing the diaphragm, defining an expansion cavity for the diaphragm and liquid. The chamber may be associated with a displacement pump constructed to operate in both pressure-producing and suction-producing directions.

According to another aspect of invention, an assay control apparatus is provided for performing an assay with any of the assay cassettes described above, the cassette having at least one displaceable membrane associated with a liquid storage chamber to form a displacement pump, the apparatus having a linear actuator mutually constructed and arranged to progressively displace the displaceable membrane over a controlled period to produce a timed continuous flow of liquid through the passage system and over the capture surface of the cassette.

The assay control apparatus may have one or more of the following features.

The assay control apparatus has multiple linear actuators of similar construction for use with an assay cassette having a corresponding number of membrane displacement pumps.

The assay control apparatus has one or more valve actuators for engaging diaphragm stop valves of the cassettes.

The assay control apparatus has a cassette receiving station constructed and arranged to dispose a cassette at substantial angle to the horizontal relative to the rest position of the cassette to orient a gas bubble removal chamber of the cassette in operating position and to dispose a waste chamber to receive waste from the capture surface by gravity flow.

The assay control apparatus incorporates an optical reader.

The assay control apparatus incorporates an optical system for detecting arrival of a liquid air interface within a liquid passage of a cassette.

According to another aspect of invention an assay system comprises a cassette and an assay control apparatus, the cassette comprising a capture surface that carries an array of spaced-apart regions of ligand receptors and a liquid passage system constructed to direct over the array a slow flow of assay-supporting liquids having Reynolds numbers less than about 1, the liquids including a ligand-containing liquid, the cassette including a gas bubble removal system to which the liquids are exposed, the gas bubble removal system constructed and arranged to remove gas micro-bubbles from the liquids prior to exposure of the liquids to the array, the bubble removal system of the assay cassette comprises at least one buoyancy chamber to which the liquid is exposed, the assay control apparatus having a cassette receiving station constructed and arranged to dispose a cassette at substantial angle to the horizontal relative to the rest position of the cassette to orient the buoyancy chamber of the cassette in operating position and to dispose a waste chamber to receive waste from the capture surface by gravity flow.

Embodiments of this aspect may have any of the features described above for assay control apparatus and for cassettes having buoyancy chambers for gas bubble removal.

The aspects of invention described above contribute to a robust general approach to achieving multiple ligand receptor-ligand assays in a miniaturized format with high sensitivity and high precision, and to solving the problems of implementation in low-cost, highly reliable ways.

Another aspect of invention is a general improvement of microfluidic biological assays carried out under extremely low Reynolds Number ($N_{Re}$). Such assays depend on the diffusion behavior of the analyte, as the molecular motion by diffusion is greater than that achieved by liquid motion. The diffusion properties (the time to mix by diffusion) are strongly influenced by the temperature of the liquid. The diffusion coefficient for bio-molecules in water is proportional to the absolute temperature of the assay and inversely proportional to the viscosity of water. For example when an assay temperature is raised from 25 to 37 degree Celsius, the diffusion coefficient is multiplied by 1.34 and the time to mix by diffusion to reach the same assaying condition is reduced by the same amount. Protein based bioassays are commonly terminated prior to equilibrium condition having been reached as equilibrium may require as long as a few hours. It is highly desirable to heat the analyte preferably to the normal body temperature rather than proceed at room temperature or storage temperature. Aspects of invention presented here enable this to occur without detriment.

Another aspect of invention deals, generally, with deficiency in the application of microfluidic systems to protein-based biological assays, concerned with the difficulty of sensing the passage of fluids through small channels. The absorption difference between air and water in a channel of less that 100 micron thick is extremely small, and peaks at 0.5% of that of air alone when viewed in the near IR. Aspects of invention presented here solve this dilemma by detecting not the change in liquids but the liquid-to-air interface as it arrives due to index of refraction at the interface.

Another aspect of invention deals, generally, with deficiency in microfluidics concerning the necessity of introducing samples containing protein, such as serum, into microfluidic devices through narrow typically stainless steel needles that have high internal surface area vs. volume. This has seemed to be a requirement due to the fact that, heretofore, septums used to seal ports of the device are made from materials that are highly rigid and impermeable. The rigidity of the material was thought necessary to provide a sufficient seal to ensure that the device would not leak. This has been a disadvantage, because commonly-used plastic pipette tips are not sharp enough to puncture a rigid septum, and thus could not be used to inject sample in the device. A transversely or radially compressed, pre-pierced septum provides a microfluidic device for performing a protein-based biological assay that is sealed with a septum that can be penetrated by a blunt instrument, and preferably by an instrument having a thicker bore, such as a plastic pipette tip.

In another aspect of invention, features are provided to prevent a user from improper handling of the microfluidic cassette device.

Another aspect of invention features a device, i.e. a cassette or cartridge, that includes one or more capture agents specific for one or more analytes, e.g., a panel, or biomarkers. The cassette or cartridge is used to perform several functions in a single device, such as sample capture, gas bubble removal, system calibration, and the measurement of analytes in a liquid sample. Preferably, the device is used in combination with a processing/reading instrument for the simultaneous measurement of one or more analytes. The device can be inserted in the associated processor/optical reader instrument, which automatically operates a number of necessary functions and images the reaction chamber for analysis of the assays as described below. Preferably, the device is a disposable device.

Another aspect of invention permits the simultaneous performance of a multitude of miniaturized sandwich assays, combining dilution series of a given capture molecule as well as a choice of different capture molecules. A fluorescent label can be used to provide a signal that can be read using an optical reading station, such as that exemplified in WO/04/017374A2 (PCT/US03/25702), hereby incorporated by reference. Other detection labels can also be used, such as luminescent molecules and chromogenic dyes. Capture molecules are preferably adsorbed to a nitrocellulose based surface exemplified by associated patent application WO/04/018623A2 (PCT/US03/25685). In addition, the device described herein can be used to perform nucleic acid based assays.

Another aspect of invention involves use of larger (in comparison e.g. to some cassettes available for genetic research) reaction-chambers on a cassette with assay redundancy, and consequently less ambitious reaction/assay densities, that lead to greater assay reliability. By these provisions, analyte molecule depletion by the capture sites is minimized and gap dimension tolerances can be relaxed to yield economic manufacturing of the cassette. Micro-bubbles and other perturbations can be statistically minimized and have relatively little consequence. Larger reaction chamber and appropriate temperature control and flow duration alleviate the effect of substantial differences in viscosity and diffusivity of analyte. Control assays can be incorporated and processed simultaneously. Thus one can simultaneously perform a plurality of sandwich assays or complimentary assays with a high degree of certitude.

Another aspect of invention is a self-calibrating biochip for conducting an assay comprising a capture surface bearing a set of replicate deposits of a given ligand receptor for the assay and bearing, in association with that set, a set of calibration deposits that comprises a number of groups of replicate deposits of the ligand for which the ligand receptor is specific, the groups being of respectively different known dilutions of the ligand, the known dilutions, selected, when developed, to be sufficient to define a calibration curve for assay measurements made at the deposits of the given ligand receptor after their exposure to a sample containing the ligand, the groups of calibration deposits being adapted to be developed by attachment of a readable tag to all ligand on the capture surface at the deposits of ligand. Preferably at least one row of control deposits of given measurable intensity is also included on the capture surface of the biochip for verification of operation of the measuring system.

Preferred embodiments of this aspect of invention have one or more of the following features.

The deposits comprise spots in a spotted array.

The tag is a fluorescent tag.

The biochip is constructed for exposure to a sheet-form stream of sample and reagent having a direction of flow, the replicate deposits being spots arranged in at least one row oriented transverse to the direction of the flow, and the groups of calibration deposits being spots arranged in rows transverse to the direction of the flow.

The replicate deposits of ligand receptor are in one or more rows transverse to the flow, for instance a row of ten spots, and calibration deposits of each given dilution are arranged in one or more rows transverse to the flow, for instance each group comprising a row of ten spots.

A row of replicate deposits of the ligand receptor may, for instance, occur in lead position relative to the flow, followed by successive rows of calibration deposits. The successive rows of calibration deposits may be arranged in order of dilution, the highest dilution being first occurring following the replicate deposits of ligand receptor. The deposits of ligand receptor and ligand may be, for instance, of spot form oriented in a pattern relative to the flow such that each spot is most closely followed by spots that are offset from alignment in the direction of flow with the preceding spot.

The capture surface is of extended width carrying, in transverse arrangement, deposits of more than one ligand receptor and associated calibration deposits.

Another aspect of invention is an assay method employing a self-calibrating chip of any of the kinds just described, which includes exposing the capture surface to a flow of sample containing the ligand followed by exposing the capture surface to conditions by which a readable tag becomes attached to all ligand present, reading the tag by a reader to obtain measurements of each deposit, analyzing the data from the group of calibration deposits to develop a table of calibration values, comparing a value derived from the group of ligand receptors with values from that table and deriving therefrom a value representing the concentration of the ligand in the analyte. In preferred embodiments the tag is a fluorescent tag, and the reader is a fluorescence reader.

In general, the analyte to be detected is a compound, composition, aggregation, or other substance that can be specifically captured from a complex mixture of compounds, compositions and aggregations. That is, the analyte, or portion thereof, will be antigenic or haptenic having at least one determinant site, or will be a member of a naturally-occurring binding pair, e.g., carbohydrate and lectin, hormone and receptor, complementary nucleic acids, and the like. Analytes of particular interest include antigens, antibodies, proteins, carbohydrates, haptens, drugs, hormones, hormone metabolites, macromolecules, toxins, bacteria, viruses, enzymes, tumor markers, nucleic acids, and the like, although other types of substances may also be detected.

The systems presented are useful in assaying for a wide variety of analytes in virtually any type of sample which can be provided in a liquid form. Especially suitable are biological specimens, such as blood, serum, plasma, urine, cerebral fluid, spinal fluid, ocular lens liquid (tears), saliva, sputum, semen, cervical mucus, scrapings, swab samples, and the like. Cell lysates (cell culture supernates) can be used. In addition, the method is suitable for industrial, environmental and food samples, such as water, reservoirs, process streams, milk, meat, poultry, fish, conditioned media, and the like. Under certain circumstances, it may be desirable to pre-treat the sample, such as by suspending in liquid, separation, dilution, concentration, filtration, chemical treatment, or a combination thereof, in order to improve the compatibility of the sample with the remaining steps of the assay. The selection and pretreatment of biological, industrial, and environmental samples prior to immunological testing is well known in the art.

Categories of immunoassays that may be performed include direct and indirect competitive assays, and non-competitive assays such as sandwich assays. A competitive assay relies on competition for binding to a specific binding agent between a known amount of labeled analyte and an unknown amount of analyte in the sample. The more analyte that is present in the sample, the less binding agent available to bind to a competing analyte or analyte-analogue. Preferably, the method is based on a sandwich immunoassay. In a sandwich assay, a binding agent (ligand receptor) is immobilized on a solid support to serve as a capture agent. Analyte (the ligand) in the test sample is allowed to react with the binding agent on the support. Afterward, a second, detectable agent (that includes a tag or can receive a tag) binds specifically to a different epitope on the analyte, the analyte becoming "sandwiched" between the detectable binding agent and the immobilized binding agent. After any excess detectable binding agent or later-added tag is washed away, observations are made of the detectable agent in the sandwich complex. The observed signal is directly proportional to the amount of analyte in the test sample.

An especially important contribution here is the provision of features that contribute to a single assay technique (or "platform") for protein biomarkers which, above all, is robust. The assay technique can produce highly credible results, with low coefficients of variation (and so is highly repeatable), and is immune to interferences and performs its function with sufficient margins that it is useful over a wide range of analytes, levels of dilution and starting conditions that heretofore have called for using a number of different assay techniques. Furthermore, such a robust assay technique is provided that also is sensitive, is capable of significant throughput, employs equipment that is easy to use and has small footprint, and is capable of extensive multiplexing (conducting multiple assays at once). Preferred embodiments are implemented to require little sample or reagent, to require little handling of the sample, and to enable simple design of particular assays.

BRIEF DESCRIPTION OF THE DRAWINGS

FIG. 1 shows, by isometric diagram, a wide capture surface in a reaction chamber exposed to a flow of analyte, while FIG. 1A depicts separated spots of ligand receptor on the capture surface and the volume of ligand-containing liquid to which a spot is exposed.

FIG. 2, as one example of prior art, shows one of multiple lanes of a cross-lane flow configuration, while FIG. 2A depicts the area of analyte flow exposed to a cross-lane of capture reagent.

FIG. 4 is a diagram of a generalized disposable assay cassette and steps performed on the cassette, while

FIG. 7 is an exploded isometric view of elements of the cassette of FIG. 6.

FIG. 8E, is a diagrammatic cutaway view of the control unit showing mechanical actuators for the cassette.

FIGS. 12A, 12B and 12C, illustrate progressive positions of the linear actuator relative to the pouch.

FIGS. 13 and 13A illustrate a diaphragm valve of the cassette of FIGS. 6 and 7, respectively in open and closed positions, while

FIGS. 15 and 15A are exploded and cross-sectional installed views of a system that seals a sample injection port to the cassette and facilitates introduction of plastic pipettes and the like.

FIGS. 16, 16A and 16B are formats of spotted arrays.

FIG. 17 is a diagram illustrating the automated assay action, while

DETAILED DESCRIPTION OF PREFERRED EMBODIMENTS

Figure 1:
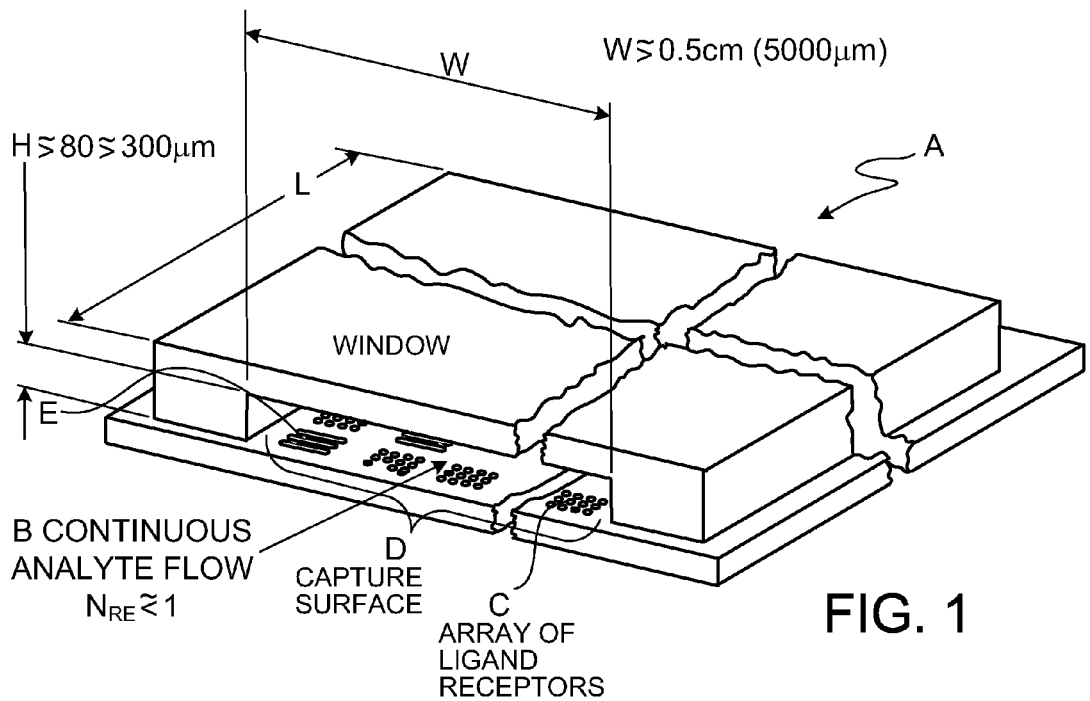

FIG. 1 shows, in magnified view, cassette reaction chamber A receiving flow B of a ligand-containing liquid. The liquid flows over array C of ligand receptors on a capture surface D. In preferred embodiments, characteristic dimensions of the two-dimensional array C are greater than about 0.5 cm; in one preferred embodiment the capture surface is 9.7 mm wide, W, and 12.5 mm long, L. The gap height H of sheet-form flow over the capture surface is preferably between about 80 and 300 µm (micron). In preferred embodiments, gap H is between 100 and 200 µm. The array C of capture reagent is located at a safe distance from the channel corners, typically 1.5 mm. This helps avoid any gas micro-bubbles that might grow in the corners.

FIGS. 1 and 1A show capture reagents attached to the surface D of a solid support as round spots R which are grouped in subsets associated with specific ligand receptors. While spots shown in FIG. 1 are in rectangular groups, which can be effective, rows of replicate receptors arranged transversely to the flow followed, by rows of reference spots, as in FIGS. 16 and 16A, have advantages that will be described. In the preferred embodiment 6 to 10 replicate spots of diameter between about 50 and 500 µm are employed in each group or row.

Another option suggested in FIG. 1 is the printing of ligand receptors in the shape of lanes E with one or a number of lanes, possibly 125 µm×1,000 µm, spaced apart 250 to 500 µm.

As will be explained, statistical analysis of replicate data can minimize errors due to spotting inaccuracies, obscured regions, highly polluting fluorescent particulates, and other causes. In another method, pixel data signal from all spots or lanes with equal capture reagent may be aggregated prior to use in analysis.

Figure 2:
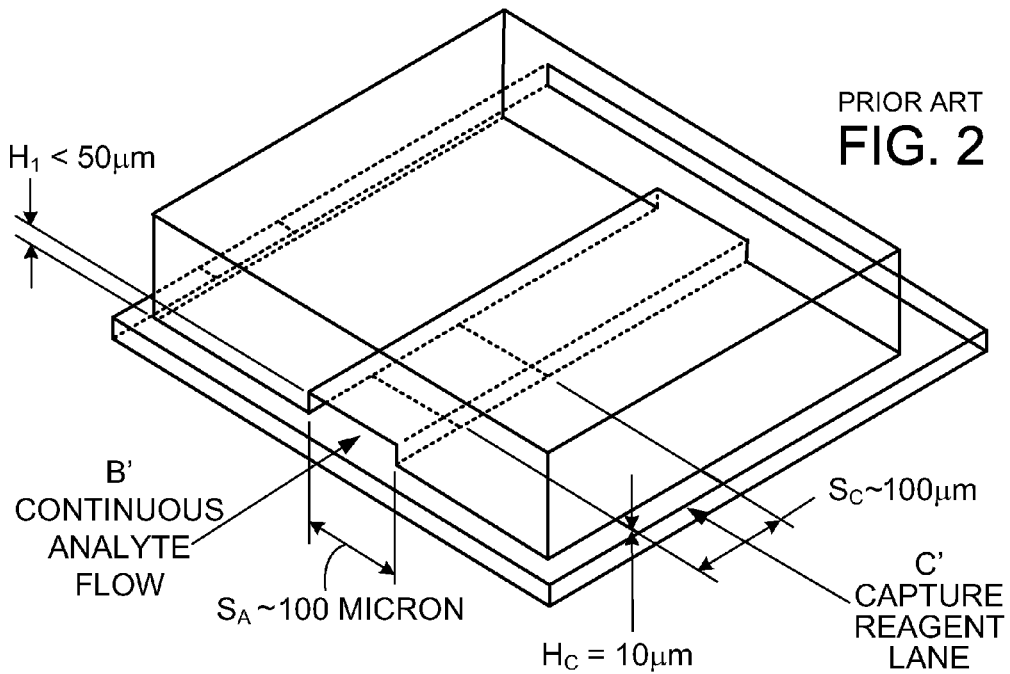

With reference to FIGS. 2 and 2A, one example of a prior art cassette employs microchannels to define a small reaction interface. A lane of capture reagent C' is intersected by a microchannel filled with analyte B'. In an idealized immunoassay, equilibrium might be attained, but in practice the assay is usually terminated before reaching equilibrium or, as may be the case, without knowing if equilibrium has been reached. Numerous variables contribute to reaction inconsistency in a given assay of this type. These include variations in the molecular density in the liquids as well as in viscosity and diffusivity, and include binding of micro-bubbles of air or gas as well as micro-particulates. All of these can disrupt the accuracy of the reaction. Micro-bubbles tend to lodge in corners, especially where surface properties exhibit a discontinuity such as where capture analyte intercepts a microchannel. Note that a 50 μm diameter micro-bubble lodging on a 100×100 μm square area assay region would obscure 20% of the assay region and cause a similar signal level error. Provision of redundancy to minimize these sources of error would tend to defeat benefits of units of this type.

An aspect of invention here is, within the confines of a cassette, using continuous, wide flows with low Reynolds numbers, to create a comparatively large area of bound reagent of approximately equal molar density, to produce a digital image which can be analyzed according to statistical principles to determine the most probable result of the assay in question.

FIGS. 1A and 2A help visualize the relationship of fluid flow to reaction areas of FIGS. 1 and 2.

In FIG. 2A there is a small diffusion distance H, typically less than 50 μm, in which analyte depletion is a concern. To counter this, a comparatively high fluid flow rate, as compared to diffusion travel, is employed. This is used to replenish complexed analyte and consequently achieve attachment of a sufficient amount of label that a high signal to noise ratio can be obtained, to quantify the amount of analyte present in the liquid. This high flow rate as well as the critical geometric tolerance of the design of FIG. 2A directly impacts the diffusion efficiency and consequently the availability of analyte molecules to be complexed on the capture array. In addition, the exact dimensions of the capture area $A_2$ that is exposed to liquid becomes critical to the measurement. For such reasons, coefficients of variation of 20% or above may be obtained with such approaches.

FIG. 1A suggests that a capture area $A_1$ can be supplied by a large source of analyte molecules both to the sides of the ligand receptor spots R and in a greater gap (gap H). Using sufficiently low Reynolds numbers, diffusion is the dominant mode of molecular motion. Because the source of analyte is large relative to capture area, neither flow rate nor geometric tolerances are critical factors. In addition, with flow rate comparatively slow, the occurrence of micro-bubbles and the necessary volume of analyte can be reduced.

Figure 3:
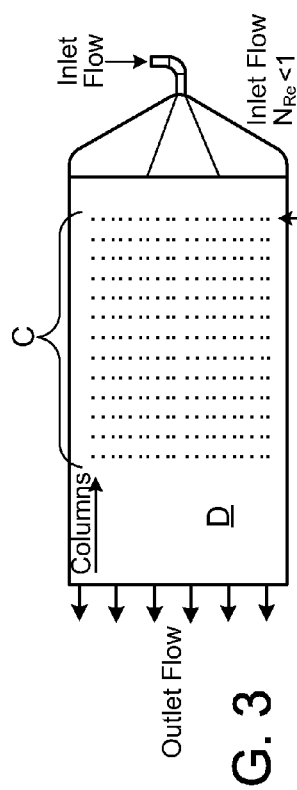
FIG. 3 depicts a capture surface and spotted array of an assay cassette.

In FIG. 3 a capture surface D and spotted array C (see also FIG. 1) are modeled for a disposable cassette.

Figure 3A:
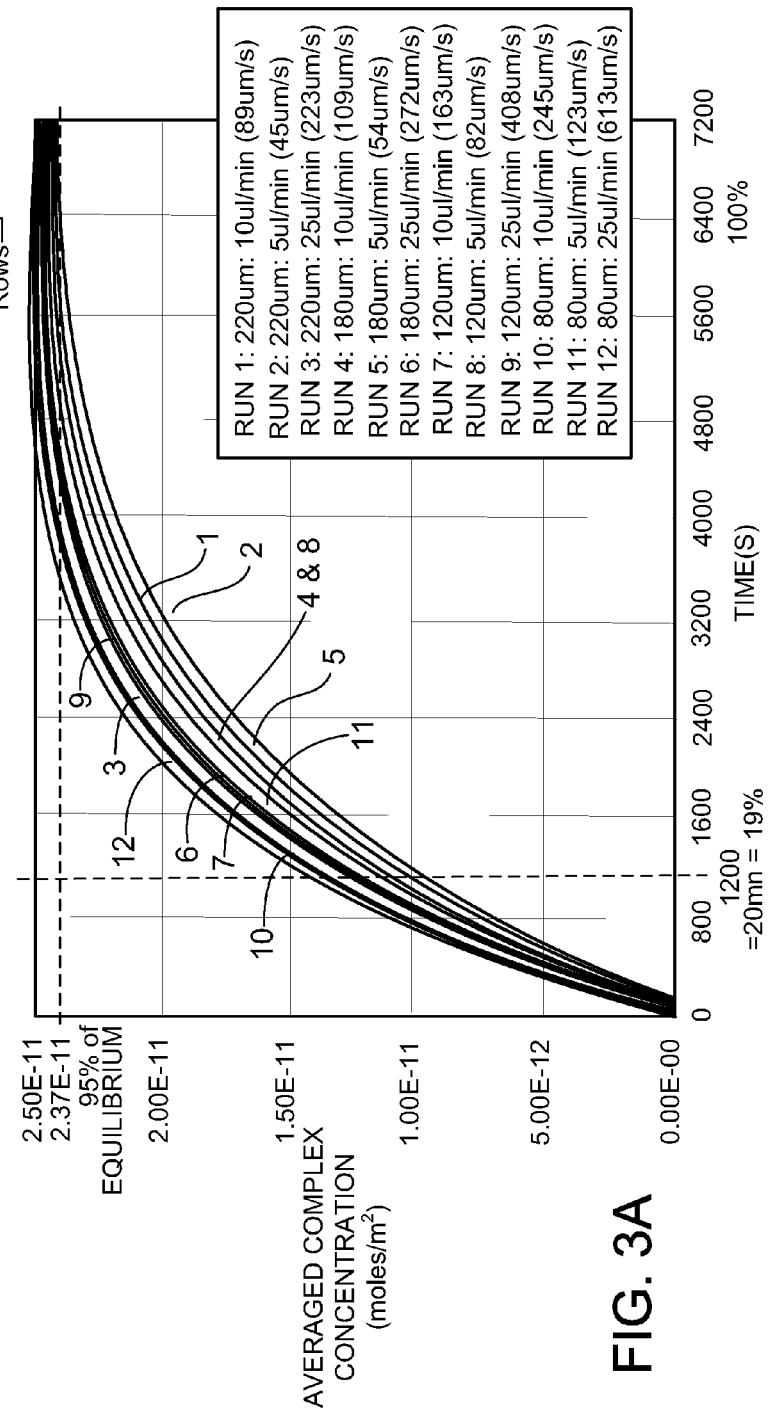
FIG. 3A is a summary plot of a series of computer simulations of the cassette design of FIG. 3, showing the average concentration of ligand receptor-ligand complex on the first row of a 2 dimensional array produced by use of various flow rates and gap heights H, referencing FIG. 1.

FIG. 3A is a plot of a computer simulation of the performance of the system of FIG. 3. It shows a change in the average flow velocity from 45 μm/s to 613 μm/s (a 13.6 ratio) coupled with a gap dimension H change from 220 to 80 μm causes a maximum of only a 50% change in complex concentration in the linear region of the time dependent assay (approximately 10 to 30% of the time required for equilibrium condition, defined as 95% of theoretical equilibrium).

Extrapolation indicates that a 10% change in flow velocity and in gap tolerances would have a worst case consequence of complex concentration varying less than 1%, indicating the worthiness of the general system design of FIG. 3.

In preferred cases, all liquids employed in an assay are stored on board an assay cassette, and out of concern for keeping the liquids on board the cassette to be of small volume, the flow in the reaction chamber has $N_{Re}$ less than about $1 \times 10^{-1}$, preferably between about $1 \times 10^{-1}$ and $5 \times 10^{-3}$, and the gap H is maintained between about 80 and 200 micron. For instance, in one preferred embodiment, employing the design of FIGS. 6 and 7 constructed for a sandwich assay, to be described, employing 2 ml of buffer liquid in the pouch 12, and adapted to receive 0.2 ml of liquid sample, with gap H of 0.1 mm (100 micron) at the reaction chamber, the flow through the chamber may be approximately uniform and have $N_{Re}$ of about $2.7 \times 10^{-2}$. This specific embodiment is considered to be another important aspect of invention.

Besides being of importance in their own right, the principles of FIGS. 1, 1A, 3, and 3A when combined with a gas bubble removal system on the cassette itself, (see FIG. 4) leads to many advantages.

As previously mentioned, gas micro-bubbles can be produced by liquid temperature change, as well as by atmospheric pressure change and localized liquid pressure change, as liquids encounter sharp edges, space discontinuities, or variation of surface properties such as surface roughness or different surface tension properties. We have realized, that in the context of assay cassettes, the generation of gas micro-bubbles has heretofore not been adequately recognized or taken into account. Assay cassette systems employing the concept of FIG. 4 overcome these difficulties, and enable performance of complex assays, with all liquid confined within the cassette, without need for expert personnel.

In many circumstance, prior to use, it is desirable to store a cassette with its liquids on board under refrigeration or under ambient conditions. By use of the principle of FIG. 4, the cassette may be brought to standard temperature, e.g. to living body temperature for biological assays, and despite release of gas micro-bubbles, very good results can still be obtained. Likewise, economical and reliable pumping, valving and liquefication actions, that may tend to produce detrimental gas micro-bubbles, can all be accommodated.

Figure 4:
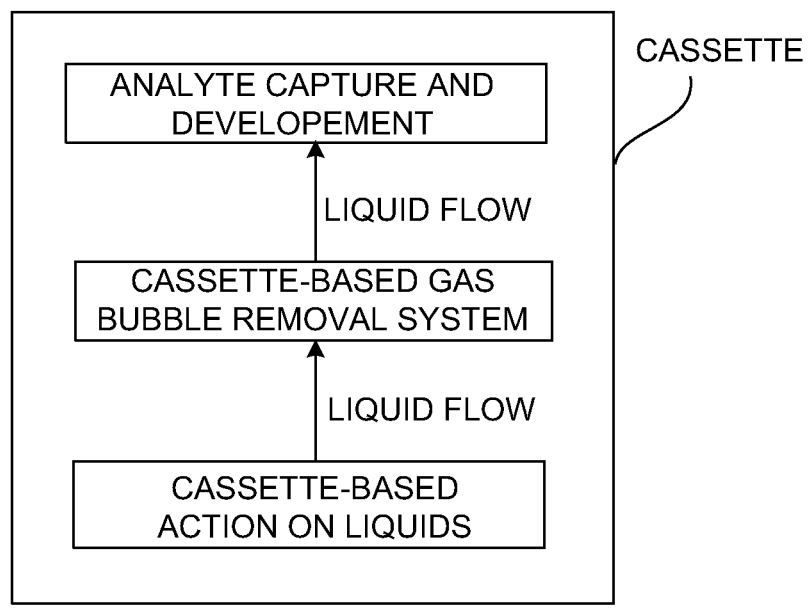
Figure 5:
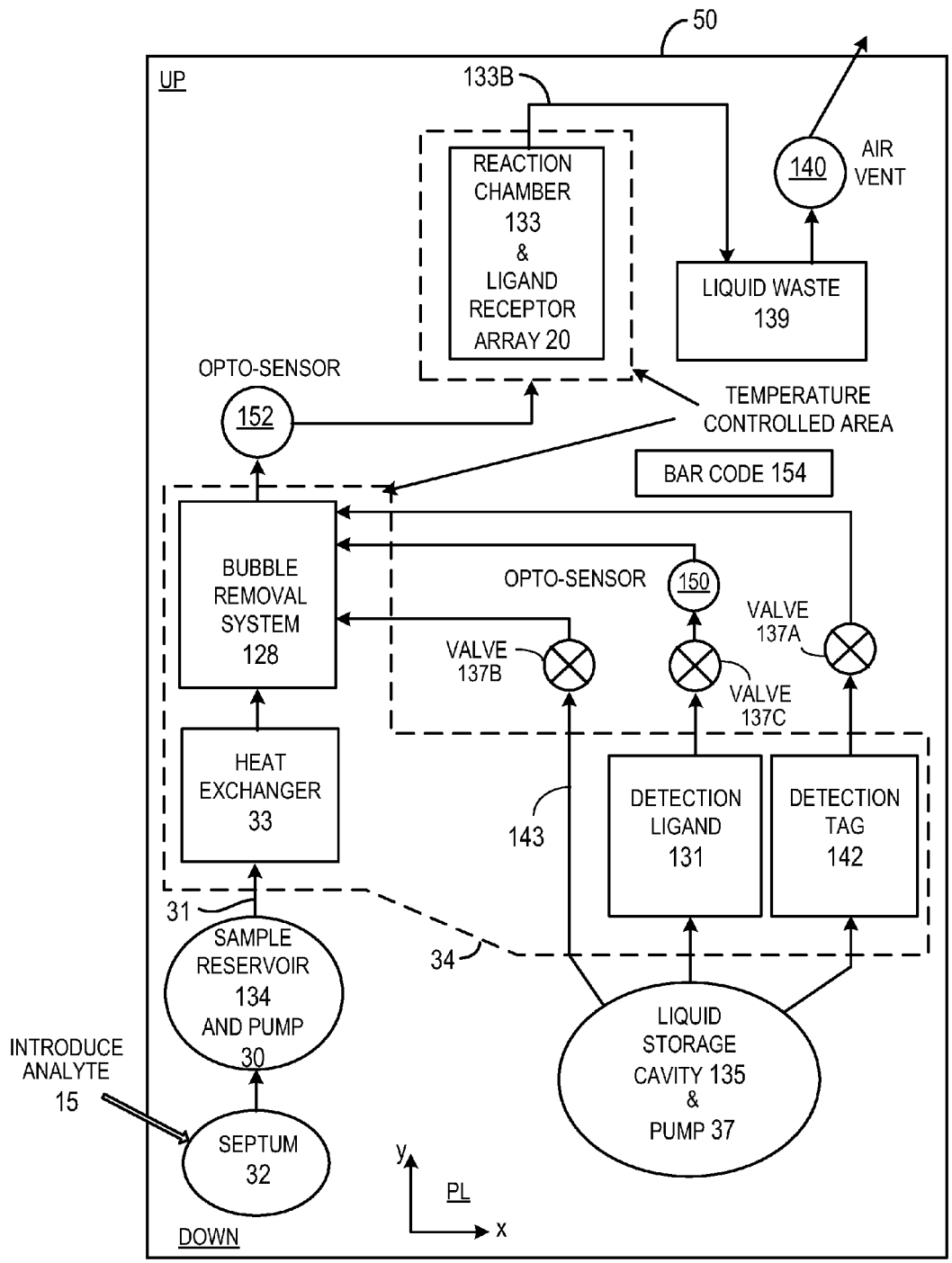
FIG. 5 is a diagram of a disposable cassette with activatable components to perform an immunoassay of sandwich type.

Various kinds of gas bubble removal systems, developed in other fields such as for liquid jet printing and diesel fuel systems may be employed in the embodiments of FIG. 4 or FIG. 5 (see bubble removal system indicated generically at 128 in FIG. 5). Examples include the use of diffusion membranes that are permeable to gas but not to liquid and use of the principle of a capillary gradient transverse to an axis of capillary transport to guide gas bubbles in a direction different from the transport direction of the liquid, as shown in U.S. Pat. No. 6,682,186, incorporated herein by reference in respect to the gas bubble removal technique.

Figure 4A:
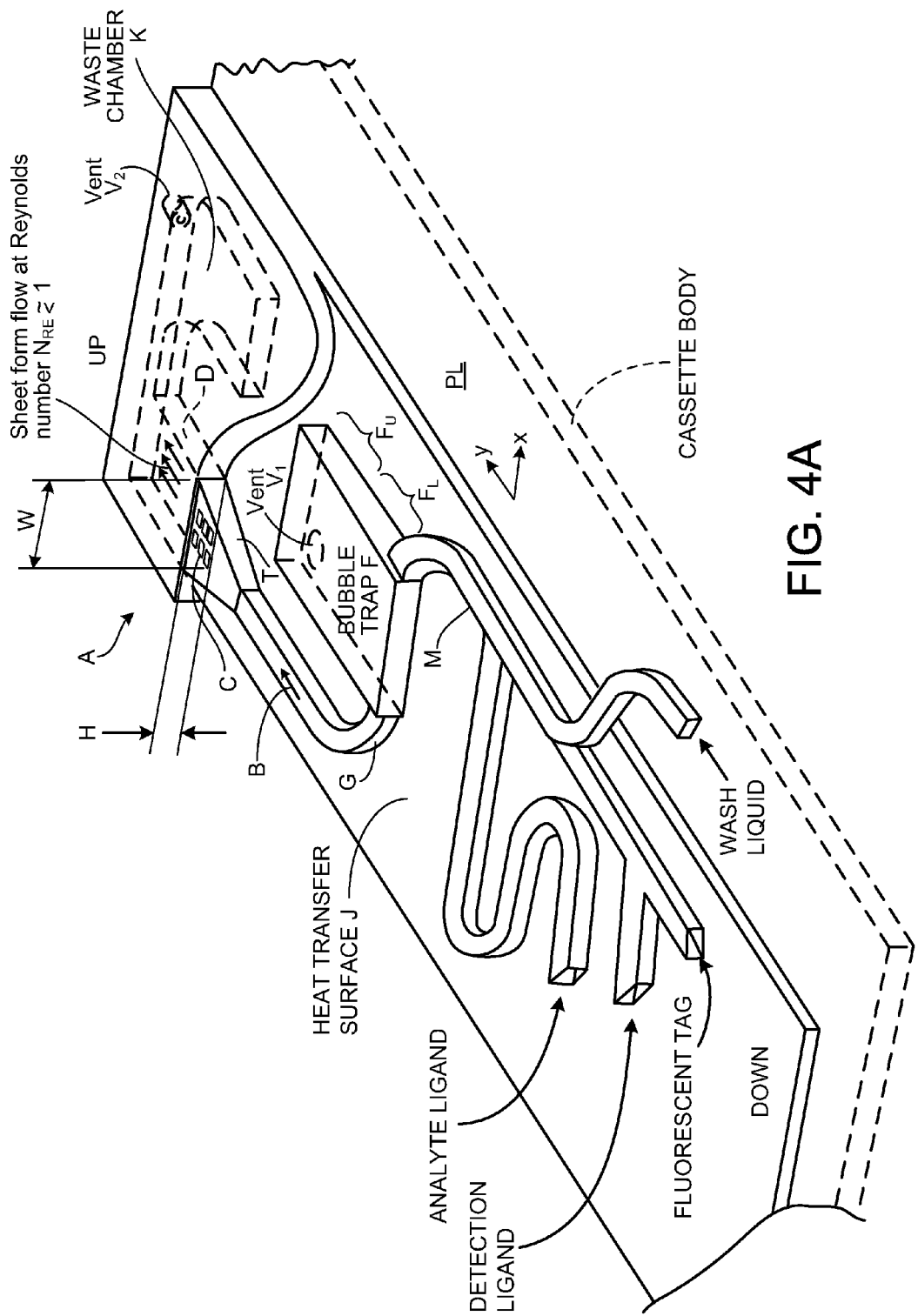
FIG. 4A depicts one preferred embodiment of it.

However, for reliability and ease of implementation using simple features molded in plastic, a flow-through buoyancy chamber is presently preferred. Referring to FIG. 4A, a complex immunoassay is performed on a cassette in which the concepts of FIGS. 1, 1A, 3 and 3A are combined with the concept of FIG. 4, and implemented with a flow-through buoyancy chamber, (in FIG. 4A, "Bubble Trap".) A preferred form of bubble trap shown at 130 in FIG. 6 will later be described in detail in reference to FIGS. 10 and 10A.

Referring to FIG. 4A, a common flow path M is provided for successive continuous, timed flows of analyte ligand, detection ligand and fluorescent tag. In this case, wash liquid also flows through passage M. Passage M directs the flow through a lower portion $F_L$ of a buoyancy chamber F ("Bubble Trap"). At least the lower portion $F_L$ of chamber F constantly contains liquid. With laminar flow through this portion of the chamber, each increment of liquid flow is exposed for a sufficient period (preferably between 1 and 5 seconds) that micro-bubbles rise toward the upper portion $F_U$ of the Bubble Trap under buoyancy force attributable to the much lower density of gas micro-bubbles than the liquid which displaces it. Thus by gravity effect, the micro-bubbles are forced to leave the flow and rise to upper portions of chamber F. An outlet passage G guides the exiting bubble-free laminar flow through a flow transition section T where the liquid flow spreads to a sheet-form flow over the capture surface D. It spreads e.g. from a flow cross-section of about 0.25 mm$^2$ or less, to a flow cross-section of at least 0.75 mm$^2$.

Preceding the buoyancy chamber, the liquid has been subjected to actions appropriate to the assay being performed. In FIG. 4A heating is the action illustrated. As shown, three liquids: analyte ligand, detection ligand and fluorescent tag flow over the heat transfer surface J. Each liquid can be brought to approximately assay temperature preceding the buoyancy chamber. Gas micro-bubbles produced due to reduced gas solubility with increased temperature can thus be removed. For simplicity of design, the wash liquid may likewise transit the path through the bubble chamber, albeit presence of gas micro-bubbles at wash stage may be of no consequence.

According to the general principle of FIG. 4A, one or more of the liquids for the assay may originate from exterior of the cassette. Another aspect of invention, however, is the possibility, owing to the slow flow characteristics of the preferred system, that all liquids, may be stored in suitable quantity on board the cassette, as in FIG. 6.

Another feature of the design of FIG. 4A is waste chamber system K, sized to receive and contain all waste liquids from the assay. In this design the components of the assay are in a generally planar format. In operation the plane is inclined to the horizontal, as indicated by "up" and "down". Besides orienting the buoyancy chamber above the liquid flow path, it enables uniform upward sheet-form flow over the array C on the capture surface D, and thence, by gravity flow, to the waste system K.

An air vent arrangement $V_1$, at the buoyancy chamber, enables the chamber to be filled with liquid, and air vent $V_2$ at the waste chamber enables air to be expelled from the liquid passage system during initiating phases of the assay. The vents may be obstructed by material that passes air but not liquid. Thus after the performance of the assay, the cassette plane PL defined by coordinates X and Y, may be placed horizontally without escape of the liquid.

Figure 5A:
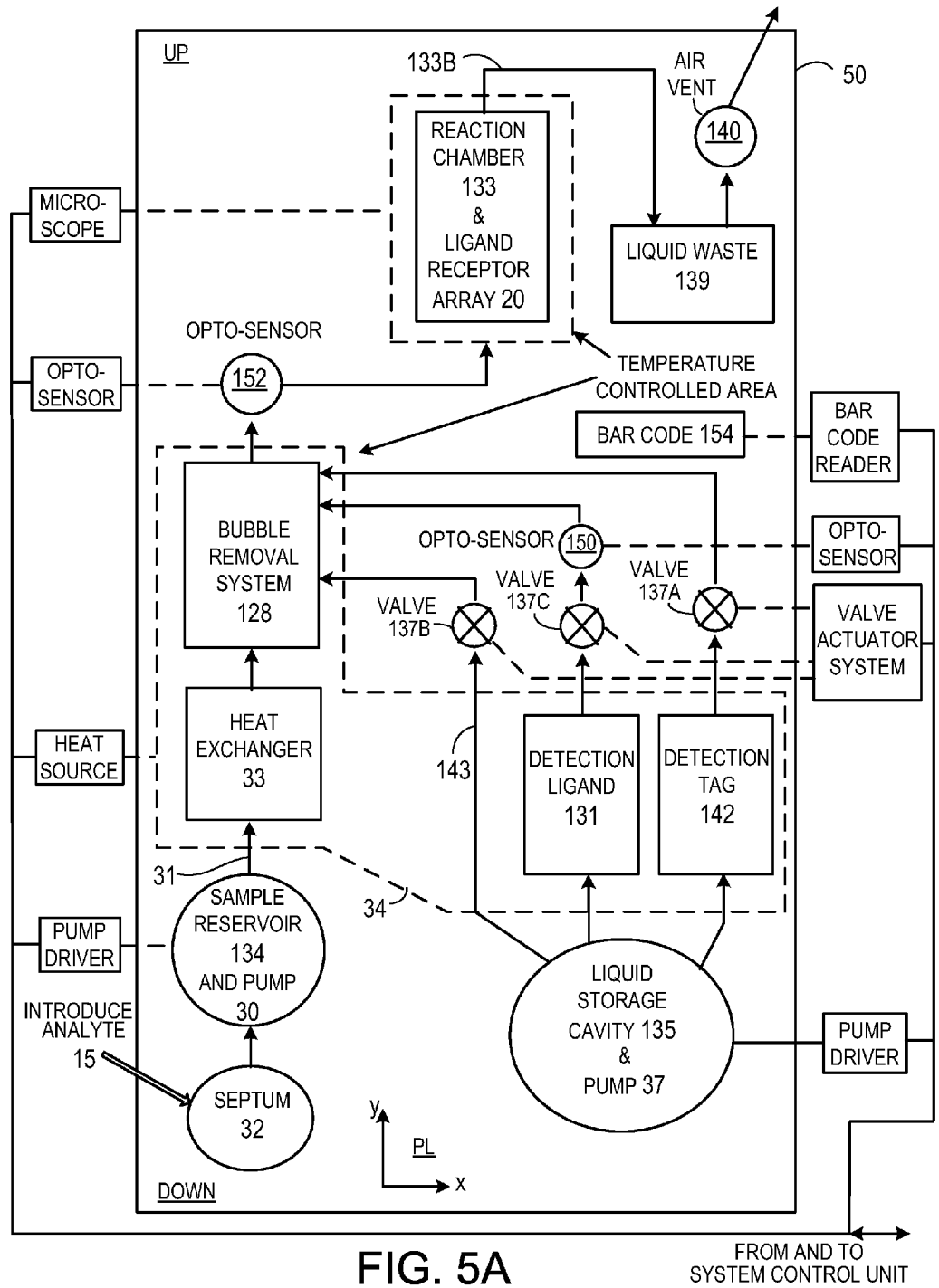
FIG. 5A, similar to FIG. 5, illustrates the relationship of the cassette to external apparatus that activates the components and performs the assay.

Referring to FIGS. 5 and 5A, a scheme embodies the concepts of FIGS. 1, 1A, 3, 3A, and 4, without limitation to type of bubble removal system. Though useful in general for ligand receptor-ligand assays, it is shown adapted for an immunoassay.

In FIGS. 5 and 5A, liquid sample 15 containing the analyte, e.g., blood serum, is introduced through a septum 32 to a sample chamber or reservoir 134 within cassette 50. A displacement pump 30 is associated with sample reservoir 134 for forcing sample 15 through passage 31 into other regions of the system. Heat exchanger 33 heats liquid sample 15 while other parts of heating system 34 heat other liquids for the assay. The heating system may be arranged to bring the liquids to approximately assaying temperature, e.g., physiological temperature, 37° C. For other parts of a liquid containment system, liquid storage cavity or chamber 135 is provided, e.g. for buffer liquid, associated with displacement pump 37.

Pump 37 provides liquids as needed to support the assay, e.g. wash liquid and liquid to chambers 131 and 142 to liquefy, dilute or mix other reagents contained within the body of cassette 50. For an immunoassay, dry detection antibody may be coated on a surface of chamber 131 and dry fluorescent tag coated on a surface of chamber 142.

A bubble removal system 128, shown generically, receives a succession of continuous liquid flows from chambers 134, 131 and 142. It removes micro-bubbles produced previously in the liquids, following which the liquids proceed, in succession, through reaction chamber 133 for exposure to a capture surface carrying array 20 of ligand receptors. The flows are produced by a system of passages controlled by externally driven pumps 30 and 37 and externally activated valves 137A, B and C driven in response to sensors 150 and 152 that sense the arrival of a liquid-air interface in the respective passages.

Waste chamber 139 receives liquid waste from flows through the reaction chamber 133. As indicated by "up" and "down", the plane PL of the cassette is oriented at a substantial angle to horizontal during use to produce gravity flow from the reaction chamber 133 to waste chamber 139. The waste chamber is vented at 140 and the upward flow arrangement of the passage system to the waste outlet enables air in the system to be expelled by action of the displacement pumps 30 and 37 prior to initiation of the assay.

FIG. 5A illustrates the functional relation between features of the cassette and features of external apparatus.

Figure 8A:
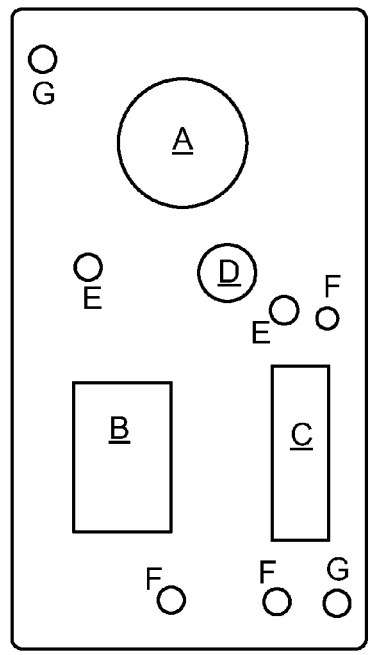
FIG. 8A is a plan view of the interface of the unit with the face side of the cassette of FIG. 6.
Figure 8:
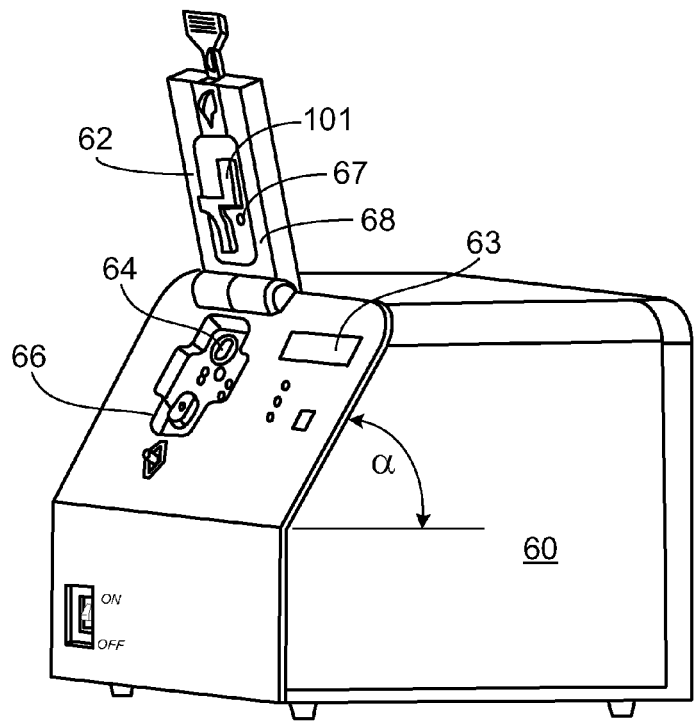
FIG. 8 is an isometric view of a system control unit which incorporates a reading capability.

FIGS. 8 and 8A show a system control unit 60. In this case it incorporates all external functional components. Alternatively, the components can be in separate units under electronic control. Control unit 60 includes system display 63 and a receptacle 66 for the cassette 50. The surfaces of the receptacle dispose the planar cassette at a substantial angle $\alpha$ to horizontal, here 60°, at which it is latched into place. Referring to FIG. 8E, two stepper motor linear actuators 70 (one shown in the diagram) operate the two diaphragm pumps 30 and 37. Three valve actuators 71 (one shown in the diagram) operate the three active valves of the cassette. The progress, performance, and results of the assay can be observed and monitored by system display 63 or by the monitor of an associated computer. After the reaction is complete and all measurements have been read, cassette 50 can be removed and discarded.

Cassette

Figure 6:
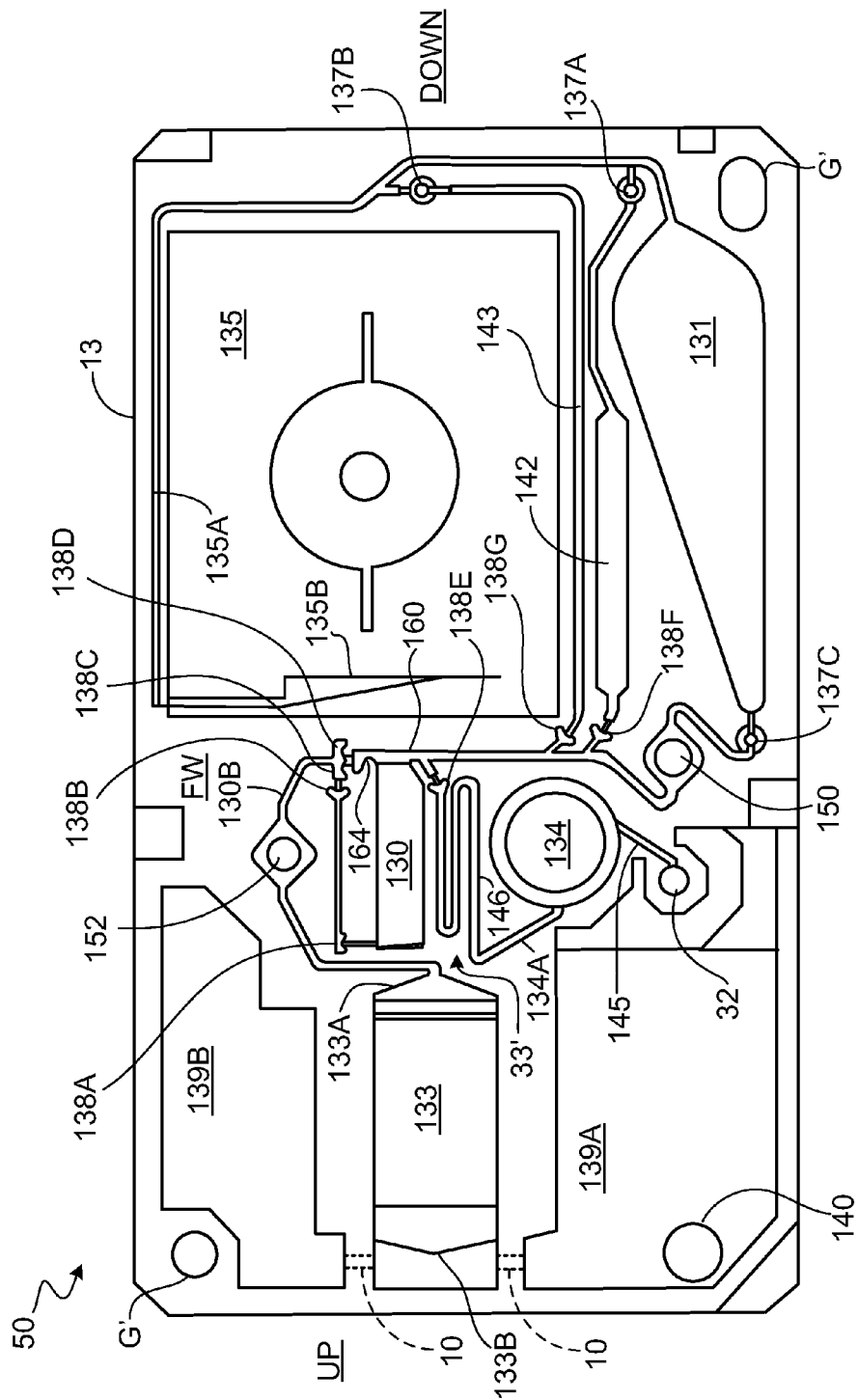
FIG. 6 is a plan view of the interior of the face side of a presently preferred embodiment of the cassette concept of FIG. 5, in this case employing a buoyancy chamber as a preferred bubble removal system.

One preferred implementation of the cassette and control system of FIGS. 5 and 5A is shown in FIGS. 6-15. It employs a bubble removal system based on the buoyancy principle illustrated in FIG. 4A. FIG. 6 is a plan view of the face side of molded body (base) 13 of cassette 50 while FIG. 7 is a perspective, exploded view of the cassette assembly. The assembly comprises cover 1, double-sided adhesive sheet 3, elastic membrane 7, double-sided adhesive sheet 8 and a liquid-containing pouch 12 in the sequence of their assembly to base 13. Additional components of the assembly include clear window 5 for the reaction chamber, mirrors 11A and 11B and clear windows 6A and 6B for optical sensing stations 150 and 152 for detection of liquid-air interfaces in the passages, septum member 137 and its retainer 136 for receiving liquid sample, vent plug 9 for the waste system and closure panel 14 used at the back of the base to complete liquid passages to waste chambers of the cassette. Referring to FIG. 6, the molded plastic body 13 is configured to define all of the liquid storage and passage system. These include septum receptacle 32, sample reservoir 134, liquid chamber 135, first dry reagent reservoir 131, second dry reagent reservoir 142, a bubble removal system in the form of a buoyancy bubble trap 130, reaction chamber 133, waste receptacles 139A and B, receptacle 140 for vent plug 9, and communication passages under bridge 10 which together with closure panel 14 join the waste receptacles 139A and B.

Figure 6A:
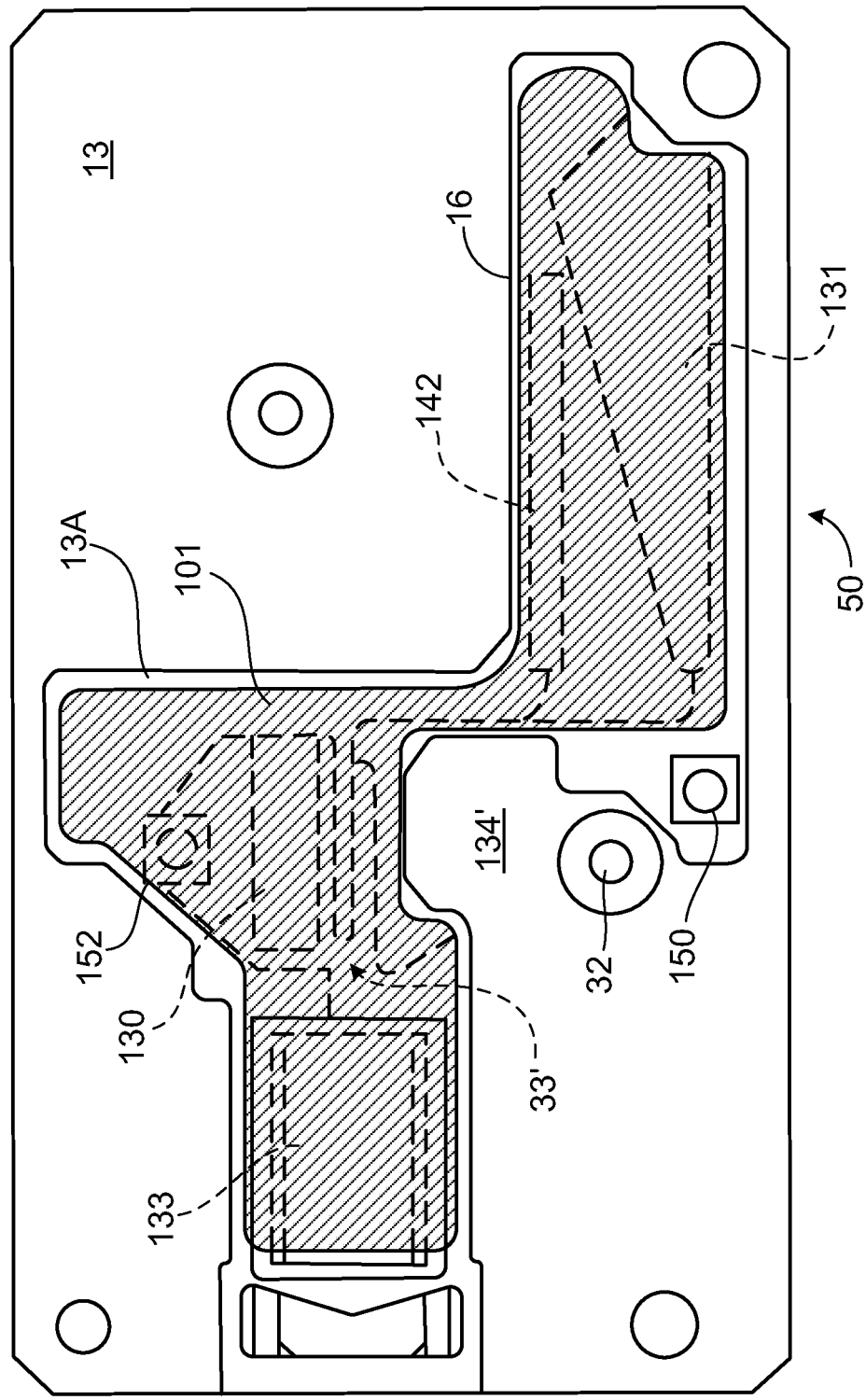
FIG. 6A is a plan view of the exterior of the back side of the cassette, shown in relation to an external heater.
Figure 7A:
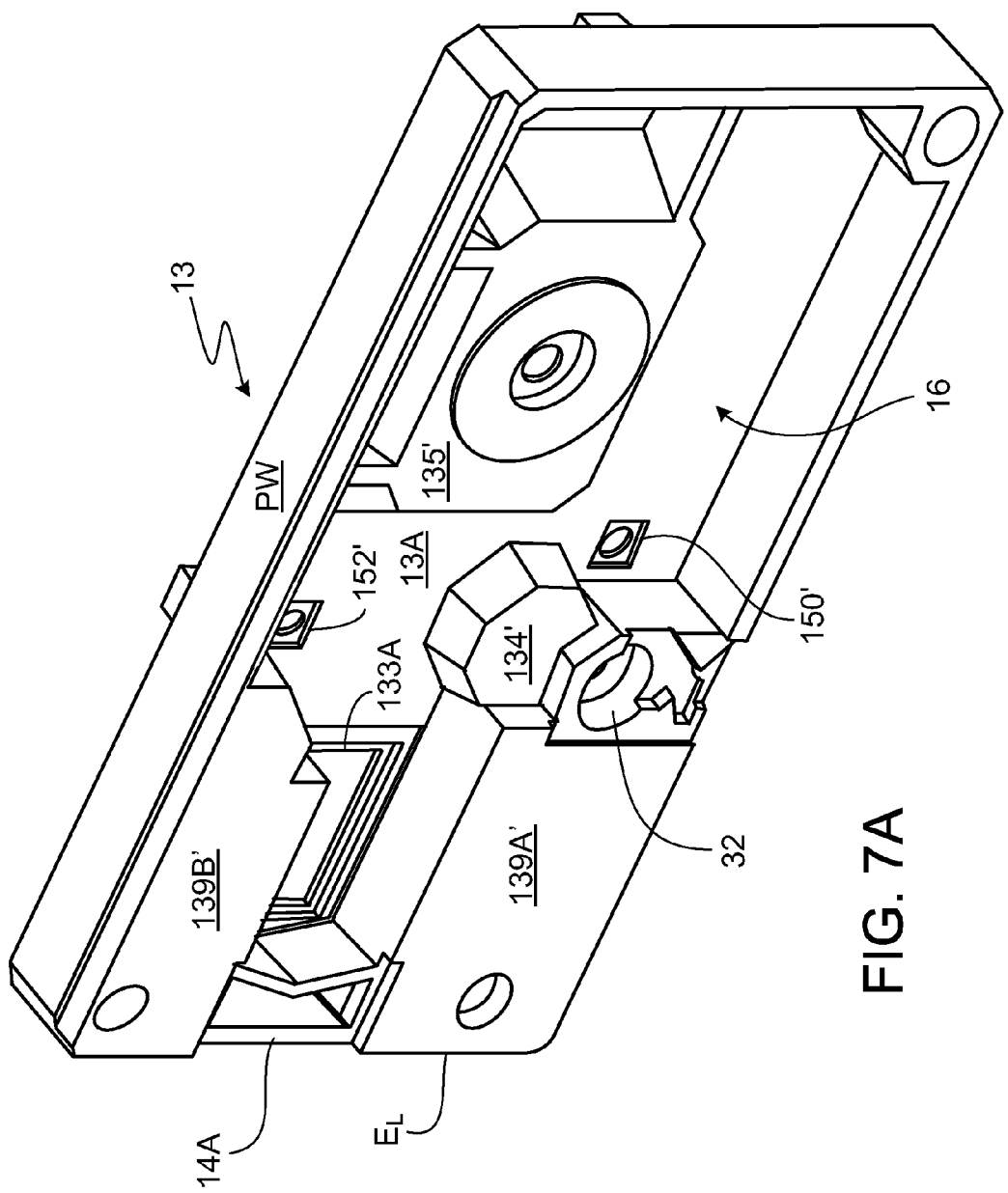
FIG. 7A is an isometric view of the back side of a cassette body of slightly different construction having the same functioning elements as the embodiment of FIGS. 6, 6A and 7.

As suggested in FIG. 7, and see FIG. 7A, liquid chambers 135 and receptacles 139A and 139B have depth corresponding substantially to the overall thickness t of molded body 13. Their bottom walls are generally coplanar with the lower edge $E_L$ of the perimeter wall PW of the cassette, see FIG. 6A, forming part of the backside of the cassette. Septum receptacle 32 (accessed from the backside) and sample reservoir 134 have substantial but less depth. The remainder of the fluidic system is relatively shallow, formed as channels and depressions in a generally planar face wall FW of the cassette that lies substantially aligned with the upper edge $E_U$ of the perimeter wall PW. The backside of face wall FW defines planar bottom surface 13A for receiving the heater as later described with reference to FIGS. 6A and 7A.

The molded body 13 thus defines (in face wall FW) all connecting passages, including a serpentine passage in region 33' for heating pumped liquid sample, the valve seats for valves 137A, B and C, microfluidic capillary burst valves 138A through G, and the optical sensing stations 150 and 152.

Referring to FIGS. 6 and 7, the cassette is formed by attaching cover 1 to base 13 via the intervening adhesive sheets 3 and 8 and the membrane 7. When assembled, cassette 50 has a flow network of interconnected cavities and channels for liquids of the assay, closed by over-lying adhesive sheet 8. Integral portions of the elastic membrane respectively define displaceable pump diaphragms over chambers 134 and 135, valve diaphragms over valve seats 138A, B and C, and an elastically expansible wall over one of the liquefying chambers 131. The cover 1 is formed of relatively rigid plastic and has break-away portions 1A, 1B that overlie the sample and liquid chambers, 134, 135, to act as heads of diaphragm-actuating pistons. Sample chamber 134 is assembled as a pump 30 when double-sided adhesive sheet 8 bonds a region of elastic membrane 7 to base 13 and double-sided adhesive sheet portion 2 bonds detachable segment 1A of the cover to the elastic membrane, to form a piston head suitable to be driven by an external linear actuator.

Preferably, base 13 is of non-fluorescent, rigid thermoplastic, and can be injection molded. Flow of liquid in the channels is favored by preparing base 13 with material that is hydrophilic, such as glass, Cyclic Olephine Copolymer (COC), polyethylene tetraphtalate glycol (PETG), LEXAN® (General Electric Company Corporation, NY, N.Y.), or a form of polymethyl methacrylate (PMMA) such as, e.g., Plexiglas® (Rohm & Haas Company, Philadelphia, Pa.) or Lucite® (E.I. Du Pont Nemours And Company, Wilmington, Del.).

Preferably, the doubled-sided adhesive sheet 3 or 8 has an adhesive strength in the range of 1300 g/25 cm width. A suitable material is Medical Double Coated Tape #1509, 1510 or 1512 (3M Innovations Co.). It is provided with exterior dimensions generally corresponding with those of the planar molded body 13. Strategically located regions of sheet 8 are removed prior to assembly to provide openings ("windows") to base 13 below. These cut-outs regions form sensor windows 8A and 8B, window 8C to form sample pump 30, window 8D to form liquefying chamber 131, window 8E to form liquid storage pump 37, windows 8F, G and H to form active stop valves and window 81 to form reaction chamber window. Membrane 7, an elastic membrane material, is attached by adhesive of the top side of sheet 8 and forms elastic diaphragms at the pump and valve openings or windows in sheet 8.

Membrane 7 is preferably a sheet-form rubber material, e.g. rubber latex. To be suitable for membrane 7, a material should be capable of being perforated or cut into shapes with clean edges, be lightweight, smooth, capable of stretching without slippage, tear-resistant, high in tensile strength, e.g., tensile strength within the range of 100 psi to 10,000 psi, or 4,000 psi, and have an elongation factor ranging between 200% and 750%. Suitable materials for membrane 7 include, latex sheeting of ~0.006" thickness (Latex Sheeting B-LRS-6, Small Parts Inc., Miami Lakes, Fla.).

The second double-sided adhesive sheet 3 is situated on top of membrane 7. Regions are cut out of sheet 3 prior to assembly over sample reservoir 134, buffer pouch 12 and liquefying chamber 131. Adhesive cut-outs registering with detachable elements 1A and 1B of the cover serve to join those elements to the elastic membrane 7 to form the liquid displacement pistons previously mentioned. Sheet 3 is also suitably configured to provide exterior access to body 13 for actuators for the valves and light paths to and from the sensors.

The cover 1 is attached to the top side of exposed adhesive sheet 3 and is sealable to base 13 by using adhesive, heat, or ultrasonic welding techniques. Preferably, cover 1 is made of a non fluorescent polymer similar to that of base 13 and is preferably black to serve as a light baffle bounding the aperture by which the capture surface is to be optically read. Cover 1 is molded with breakable tab portions T of stress-concentrating configurations to break and release detachable elements 1A and 1B. In this embodiment, over chamber 131, cover 1 has a molded upward impression in its undersurface. The impression corresponds to the shape of liquefying chamber 131 and is of uniform depth. It defines an expansion region for the corresponding portion of the elastic diaphragm 7 to enable increase of the chamber volume 131 during liquefication of dry agent. In another embodiment, cover 1 is a membrane or a film, for example a bonded resilient plastic film. Where it is desired that the user of the cassette device be able to view the interior contents of the device, cover 1 can be transparent in desired regions.

The liquid passage network shown in FIG. 6 is formed by channels molded in body 13, and closed by corresponding areas of the adhesive sheet. The passage network connects all liquid storage chambers to a single inlet 160 to buoyancy chamber 130 (formed also as a depression in face wall FW of body B, as shown, and closed by overlying adhesive sheet 8). Sample flow, when initiated by pump 30 of sample chamber 134, is received by buoyancy chamber 130 from heater labyrinth 33'. Reagents and wash liquids when displaced by pump 37 of liquid storage chamber 135, under valve control, are received via reagent chambers 131 and 142 and wash channel 143. A single outlet 130B transmits liquid flow from the buoyancy chamber via flow transition section 133A to reaction chamber 133.

As shown in FIGS. 6A and 7A, the backside of molded body 13 has cavity 16 coextensive with and extending slightly beyond the shaded region of FIG. 6A (representing external heater 101). Cavity 16 has planar bottom surface 13A formed by the back-side of face wall FW. It underlies those portions of the flow system to be heated. The portions to be heated include: serpentine liquid sample passage 33', reagent chambers 131 and 142, the connecting passage network leading to and including the buoyancy chamber 130, and the further passage to, and including the reaction chamber 133.

The molded body of FIG. 6 has alignment openings $G^1$ to receive alignment pins G of the control unit, see FIG. 8A. Likewise the molded body has a set of space-apart raised reference pedestals for establishing planar alignment of the cassette with reference surfaces of the control unit.

FIG. 7A, further shows the back-side of the cassette body. Portions 135', 139A' and 139B', relating respectively, to liquid chamber 135 and the two waste receptacles 139A and B are coplanar with the lower edge $E_L$ of the perimeter wall PW of the cassette body. Planar bottom surface 13A underlies shallow portions of the fluidic system defined by the opposite side of face wall FW.

Figure 14:
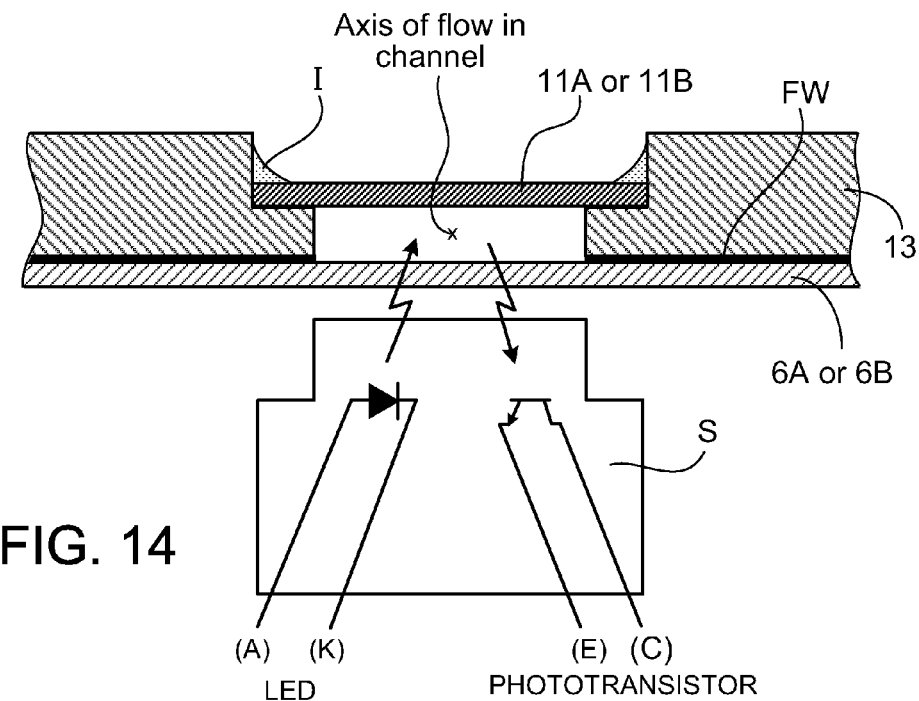
FIG. 14 is a diagram of an optical-sensor employed to sense the arrival of a liquid-air interface in a channel of the cassette.

FIG. 7A also shows mounting receptacles 150', 152', for opto-sensor mirrors 11A and 11B, see FIG. 14; receptacle 14A for closure panel 14 for completing the waste passage to the waste receptacles; and chip receptacle 133A for receiving a support which defines capture surface D, FIGS. 1, 1A, 4A, carrying an array of ligand receptors. Capture surface D forms the bottom of reaction chamber 133 while its opposite side is formed by glass window 5, FIG. 7.

Figure 8B:
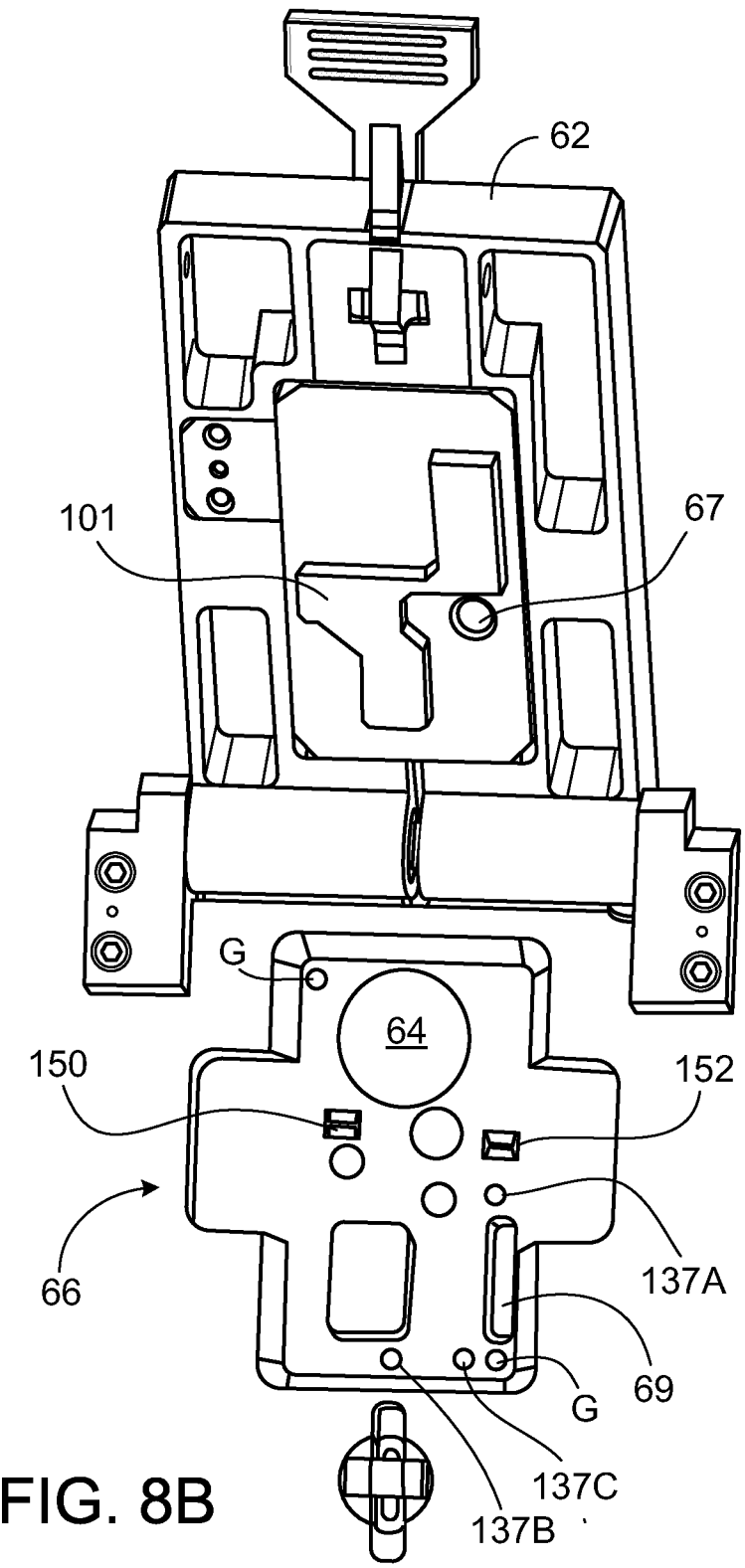
FIG. 8B is a perspective view of interfaces of the control unit for engagement with the cassette.
Figure 8C:
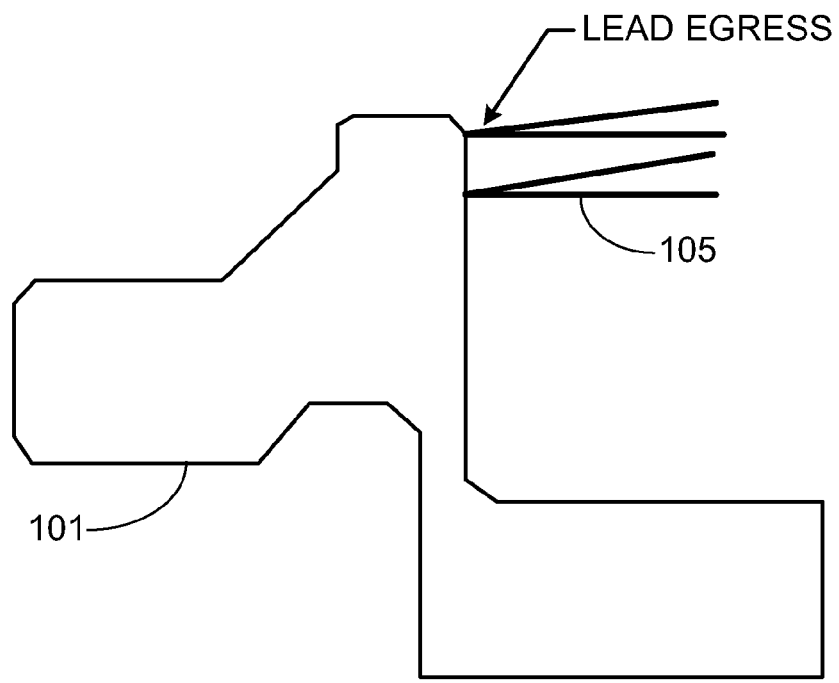
FIGS. 8C and 8D are plan and cross section views showing details of the heater of the control unit.

External heater assembly 101 of FIGS. 6A and 8C, is constructed for face-to-face heat transfer relationship with cassette surface 13A at cavity 16. Assembly 101 is part of control unit 60 of FIG. 8. Under control of a temperature sensor at the reaction chamber 133 it raises the contained liquids to approximately uniform temperature, preferably 37 degree Celsius.

In operation, the substantial angle to horizontal at which cassette 50 is held (angle α, FIG. 8) places waste vent 9 at the top of the cassette. The cassette may be inserted into control unit 60 and the cover 62 closed, after which liquid sample is injected into reservoir 134. The fluid reagent pouch 12 in chamber 135 is pierced, e.g., by an internal or an external lancet, to release the liquid. By pumping of liquid, air within the cassette is expelled through the reaction chamber 133, and waste receptacle 139, to exit through vent filter 9. All stages of operation are controlled electronically e.g., by system controller 60.

Operation and further details, of the embodiment of FIGS. 6 and 7 will now be described for the example of a multiplexed immunoassay according to FIG. 17 in which the analyte is an antigen ligand and the ligand receptor (capture agent) is an antibody.

Referring to FIGS. 6 and 8E, and to the general system of FIGS. 5 and 5A, performance of an assay is initiated by system controller 60 closing label valve 137A and wash valve 137B, and activating pump 37 to displace fluid from reservoir 135. With the left side of the cassette of FIG. 6 elevated, air and then liquid is displaced through intake manifold 135b located at the high side of storage chamber 135. Fluids from reservoir 135 travel into first dry reagent reservoir 131 until liquid displaces all air from the reservoir. The liquid liquefies dry reagent in reservoir 131, e.g. detection antibody, reservoir 131 thus serving as a liquefying chamber. Following chamber 131, as liquid reaches the opto-sensor 150 the liquid-air interface is detected. In response, sensor 150 directs the system control unit 60 to close the valve 137C to block further liquid flow. By design, the system may delay valve closing for the time of a few steps of the linear stepper motor to enable advance of liquid sufficient to displace air up to connection with the next branch of the passage system.

Valve 137A is then opened, and pump 37 of chamber 135 is actuated for a predetermined number of steps of the linear stepper motor to fill the second dry reagent reservoir 142 and the discharge passage branch with liquid, thereby expelling any air.

Valve 137A is then closed, valve 137C remaining closed, and wash valve 137B is opened. Pump 37 is operated a predetermined number of steps of the stepper motor to displace air within wash channel 143. Valve 137B then closes.

The sample pump 30 associated with sample chamber 134 displaces air and then sample liquid from the high side of chamber 134, through the heated serpentine passage 33'. This heats the sample liquid to a temperature of approximately 37 C. Movement of liquid into the serpentine passage displaces air ahead of the liquid front.

By continuous pumping; the sample liquid fills the bubble trap 130 so that it will operate properly. The pair of passive micro-fluidic burst valves 138C, 138D, at the outlet 130B of the bubble trap 130, blocks sample liquid from passing until the bubble trap is filled with sample liquid. Air in the bubble trap is displaced through the air vent circuit formed through a pair of passive micro-fluidic burst valves 138A, 138B arranged in opposition. Valve 138A blocks liquid from escaping from the bubble trap 130. Valve 138B blocks liquid from back-filling into the bubble trap 130. Thus air and then liquid is directed toward the reaction chamber 133.

By control of the stepper motor of the linear actuator for sample pump 30, the pump displaces sample at a predetermined rate and program until the sample opto-sensor 152 detects arrival of the liquid-air interface. This is the start event. It triggers control unit 60 to drive the sample pump 30 according to a predetermined rate and duration to transport sample through the reaction chamber 133, as required by the particular assay for which the cassette is being used. Gas micro-bubbles produced by heating the sample, etc., are removed from the sample liquid by the bubble trap 130 before the sample reaches the reaction chamber 133.

Either simultaneously or sequentially, dried reagent within first dry reagent reservoir 131, e.g., a dried coating of detection antibody reagent, is liquefied by oscillatory fluidic agitation. For this, valves 137A, valve 137B and valve 137C remain closed. By repeated forward and backward motion of the associated linear actuator, reagent pump 37 displaces liquid forward and backward. Forward motion causes a predetermined volume of reagent to bulge the elastic membrane covering detection storage chamber 131, while backward motion causes the membrane to contract and liquid to flow backward. Pump 37 is programmed by system control unit 60 to cycle in oscillatory motion a predetermined number of times at predetermined rate and volume. This system enables various modes of agitation. One is by slow filling and emptying e.g. at a frequency under 10 Hz. Another mode is in short steps with a frequency up to 10 Kz. (See Masterangelo Carlos & al., "*Simulation of Interfacial Dynamics of Time-Dependent Converging Flow in Microchannels*", *Proc. SPIE,* 4560:108-116 (2002).

Sample liquid is caused to flow through the reaction chamber for a pre-established duration, as determined by the control program, and pump 30 is then stopped. Detection antibody valve 137C is then opened, and pump 37 activated to force now-liquefied and heated detection antibody, that had been stored in the dry detection antibody reservoir 131, through bubble trap 130 and into the reaction chamber 133. The liquid bearing the detection antibody displaces any sample in the reaction chamber 133, and during a continuous flow for a programmed duration, the detection antibodies bind to any analyte bound to capture agents within the reaction chamber. Any detrimental gas micro-bubbles produced by the heating or agitation are removed by the bubble chamber 130.

The fluidic burst valve 138E is intended to block reagent/buffer from entering the serpentine passage 33' only when the passage is dry. This condition occurs when, instead of the procedure described here, it is elected to fill the bubble trap with reagent or buffer liquid rather than serum or analyte.

The dry fluorescent label cavity 142 has previously been filled with buffer liquid and liquefied. At a predetermined time, system controller 60 closes the detection antibody valve 137C and opens the label (tag) valve 137A to change the drive mode of diaphragm pump 37. Further operation of pump 37 now displaces heated liquid from fluorescent label reservoir 142, through the bubble trap 130 and the reaction chamber 133. This enables the label (tag) to bind to the complexed antibodies in the absence of detrimental gas micro-bubbles.

When the final step of the assay proper has been completed, namely binding of label to the detection antibodies (Abd) on the capture surface, the unbound label present in the chamber is washed out to minimize label-induced background signal during later imaging (reading). Therefore, at a predetermined time the system controller closes label valve 137A and opens wash valve 137B. Pump 37 then causes wash liquid to move liquid via the bubble trap into the reaction chamber to accomplish washing. The array capture surface in the reaction chamber is now ready for reading. This may be done in the presence of wash liquid or the reaction chamber may be cleared of liquid by running pump 37 backward to suck liquid from the reaction chamber.

Storage of Materials

The capture antibodies (or other ligand receptors) specific to an application are deposited and adsorbed as groups of spots in a ligand receptor array 20 on a treated surface of thin, solid nitrocellulose film. The film is carried on a glass "biochip" which is contained in the "reaction chamber." (See portions of WO 04/018632A2 (PCT/US03/25685) relating to solid nitrocellulose film of thickness less than 1 micron, and treatment of its surface, hereby incorporated by reference.) Treatment (surface activation) of the film by corona discharge is preferred.

The detection antibodies (Abd) or equivalent are stored as a dried coating on a surface of the detection antibody reservoir 131. Fluorescent label material is stored as a dried coating on a surface of fluorescent tag reservoir 142. The buffer liquid is stored in a fluid-tight "fluid pouch" 12 located in the fluid reagent cavity 135. The sample, after introduction, is stored for the assay in reservoir 134.

Reaction Chamber

The reaction chamber 133 is a tunnel, approximately 9.5 mm wide and 12.5 mm long. It is formed on one side by the biochip capture surface carrying array 20 and on the other side by transparent window 5. The tunnel communicates with the flow transition section 133A and wash discharge 133B at the 9.5 mm dimension, and is closed on the other sides. The array 20 on the biochip surface and the window are spaced apart with an approximately uniform gap between 80 and 300 micron, preferably between about 100 and 200 micron. The backside of the biochip is exposed for contact by the heater and to a temperature sensor embedded in the heater.

Spotted Array

In one preferred embodiment, reaction chamber 133 has dimensions of 9.5 mm×12.5 mm×0.20 mm (200 micron gap) and in another the gap is reduced to 0.10 mm (100 micron). The surface of the solid support used for attachment of capture agent is 6.5 mm×9.5 mm. A typical assay searching for one analyte consists of a number of spots of ligand receptor, preferably spots with diameter between about 50 micron and 500 micron separated by a distance similar to one spot diameter. A typical spot diameter is nominally 150 micron, 300 micron on center.

Figure 16A:
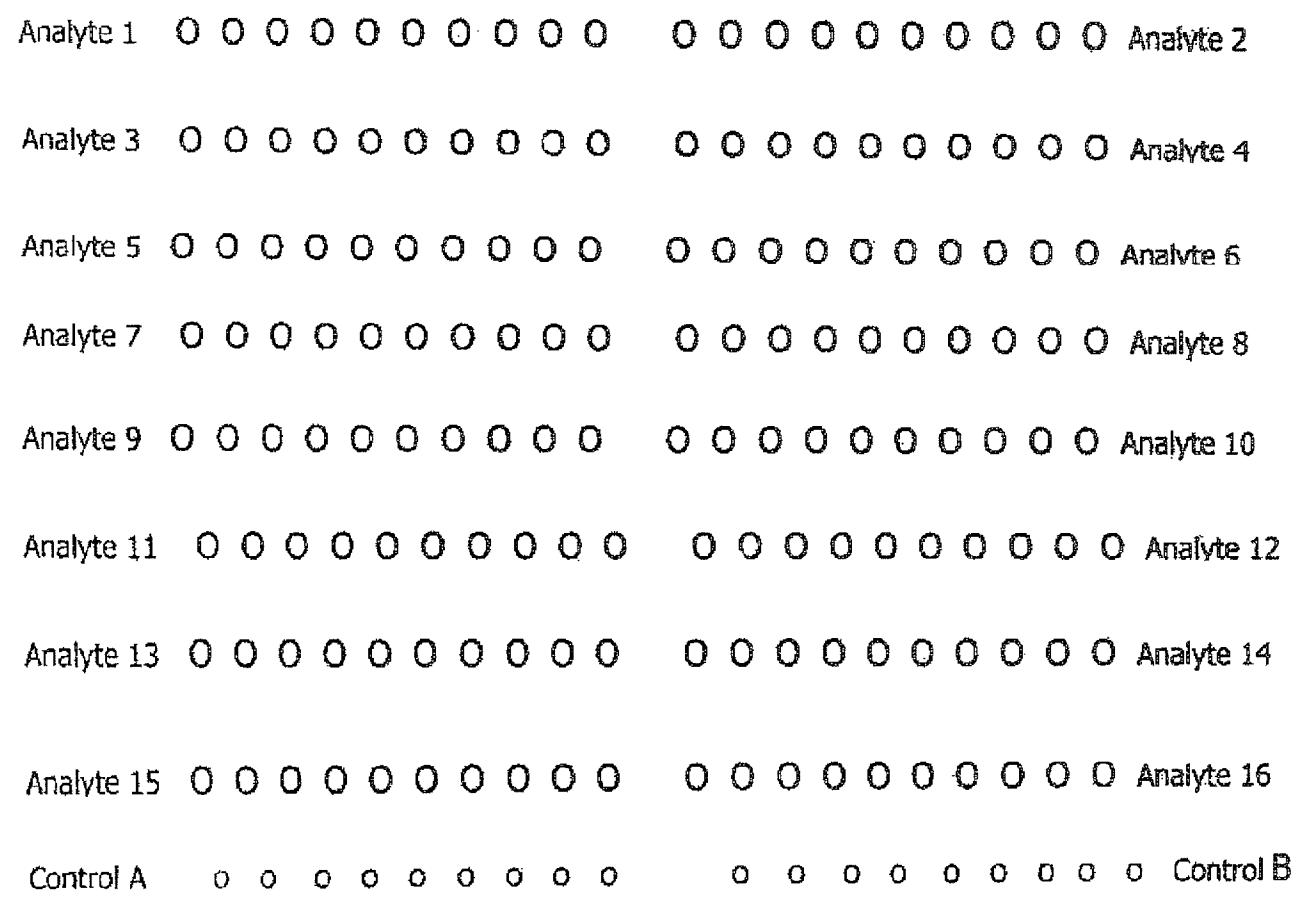

Preferably, referring to FIGS. 16 and 16A, a first row of spots arranged transversely to the direction of flow consists of two regions of 10 adjacent replicate ligand receptor spots 300 micron on center, each group of 10 forming one assay for one ligand, Analyte 1 and Analyte 2.

In FIG. 16, following rows, as the serum (or other sample liquid) flows, are used for signal calibration (see below, "Analysis of Data). These may be spotted with an equal number of spots of ligand (e.g. protein) associated with the adjacent ligand receptor (e.g. capture antibodies) and preferably consisting of known concentration of the ligand. A number of such calibration rows of different concentrations, sufficient to define a calibration curve, e.g. calibration rows 1A-1G, may be used, see FIG. 16, to achieve self-calibration. Preferably, as shown, reference spots in the row are displaced, locating the reference spots between the spots of capture antibodies rather than directly behind (in the direction of flow) to reduce depletion consequences. Similar rows are provided for Analytes 3, 4; 5, 6 and 7, 8. A row of control spots control A and control B is also provided.

In the case of FIG. 16A, intended for use with pre-established calibration curves, most of the capture surface is occupied by rows of replicate analyte spots, Analytes 1-16, concluding with a row of control spots.

In another arrangement alternating rows of ligand receptors for the analyte and pairs of rows of ligand reference spots of two different dilutions may be provided, see FIG. 16B.

Other arrangements are possible.

In a case where only two rows are used for capture and reference and each row has 2 analyte regions, a 12.5 mm length can accommodate 40 rows with spots 300 micron on center and consequently 40 different assays.

Liquid Reservoir

Figure 11:
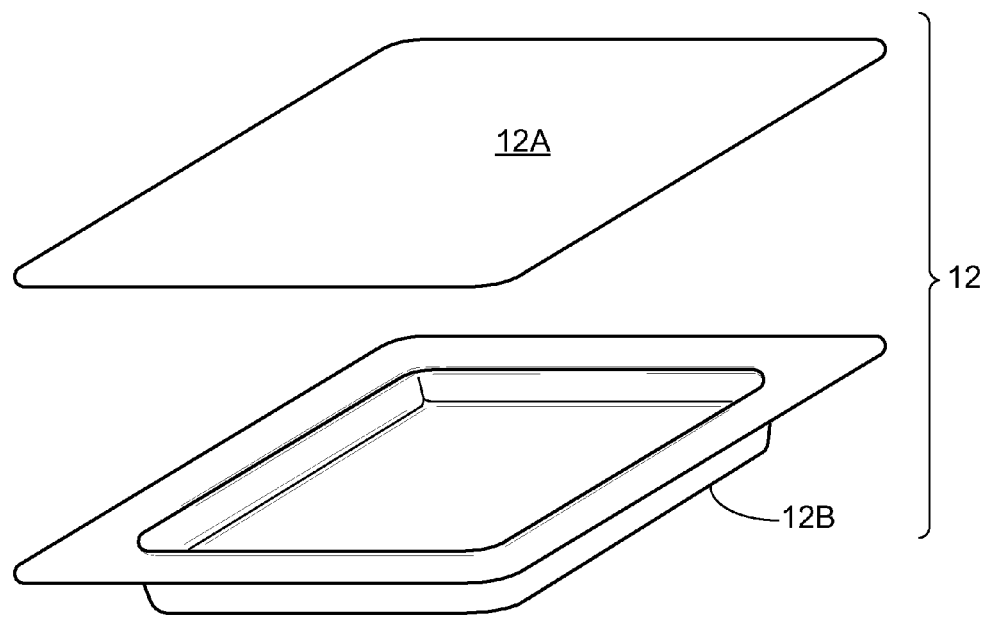
FIG. 11 is an exploded view of the components of a liquid-containing pouch useful with the cassette.

FIG. 11 shows a pouch 12 for liquid for the assay, e.g. buffer liquid for liquefying the reagents and for washing. It is formed from a female "blister" cavity 12B, and covered and sealed with a flat element 12A. Generally, pouch 12 provides a high barrier to moisture, oxygen and light, and holds its shape after being formed into the pouch. Materials suitable are known to those skilled in packaging of biologically sensitive products such as pharmaceuticals, and include, without limitation, cold-form foil (e.g., "Hueck DMF7273" cold-form foil material, Hueck Foil L.L.C., Wall, N.J.) and, e.g., laminated polyester-polyethylene-aluminum foil-CRC-1-polyethylene (Flex-Pak Packaging Products Inc., Batavia Ill.).

Releasing the Liquid from Reservoir

Figure 12:
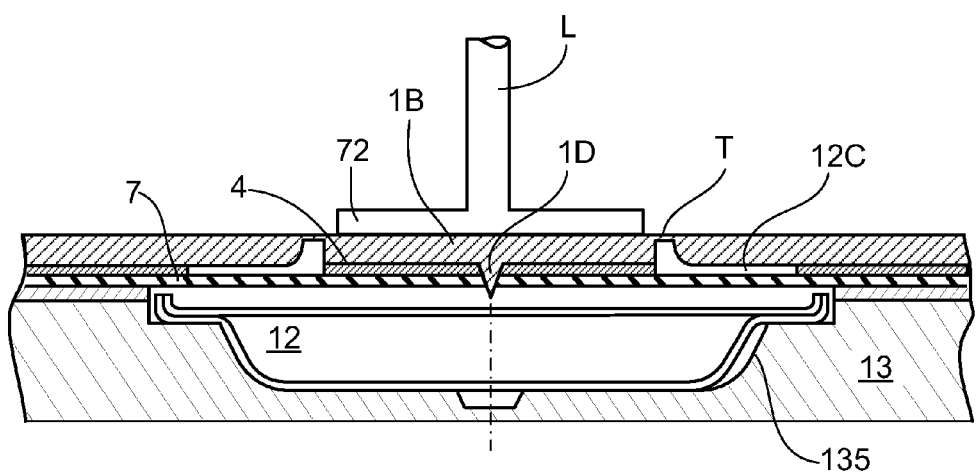
FIG. 12 illustrates puncturing the pouch of FIG. 11 using a projection that protrudes from an elastic diaphragm of the cassette.

FIG. 12 shows pouch 12 in cavity 135 closed by membrane 7 bonded to base 13. It also shows plunger head 1B (a broken-away portion of cover 1) bonded to membrane 7 by an island 4 of double sided adhesive sheet. Plunger head 1B is engaged on its outer surface by end plate 72 on shaft L of linear motor 70 located in system control unit 60. Plunger 1B also has awl (piercing projection) 1D molded as part of the cover, protruding through both double-sided adhesive tape island 4 and elastic membrane 7. Pouch 12 has bent features 12C (not shown on FIG. 11) holding pouch 12 away from awl 1D. Breakaway tabs T hold plunger 1B within cover 1.

At the start of operation, cassette 50 is held in control unit 60 as shown in FIGS. 8 and 8E, in approximately vertical position and valves 137A and valve 137B are closed while valve 137C is opened; linear motor shaft L propels the plunger head 1B which (see FIGS. 12A and 12B) severs tabs T, detaching plunger head 1B from cover 1. The awl (piercing projection) 1D pierces pouch cover 12A such that liquid within pouch 12 escapes into cavity 135 and accumulates at the bottom of cavity 135. As plunger 1B moves forward, pouch 12 is compressed, thus pushing out liquid and reducing the volume of cavity 135. Air within cavity 135 accumulates in collecting manifold 135B in the upper region of cavity 135 (see FIG. 6) and is displaced through duct 135A, reservoir 131 and finally air vent 9 in receptacle 140.

When all air has been expelled, liquid is then displaced through the same channels, as plunger 1B continues to be moved within cavity 135. When liquid reaches opto-sensor 150 the control unit 60 actuates a valve actuator 71 to close valve 137C.

(In an alternate method, not shown here, an externally driven pin may traverse a septum, not shown, to pierce fluid reagent pouch 12 to release liquid from pouch 12 into the pump cavity 135.)

During assembly of cassette 50, pouch 12 is placed in cavity 135. Optionally, the shape of pouch 12 can be configured to fit cavity 135 so as to keep the pouch clear of awl 1D, to prevent premature piercing of the pouch and leakage of fluid. Preferably, the corners 12A of pouch 12, bent upward as shown in FIG. 12, keep the pouch against the closed end of cavity 135 and clear of awl 1D.

Dry Detection Antibody Reservoir

FIG. 6 shows reservoir 131 where the detection antibodies (or other detection ligands) are stored in desiccated condition. During the assembly of the cassette, the region dedicated to receive these reagents is first coated with a "blocker" typically available from Pierce and intended to create a coating that can be readily liquefied to prevent the reagents from adhering to the surface of reservoir 131. The blocker fluid is "painted" or spotted on the surface of the bottom of reservoir 131 and left to air dry. Subsequently a mix in appropriate ratios of all the reagents associated with the capture antibodies (or other ligand receptors) spotted on bio-chip 20 are "painted' in suitable amount over the protected area at the bottom of reservoir 131 and left to air dry. Detection antibodies, for instance, may have a biotin molecule attached to bind to the fluorescent tag bound to a streptavidin molecule in a reaction that is well known to those skilled in the art, see FIG. 17.

Dry Fluorescent Tag Reservoir

FIG. 6 also shows reservoir 142 where the fluorescent tag ("FLR LABEL" of FIG. 17) is stored in a desiccated condition. The fluorescent tag is preferably a Cy3 molecule bound to a streptavidin protein and can be purchased from Amersham, a division of General Electric Co. It is "painted", in suitable amount and concentration to meet the need of the assays, as is well known to those skilled in the art, directly on the surface of reservoir 142 and left to air dry. The dry fluorescent tag is readily liquefied when brought in contact with the liquid buffer.

Liquid Introduction System—Septum

Figure 15:
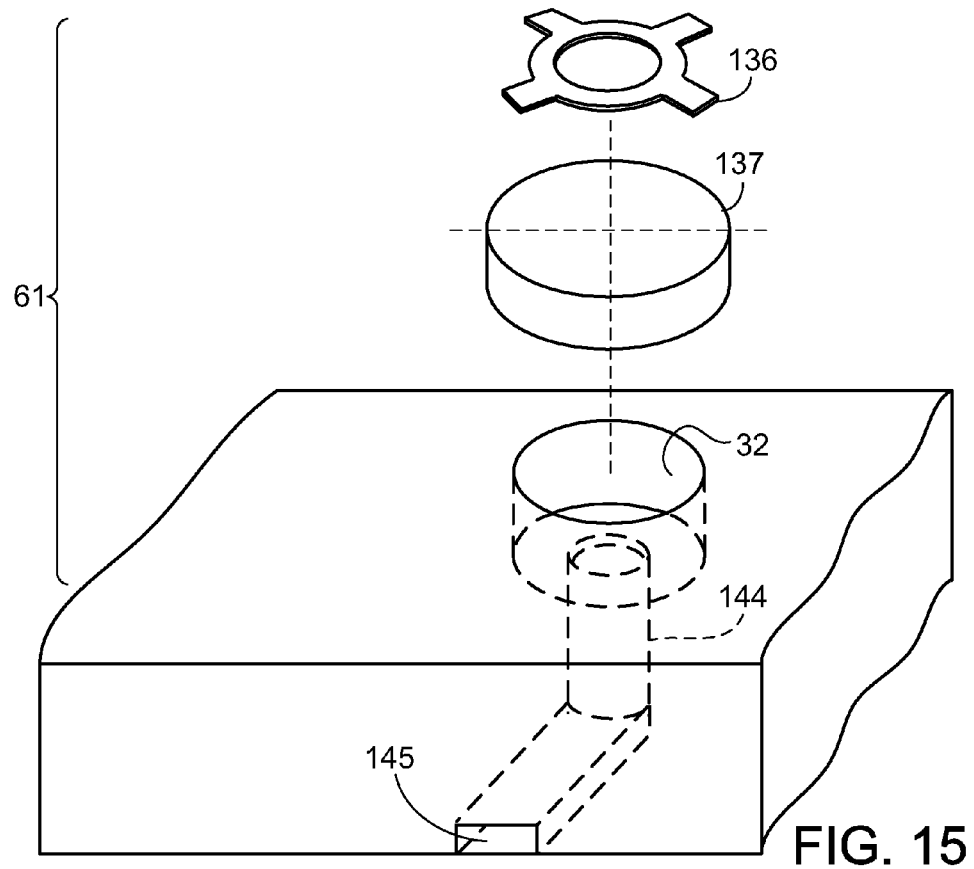
Figure 15A:
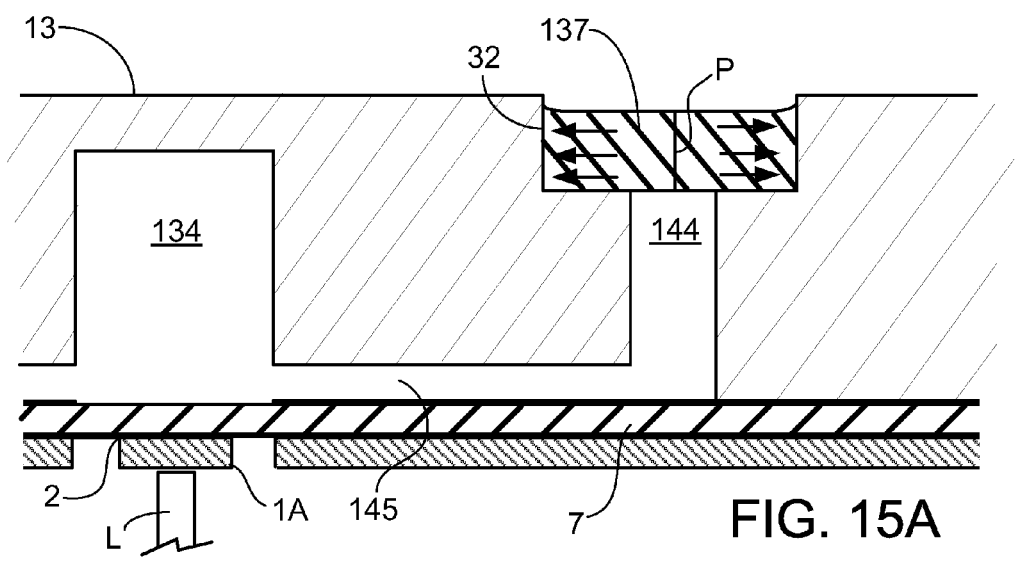

Referring to FIGS. 6 and 7, liquid can be introduced into cassette 50 by use of an external pipette or needle. Alternatively, liquid can be introduced into cassette 50 with a needle that is built into the body of cassette 50 itself. Referring to FIGS. 15 and 15A, in the preferred embodiment described herein, liquid sample (analyte or serum) is introduced into sample chamber 134 through a septum passage system 32 utilizing an external pipette or needle. Those of skill in the art can understand that, in the alternative, liquid sample can be introduced by an internal needle system and/or the liquid can be introduced by an external system of different construction.

FIGS. 15 and 15A show a sample introduction system that includes septum cavity 32, sample injection port 144, and sample injection channel 145. Septum closure assembly 61 at cavity 32 serves as a seal between the exterior of cassette body 13 and sample injection port 144. Septum closure assembly 61 is composed of a compressible septum material 137, that is elastically compressed transversely and tends to expand within the septum cavity 32, as shown by the outward arrows of FIG. 15A. Suitable materials for septum closure 137 are known to those skilled in art, and include, e.g., rubber, preferably a silicone rubber. By way of example, in one embodiment, septum cavity 32 is approximately 3/16 inch diameter, septum closure 137 can be approximately 1/16 inch thick and approximately 1/4 inch diameter when uncompressed, made of silicon rubber of 60 durometer.

Septum clamp 136 serves as a retainer for holding closure 137 in place within cavity 32.

Septum closure 137 is pre-punctured prior to being inserted into septum cavity 32 (pierced, as indicated by axial line P) by a sharp steel needle or other member that has significant sharpness and columnar stiffness. The pre-puncture path P provides a region within closure 137 that is low in resistance, providing a spot through which a relatively blunt or weak (low columnar stiffness) instrument such as a plastic pipette tip can be pushed. Despite pre-puncture of septum closure 61 prior to assembly, fluid does not leak from cassette body 13 because the rubber of septum closure 137, under transverse compression closes path P, ensuring no leakage. The weak spot permits a blunt, relatively large pipette tip to find a point of low resistance, and slide through the septum in liquid-tight manner.

Sample Containment System

FIGS. 6, 7 and FIG. 15A show sample chamber 134 in base 13. It is covered by elastic membrane 7 and connected to septum cavity 32 via duct 145. It is connected to bubble trap 130 via temperature controlled region 33' via duct 146 having its inlet 134A located in the upper region of cavity 134. Serum or analyte is introduced into cavity 134 via the septum 32 following installation of the cassette in a receptacle in control unit 60 in an approximately vertical position. The cassette is held in place with hinged cover 62 as shown in FIG. 8b. Port 67 through cover 62 is aligned with septum 32, to offer direct access to the septum.

Sample Pump

Serum (sample or analyte) pump 30 is formed by molded sample chamber 134, FIGS. 6, 7 and 15A and elastic membrane 7, in conjunction with breakaway plunger head 1A. Head 1A is suitably bonded with double sided adhesive sheet 2, FIG. 7. With the cassette installed in control unit 60, shaft L from the linear motor within control unit 60 engages plunger 1A and drives it downwardly under control determined by the appropriate software.

Retaining tabs T are broken, freeing plunger 1A to move with shaft L. Exit duct 134A from cavity 134 is located at the top of cavity 134 when the cassette is in use position so that first the air within the pump is displaced, followed by liquid (serum or analyte). When pump 30 is activated, liquid sample is propelled into channel 146. Channel 146 makes a number of convolutions as a serpentine passage before connecting to the inlet 160 to bubble trap 130. The heater 101 extends in cavity 16 under channel 146 for heating the sample. Consequently, preceding the bubble trap, the serum or analyte 15 is brought to reaction temperature preferably 37° from room temperature, about 25° or storage temperature, e.g., 4°. This process most commonly causes gas microbubbles to form within the liquid, which are removed as the liquid travels through bubble-trap 130.

Reagent Pump

The reagent pump 37 (for propelling buffer or reagent) is composed of elements incorporated in cassette 50 and elements incorporated in control unit 60. The elements within cassette 50 are the chamber 135, the liquid holding pouch 12, the elastic membrane 7 and the detachable piston head 1B. Incorporated in control unit 60 is the linear stepper motor 70, its motor shaft L, FIG. 8E terminated with a plate 72. One of the functions of plate 72 is to spread actuating force sufficiently to ensure that all breakable tab connections T, holding piston head 1B to cover 1, break to free piston head 1B.

In operation, control unit 60 directs linear motor 70 to drive piston head 1B, breaking it free from cover 1, see FIGS. 12A, 12B. As piston head 1B moves downwardly, it reduces the available volume within chamber 135. Air is expelled via a channel in the upper region of cavity 135 into manifold 135B. In the same time, awl 1D, protruding through the diaphragm 7, penetrates and pierces pouch cover 12A so that liquid flows to the lower region of cavity 135.

The control unit 60 directs the linear motor further. Air is displaced by the pouch liquid and is expelled. When all air has been expelled with piston movement, liquid is then pushed out through the same manifold and channel.

Cassette 50 may be stored at low temperature and taken out as needed. The liquid in the pouch, warmed e.g. to 37°, contains microbubbles which are removed by passage of the liquid through bubble chamber 130.

Temperature Controller & Heater

It is necessary to perform the assay at a known temperature because the complexing efficiency of a sandwich assay is strongly influenced by the rate of diffusion of ligand molecule within its carrier liquid, which itself is a strong function of temperature. Prior to use, normally the cassette as well as serum are kept at room temperature or below. For heating to the desired reaction temperature, preferably 37°, the heating element 101 is an integral part of the control unit 60. When cassette 50 is installed in receptacle 66, and hinged cover 62 is closed, heating element 101, carried on cover 62, nests within cavity 16 in the back of the cassette 50, and engages surface 13A, see FIG. 6A. Heat passes through thin wall regions of the cassette to heat all liquids that interact during the assay.

Figure 8D:
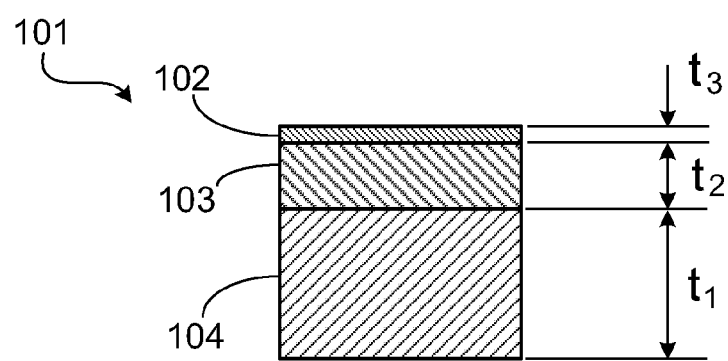
Figure 8F:
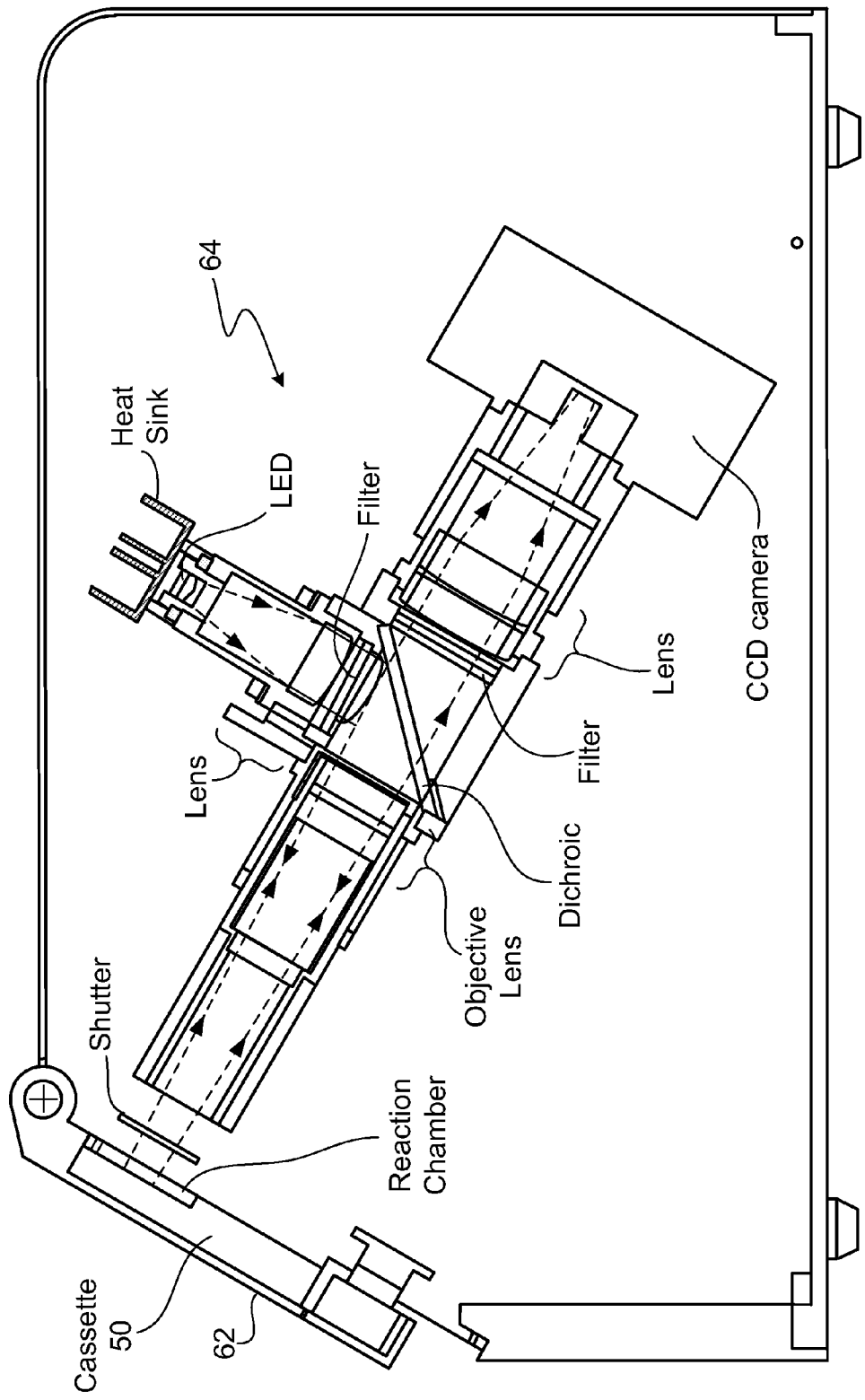
FIG. 8F is a similar cut-away view of the reader system within the control unit.

Referring to FIGS. 8C and 8D, the heater 101 comprises a thin, flexible sheet-form heater element 102 manufactured by Minco Co. to fit cavity 16 at the back of the cassette body 13. It is mounted on a low durometer (60 durometer) silicone rubber foam backing 103 and floating planar rigid support 104. The planar surface of heater 101 can thus be pressed into conformity with planar surface 13A at the bottom of cavity 16, and the backside of the biochip at the reaction chamber 133. A temperature sensor incorporated in the heater unit is arranged to sense the temperature of the biochip for control of the heater.

Gas Removal System: Bubble Trap

Figure 10A:
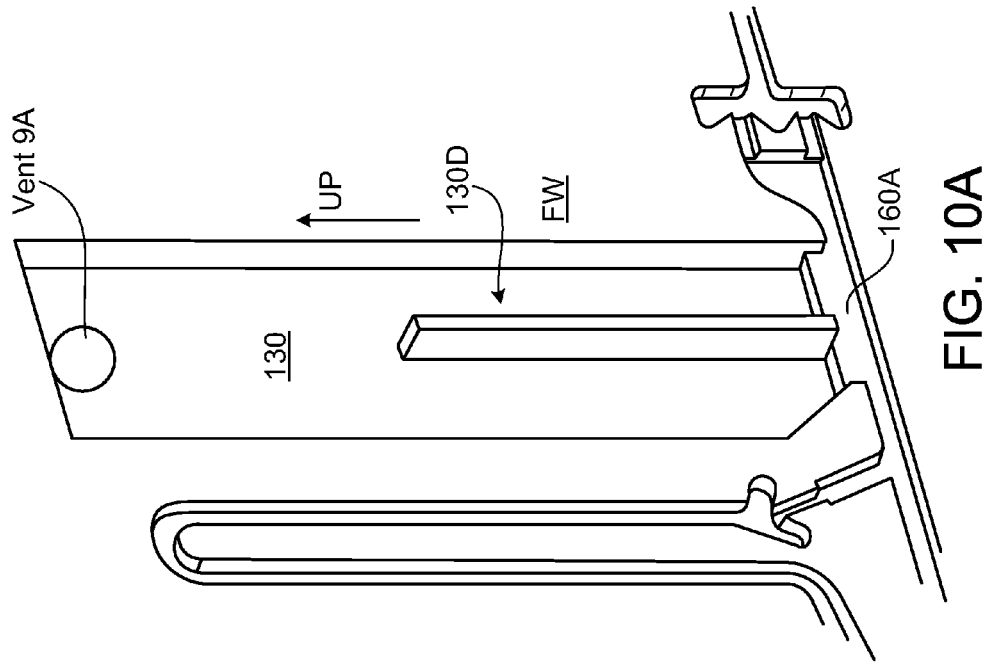
FIGS. 10 and 10A are schematic illustrations of alternate versions of a bubble trap implementation of a bubble removal system of a cassette.
Figure 10:
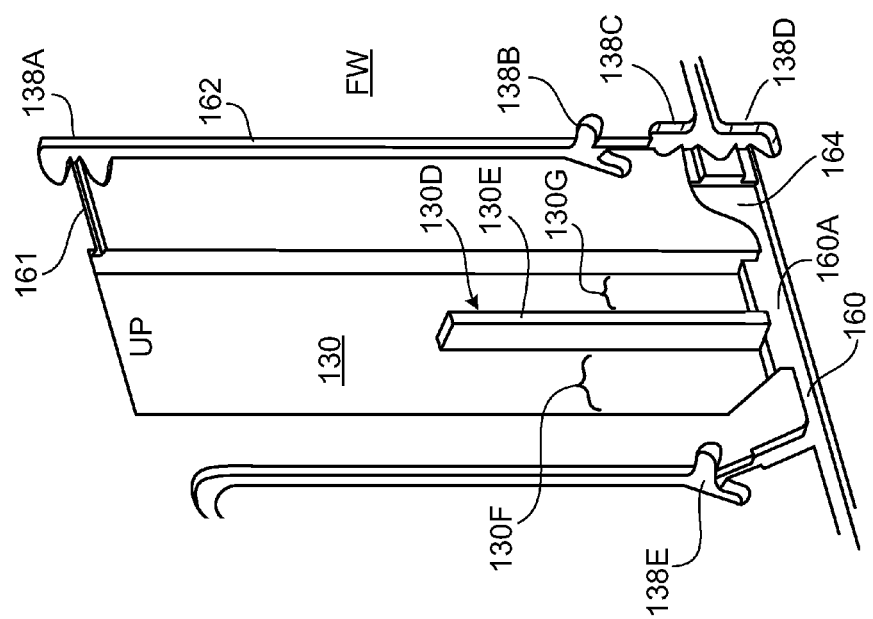

FIG. 10 illustrates an embodiment of the buoyancy bubble trap 130. In the preferred embodiment, sample enters from channel 160 and fills the lower region of the bubble trap 130 but is prevented from proceeding to the reaction chamber 133 as microfluidic capillary burst valves 138C and 138D are designed to conditionally block passage of liquid and burst only when a predetermined back pressure has been reached. Sample (serum or analyte) fills the bubble trap 130 as air is forced up and escapes via microfluidic capillary burst valve 138A and through channel 162, through microfluidic capillary burst valve 138B and out to the reaction chamber 133, the waste receptacle 139 and finally out through the vent passage 140 containing filter 9.

When the bubble trap 130 is filled with liquid, the pressure at exit 164 causes microfluidic capillary burst valves 138C and D to be overcome and serum or analyte proceeds to the serum opto-sensor 152, FIG. 6, from which a signal is sent to system control unit 60 as the liquid-air interface traverses the viewing area. Microfluidic capillary burst valve 138B prevents liquid from entering into channel 162 and nulling the effectiveness of microfluidic capillary burst valve 138A. The system controller is programmed to actuate the sample pump to propel sample through the reaction chamber 133 at a predetermined rate for a precise duration.

When serum or other liquid enter the liquid-filled bubble trap 130, from channel 160, entrapped or dissolved gases rise by buoyancy to the "upper" region of the trap. They are prevented from entering channel 162 as channel 161 is filled with liquid held in place by microfluidic capillary burst valve 138A. The liquid entering the bubble trap 130 exits via channel 164. Thus gas bubbles having greater buoyancy rise and the liquid continues free of detrimental bubbles.

Preferably, as shown, the liquid inlet 160 and outlet 164 of the bubble trap are located in alignment at opposite ends of a trough 160A extending across the bottom of the buoyancy chamber 130. In this relationship, laminar flow can be maintained with little influence by the nature of the liquids immediately above. Hence a succession of different liquids can flow through the chamber with little cross-contamination. In other designs however, the bubble removal system may comprise multiple bubble chambers through which respectively different liquids of the assay may flow.

The bubble trap 130 of FIG. 10 has a dividing rib 130D located in the middle of the chamber, beginning at the high side of trough 160A. Viewed in operating position, rib 130D extends upwardly a substantial distance, ending short of the upper end of the trap volume. Its outer edge 130E lies at the plane of face wall FW, to be adhered and sealed to the overlying adhesive sheet 8.

Dividing rib 130D thus forms two successive bubble capture zones 130F and 130G which are open to flow in trough 160A. These zones communicate at their upper ends. This provides a fail-safe feature. In absence of the rib, should a gross air bubble enter from inlet 160, so large that it spans the full width of the bubble trap, the gross bubble could become lodged and prevent proper liquid filling of the trap volume. In the presence of dividing rib 130D, such a gross bubble instead would be captured in the initial (upstream) capture zone 130F, leaving downstream zone 130G open to receive liquid and continue filling of the trap. Thus, the upper region of zone 130F may be filled despite lodging of a blocking bubble in lower portions of that zone. In other embodiments, not shown, the trap could be configured with one or more additional ribs that form a succession of three or more such regions to provide further fail-safe protection.

In other embodiments two or more independent bubble traps, in series, may be provided to provide a series of bubble capture zones for a given liquid flow.

FIG. 10A provides an alternate bubble trap design. Venting is by a porous plug 9A inserted at the top of the bubble trap, offering an air escape route which becomes blocked when the trap cavity 130 is filled with liquid.

Vents

In order for fluid to both enter and exit the device in an efficient manner, cassette 50 includes vent port 140, which is a closeable air vent. Vent port 140 is preferably a conduit, of cylindrical shape, for the passage of air. Vent port 140 can be filled with an air-porous material to form vent plug 9.

Vent plug 9 (or the vent plug 9A provided for the bubble trap, is of porous material permeable to gases but permanently obstructed following contact with a liquid. When used in a vent passage, while dry, it ensures an escape route for air and other gases contained in the cassette 50 or separating from liquids. It also ensures that the cassette 50 is at atmospheric pressure when liquid sample is being collected and injected into the device, and, by sealing when contacted with liquid, it ensures that cassette 50 is sealed from atmospheric contact after air has been removed from the device.

Suitable materials for use as a vent plug include a thermoplastic material, polyethylene, polypropylene, polytetrafluoroethylene (PTFE; e.g., GORE-TEX®, W.L. Gore & Associates, Inc., Newark Del.), e.g., porous plastic (e.g., porous plastic marketed by M.A. Industries (Peachtree City, Ga.), and thermoplastics, e.g., supplied by Trexel, Inc. (Woburn, Mass.), or POREX® (Porex Technologies Corporation, Fairburn, Ga.). Although porous when dry, such materials are designed to become fully closed when wet. (See, U.S. Pat. No. 5,916,814, issued Jun. 29, 1999, hereby incorporated by reference in entirety). Alternatively, vent plug 9 can be replaced with a membrane with similar properties such as is available from the W.L. Gore and Associates, Inc. (Newark, Del.).

When the vent port 140 is dry, the porous region permits air to traverse, so as to permit any gas to escape the cassette. When the vent plug 9 is wet, it is closed, and neither gasses nor liquids can escape the device. In the illustrative embodiment depicted in FIGS. 6 and 7, the vent plug 9 can absorb 1 to 5 ml of liquid, depending upon the dimensions and size of the plug.

Vent plug 9 is located such that, when the cassette is in a substantially vertical position, buoyancy causes air to reach the vent port 140 ahead of the liquid front. Preferably, vent port 140 is proximal to, or connected to, waste receptacle 139.

In some situations, such as during storage, when it is desirable to prevent vapor transfer, the outside of vent port 140 can be further sealed with a tape (not shown). Optionally, the tape can form part of a labeling system, that can then be detached and relocated for identifying the source of the analyte sample. (See, U.S. Pat. No. 4,884,827, issued Dec. 5, 1989, hereby incorporated by reference in entirety.)

Waste System

FIGS. 6 and 7 show waste receiving cavities 139 A and 139B connected together via a passage in the back of the base 13 closed with panel 14. This construction is desirable for molded manufacturing. In operating position, the waste cavities are located at the highest end of the cassette to receive all gasses and liquid that pass through reaction chamber 133. The waste cavities are constructed and located such that liquids having entered, shall not readily return to reaction chamber 133. The system incorporates air vent 140 and filter plug 9.

Liquid Channels

Channels have flow cross-section typically, between about 0.1 mm² and 1 mm² and have smooth surfaces to avoid bubble nucleation. On three sides they are formed by molded surface of body 13. They are closed on the fourth side by the overlying adhesive sheet 8. Some channels may be treated to have hydrophilic or hydrophobic properties or be treated to alter these. The channels of the preferred embodiment have a flow cross-section of 0.25 mm².

Valves

Active Valves

Figure 13:
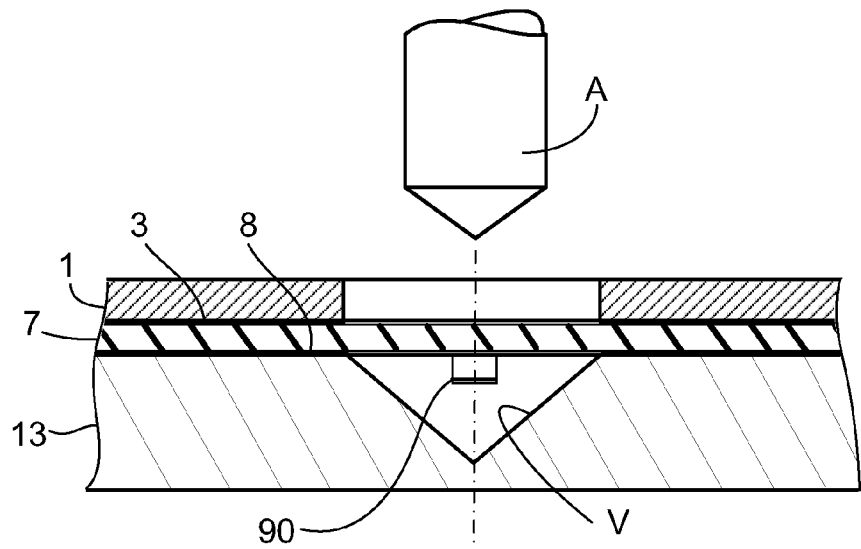
Figure 13A:
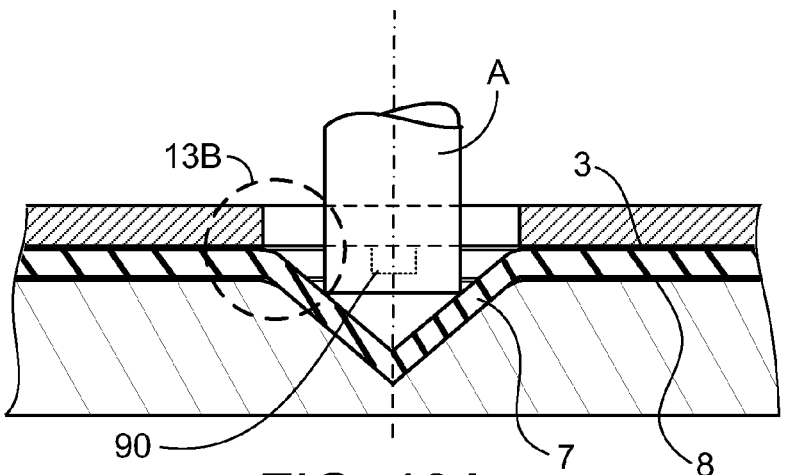
Figure 13B:
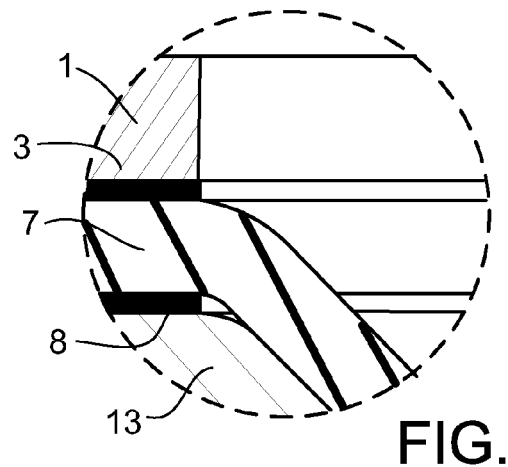
FIG. 13B is a magnified view of a region where slight leakage may occur and FIG. 13C illustrates a combination that can overcome leakage if the leakage is sufficient to be detrimental.
Figure 13C:
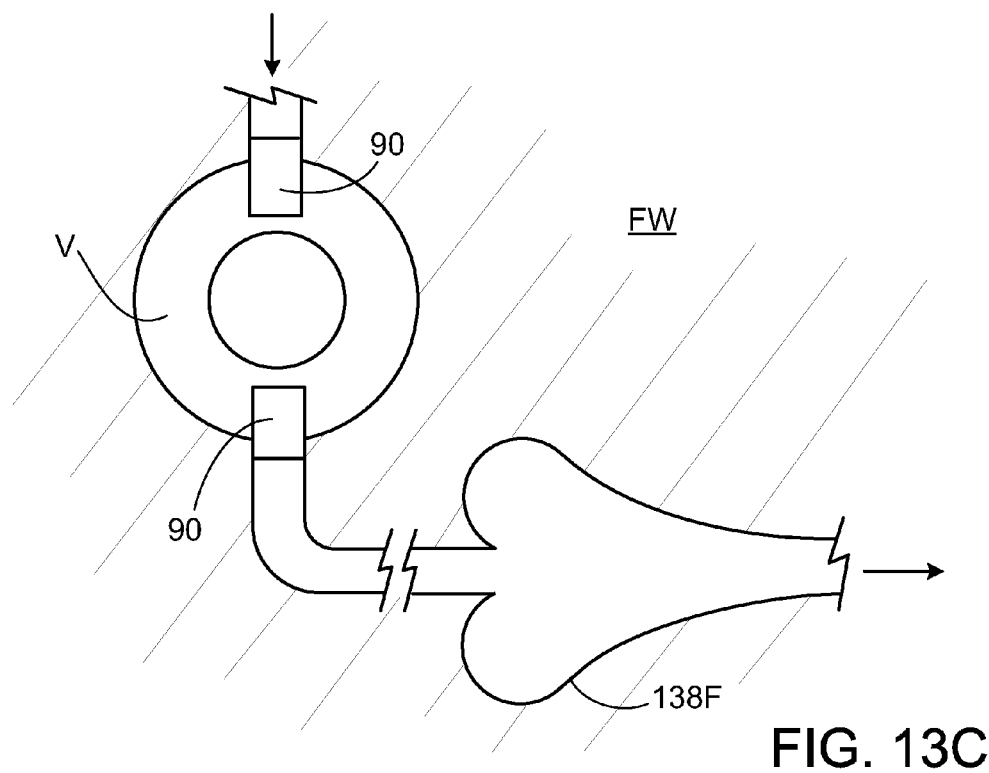

FIGS. 13-13C illustrate the operation of an active valve. The valve stem A as well as the valve seat V are of circular design in planes perpendicular to the axis shown. Flow channels 90 are open at opposite sides of the conical valve seat. During the open condition of FIG. 13, the channels 90 are open to through-flow. When the valve stem A is moved forward by a valve actuator of the control unit 60, as shown in FIG. 13A, stem A deforms the elastic membrane 7 and blocks the channels. Referring to FIG. 13B, it should be noted that the opening in the double sided adhesive sheet 8 should be sufficiently greater than the base diameter of the valve seat in order to permit the elastic membrane to minimize wicking via the circular gap and present a sufficient pressure drop so that flow can be stopped by the microfluidic capillary burst valve further along in the same channel such as microfluidic capillary burst valve 138F, see FIG. 13C.

Valve stem A is an integral element of control unit 60 and may have various forms depending on space considerations. In one case a 2 mm diameter axial extension of a linear actuator acts directly as the valve stem. In another case, the stem is of hammer shape of 90 degree included angle with a shaft diameter approximately 2 mm, actuated by a linear actuator in a lever action.

Microfluidic Capillary Burst Valves; Passive Microfluidic Valves

Figure 9:
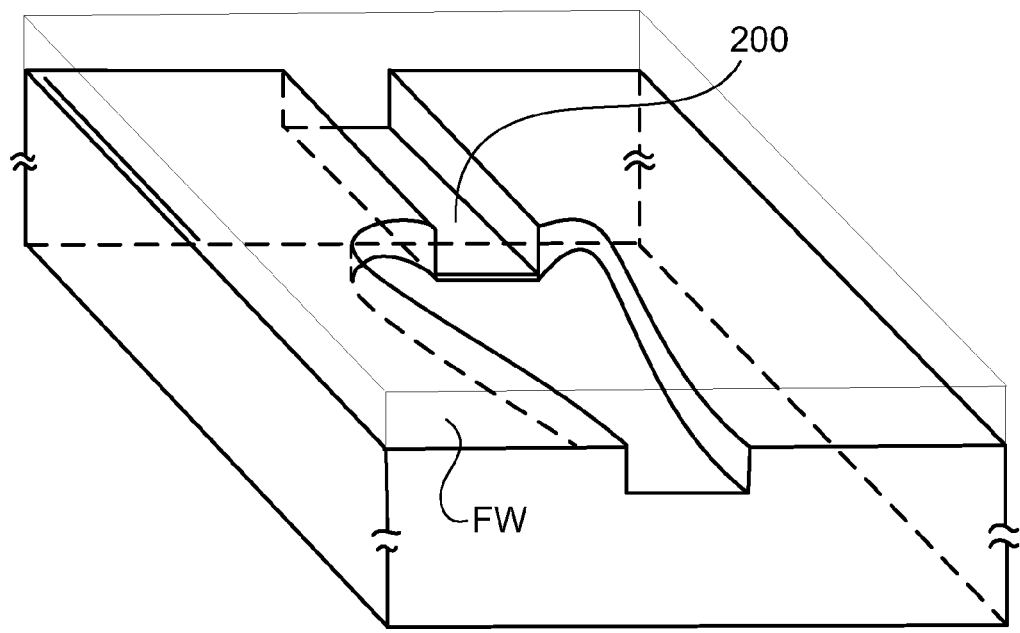
FIG. 9 is a schematic illustration of a passive microfluidic capillary burst valve.

FIG. 9 illustrates the basic design, with cover indicated by lightened lines, of a microfluidic capillary burst valve incorporated within the cassette. As with the channels, it is formed on three sides by molded surfaces of body 13, and, on the fourth side, by adhesive sheet 8.

Basic theoretical holding pressure P of a against an air chamber of a passive microfluidic valve—defined as a cylindrical or square capillary duct terminated normally in a flat plane—in the model used by J. Zeng and al.—"Fluidic Capacitance Model of Capillary-Driven Stop Valves; 5th Microfluidics Symposium IMECE Nov. 5-10, 2000 Orlando Fla.; MEMS-18A—is calculated as:

$$P = 4\gamma \sin \theta / (d)^{1.14}$$

where $\gamma$ is the surface tension of the fluid—approximately 0.070 N/m for water at 37 deg. C., about twice that of most common carbon based fluids—and $\theta$ is the contact angle, typically 45 degree at bursting point, and d the dimension of the side of a square duct of the opening.

When d=0.1 mm, P=1.4, E3 N/m2 (Pa)=0.21 psi=5.7 in $H_2O$=14 cm $H_2O$ Here, (referring to FIGS. 6 and 10) the relevant point is the necessity that valves 138C and 138D have a higher bursting capacity than valve 138A in order to ensure that the bubble trap 130 will fill with liquid while permitting the air to escape via valve 138A. To that effect, valve 138C and 138D have a smaller section than valve 138A.

FIG. 9 is a schematic illustration of a passive one way micro-fluidic burst valve, representative of valves 138 A, B, C, D and E. The dimensions of neck 200 and the exit angle define the holding forces holding the fluid against the air interface. Those knowledgeable in the art (see Inhibition and Flow of wetting liquids in Non circular Capillaries—J of Physical Chemistry B Vol. 101, pp 855-8630) define these dimensions so that air can pass through the bubble trap and the reaction chamber to void in the atmosphere via the vent filter.

Opto-sensor

FIG. 14 shows an opto-sensor for sensing the arrival of a liquid-air interface in a channel. The opto-sensor is constructed from a light source-sensor/phototransistor unit S such as, e.g., a "Reflective Object Sensor" (Type OPB606A OPTEK, Carrollton Tex.) and installed as recommended. The opto-sensors 150 and 152 (FIG. 6) optically monitor the channel, where liquid containing either analyte or buffer is to pass, through clear windows 6A and 6B, such as that cut from a common microscope slide cover (ERIE Scientific). These are installed over a liquid channel formed in the face wall FW of the cassette body 13. Light emitted by the LED element of the opto-sensor is returned to the phototransistor of the unit via mirrors 11A and 11B respectively imbedded and hermetically sealed (at I) within the rigid element of the base 13.

As both the liquids and air are present in very small volumes in the optical path of the opto-sensor, both are nearly equally transparent to the wavelength of the LED, and discrimination via absorption is unreliable. The absorption difference between air and water in a channel of less that 100 micron thick is extremely small, and peaks at only 0.5% of that of air alone when viewed in the near IR, at 950 nm, the wavelength of the OPB606A OPTEK unit.

The novelty is in sensing the interface (or "liquid front") between gas and liquid as analyte or buffer liquid displaces air. The index of refraction of air is approximately 1.000 and of water 1.332, a significant difference, such that the presence of a liquid front diffracts and deflects the incident light, from the LED, in the fashion of a prism or a lens. This interface (front) is found easy to detect as it causes a fraction of the light to be deflected away from its normal path. As the front passes in the field of view of the opto-sensor, it causes a large momentary change in signal which is easy to monitor and interpret.

Information Tracking

The sample collection device can be equipped with an optional means of recording or displaying information about the sample, such as a bar code or a surface area suitable for writing or applying markings. The recorded or displayed information can be any information desired for performing or tracking the sample and/or the diagnostic assay for which the sample is intended. In another option, additional identification tags or bar coded labels can be provided with the cassette for recording corresponding information; the second tags or labels can then be removed from the cassette to be, e.g., attached to a patient record or to an animal's cage, or to be included with the diagnostic assay, as desired. By way of example, double labels, each having identification and serialized numbers or codes, are affixed to the sample collection device, so that one is permanently attached to the sample collection device, and the other is removable and capable of being subsequently attached or bonded elsewhere, as described above, or scanned or otherwise recorded in another informational storage medium. The cassette 50 preferably has a bar code label located on the cover such as to be readable with a commercial barcode reader 69 within receiving cavity 66 of the control unit 60.

Reader (to Read Optical Signals from Array)

Reading the result of an assay consists in measuring the level of fluorescence of the level/number of fluorescent tags that have bound to the capture surface, e.g. to detecting ligand (e.g. antibody) molecules that themselves have attached to the analyte molecules that themselves have attached to the ligand receptors (e.g. capture protein molecules).

Figure 18:
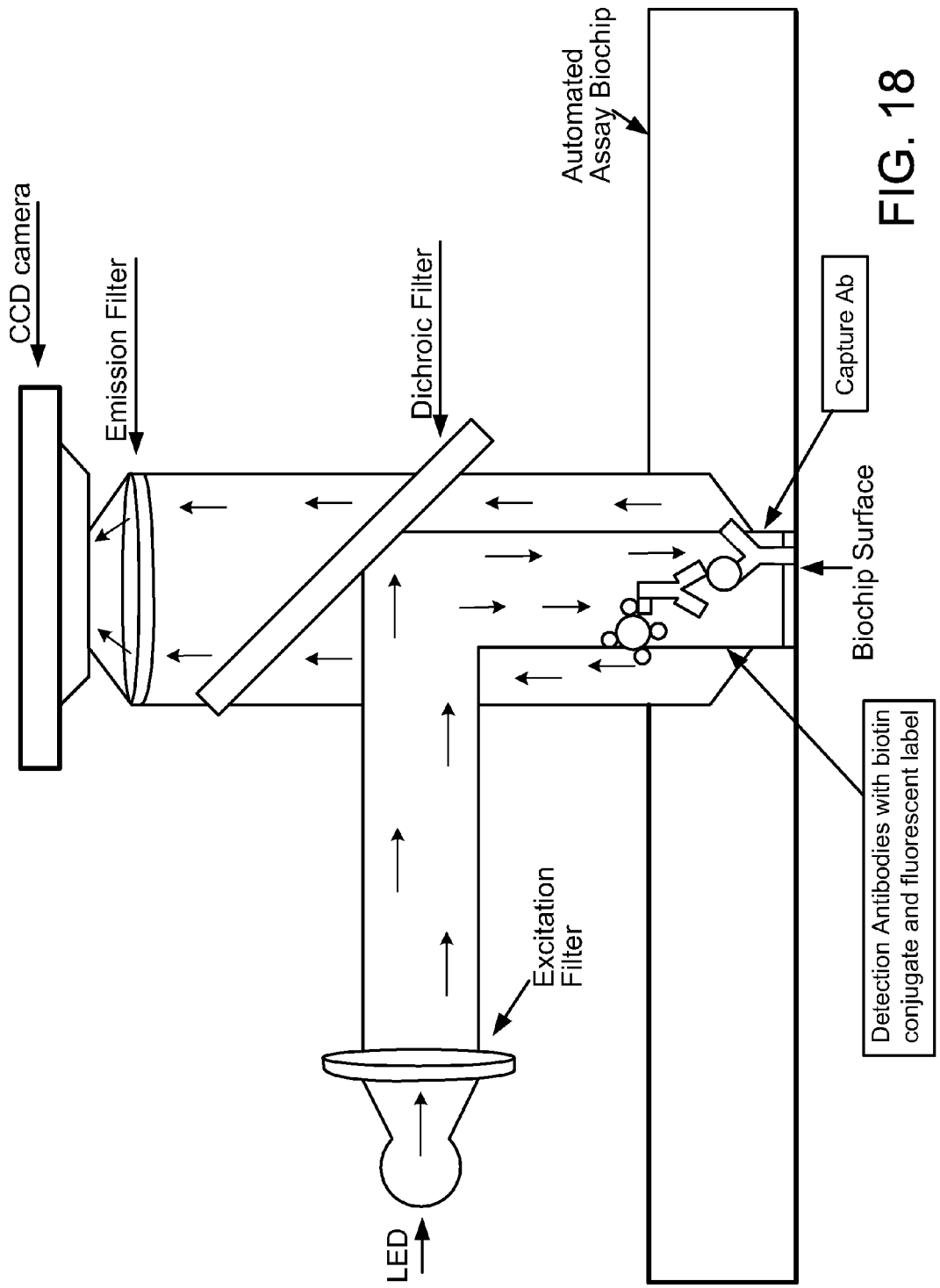
FIG. 18 illustrates the reading of the results of the assay when fluorescent tags are employed.

The level of fluorescence is represented by an aggregate of the signal level of the image pixels from the region of the image captured of the reaction chamber. Each region of interest is associated with the area and location where a specific assay has taken place. The processing instrument (system controller) 60 may have an integral reading station that captures an image of the entire biochip 20 for analysis. Alternatively a reading station separated from the processing station may be preferred. Reader station 60 has a reading system 64 that captures an image of the reaction chamber for further processing, see FIGS. 8E and F and FIG. 18.

System Controller

Algorithm for Controlling Steps of Operation

All operations are initiated by logic and implemented by the System Controller Unit. Manual operations are indicated as such. The sequence of operations for the cassette of FIGS. 6 and 7 and system controller 60 used in an immunoassay is as follows:

1) Install the cassette containing the biochip in the fluidics station 66—a manual operation
2) Inject serum into diaphragm pump reservoir 134—a manual operation
3) Close the label valve 137A—note that all valves are normally open
4) Close the wash valve 137B
5) Expel the air in the Abd chamber 131 by operating liquid pump 37 to rupture blister pouch 12 in chamber 135 and fill chamber 131 with buffer liquid (contents of blister pack 12); the Abd opto-sensor triggers 150 timing and end of flow
6) Close the Abd valve 137C
7) Open the label valve 137A
8) Operate the liquid pump 37 for a predetermined duration to expel the air in the label chamber 142 by filling it with buffer liquid.
    a) Employ a predetermined interval (or if a label opto-sensor is provided, use it to trigger timing and end of flow)
9) Close the label valve 137A
10) Prime the bubble trap with serum:
11) —run the stepper motor of the serum pump 30,
12) —the serum opto-sensor triggers 152 timing at end of filling the bubble chamber 130
13) Flow the serum through the reaction chamber 133:
14) —run the serum pump 30 stepper motor for a predetermined duration
15) Liquefy the Abd with buffer liquid
16) —run the pump 37 three steps forward and three steps back in oscillating manner; the cover membrane of chamber 131 elastically deforms. This function may be performed simultaneously with the serum flow function.
17) Open the Abd valve 137C
18) Flow the liquefied Abd through the reaction chamber by pushing it through with buffer liquid, operating pump 37
19) —run the pump 37 for a predetermined duration
20) Close the Abd valve 137C
21) Open the label valve 137A
22) Flow the label through the reaction chamber:
23) —run the pump 37 for a pre-determined duration.
24) Close the label valve 137A
25) Open the wash valve 137B
26) Flow wash liquid through the reaction chamber:
27) —run the pump 37 for a pre-determined duration.
28) Drain the reaction chamber by operating the pump 37 in reverse direction for a pre-established duration
29) The disposable cassette may then be removed from the processing station and the reaction chamber imaged for analysis at a later time. Alternately reading module of control unit 60 in the processing station may be employed.
30) The cassette with biochip may than be discarded.

Alternative Algorithm

31) Alternatively the wash step can be processed through the antibody reservoir 131:
32) Close the wash valve 137B
33) Open the Abd valve
34) Flow wash liquid through the reaction chamber via the Abd reservoir:
35) —run the pump 37 stepper motor for a pre-determined number of steps In an alternative operation mode, buffer liquid may be used to prime the bubble trap and passive micro-fluidic valve 138E blocks it from entering the sample circuit.

Analysis of Data

General

As is well known, the goal of an assay is to determine the number of molecules of interest present in a certain volume of the analyte in question: the molecular density. In immunoassays based on fluorescence this is achieved by attaching a fluorescent tag to the complexed pairs and measuring the light intensity of a defined region where the tags have attached. This results in a voltage level, a number, that must be correlated to molecular density of the molecule of interest within the sample.

When a spotted array is employed in a biochip, the information comes as a voltage level at a number of replicate spots. An operation is performed on those values to determine a representative value. For instance the highest and lowest detected value of the set may be discarded. To establish a representative value, an average or mean value may be calculated from the remaining values of the set, this value taken to be the representative value of the set of spots.

The Variables

Protein-protein interactions (or other ligand-ligand receptor interactions) are equilibrium reactions in a fluid environment where the complexing (coupling or association) of two molecules (designed or selected for highly specific associative properties) is a function of the density of each molecule in the fluid. The equilibrium condition of each pair of molecules is defined by their coupling coefficient. Historically, complexing has been defined in a stationary and fixed volume of fluid. It has been determined that the rate of complexing is strongly determined by the ability of molecules to find each other.

One class of molecule, the capture molecule (ligand receptor), is normally bound to a solid surface, to a well of a multi well plate or the support of a spotted array—in the cassette described above the support is glass coated with Activated Nitrocellulose. The other molecule (the ligand) present in the analyte, is introduced in liquid.

Using an ELISA multi-well plate for the assay, mixing for molecular association is by diffusion and very slow because the molecular distances of travel (6 mm well diameter) are large and no mechanical mixing takes place. Control of the critical parameters is poor. Fluid diffusivity is a strong function of the viscosity, temperature, and molecular weight (protein size) of the molecules.

In a flow microchannel, molecular association is faster and affected by the same variables and to a small degree by flow rate. Flow conditions are also different as molecular density at the coupling sites changes with time and flow rate.

At very low Reynolds Number (extremely slow) liquid flow over a spotted array, molecular association is also dominated by diffusion but the diffusion travel distances are very small and the reaction time accordingly shorter.

The complexing rate for a given set of parameters is not linear and reaches equilibrium in an asymptotic manner as indicated in FIG. 3A, discussed above.

In an equilibrium assay, after a period of time, equilibrium is reached where the rate of association between the analyte and capture molecules is equal to the rate of disassociation between those molecules. This takes a great amount of time: in a multi-well plate, a substantial fraction of an hour for very high molecular density and over night for low molecular densities.

It is common to terminate an assay without reaching a state of equilibrium because of the long duration required to achieve the equilibrium.

The variables when employing spotted arrays are numerous even after the operator's idiosyncrasies have been eliminated by use of a machine and the controlled environment of a cassette:
- the quality & quantity of molecules of interest and their affinity constant
- the reaction temperature
- atmospheric pressure
- humidity
- the geometry of the reaction chamber
- the spot size
- the density of capture molecule on each spot
- the properties of the support surface, e.g. the nitrocellulose coating
- the flow rate and distribution
- the duration of the assay
- the sensitivity of the "Reader"
- the tolerances of the processing system Calibration and Control Due to the large number of variables it has been common for a correlation constant—a curve—to be pre-established. At the time of an assay performance of the reading System is verified, (referred to as "Control") and the biology and chip are verified, referred to as "Calibration":

1. For each manufacturing run of a specific bio-chip it has been common to establish a set of Standard Curves using some of the biochips of the run and the process and protocol of the assay. This correlates signal level and concentration for each molecule of interest under standard conditions. This is done (typically by the manufacturer) by running a set of known concentration samples through identical chips all constructed in the one manufacturing run. A minimum of 6 different concentrations (and a corresponding number of chips) has been required to define such a curve. When a new run of chips is manufactured, it has been necessary to create a new set of Standard Curves, with further consumption of chips.

2. "Control": This is to ascertain that the reading instrumentation is working correctly. This is done with the use of "control spots." The control spots are printed on all bio-chips and are expected to give a pre-determined signal. The spots may be loaded with Cy3 dye, bound protein or inert reference material such as Kapton. The control spots are deposited at the same time that all assay spots are deposited. Typically only one row is needed. One must keep in mind that there are numerous things that can go wrong and that the number obtained is always tainted with a CV percentage.

3. "Calibration": This has been performed by the user before an assay is performed with chips from a given manufacturing lot. Typically 2 chips of the lot are run (expended) against known dilutions to verify or adjust the overall system performance against the Standard Curves established by the manufacturer for that lot.

An aspect of invention will now be described.

Self-Calibrating Bio-Chip

As mentioned, according to common procedures, a number of identical chips from a run have been considered in an identical environment to develop Standard Calibration curves for the remaining chips.

In contrast, according to FIG. 16, an extensive set of calibration spots and control spots are printed on each chip in addition to the ligand receptor. The concept is to spot known dilutions sufficient in number and dilution levels to effectively establish a calibration curve following passage of the detection reagents, e.g. antibodies and tag liquids, over the chip. Each chip is thus made to be self calibrating.

For example, the chip of an assay designed to evaluate the presence of specific protein in the analyte is spotted in a conventional manner with a row of the capture antibody (ligand receptor) specific to the protein of interest. According to FIG. 16, the array is also spotted down stream with rows of spots of the very protein under evaluation in sufficient number of different dilutions, six as shown, to effectively establish a calibration curve. These spots are referred to here as Intrinsic Calibration Spots—ICSs. (In FIG. 16 the ligand receptor spots are depicted as larger than the reference and control spots, to signify their biological difference. In practice all spots may be the same size.)

Referring to FIG. 16, calibration rows 1A through 1G comprise analyte ligand specific to the spots of the receptor for analyte 1; calibration rows 2A through 2G comprise spots of the ligand specific to the spots of the receptor for analyte 2, and so on. In this example, all spots of each given row of the set of rows 1A through 1G are of the same dilution, this dilution being different from spots of the other calibration rows.

For this system to be effective, the detection reagents, e.g. antibodies and tags, are presented in sufficient abundance in flow over the array to bind to practically all protein (ligand) of interest present at the capture antibodies (ligand receptors) as well as at all the sites on the ICSs. Calibration curves specific to an individual chip may thus be derived as part of the reading process for that chip.

The rows of ICSs are located to minimize competitive molecular attraction between rows as well as local molecular depletion. This can be determined experimentally. In many cases, preferably the spots with highest dilution are located closest to the flow intake, followed by the next highest dilution, and so on. Successive rows may be offset from the travel path of the preceding row as shown in FIG. 16 and some rows may be separated extra distances, to facilitate homogenization of the flow before reaching the next ICS row.

With software, the signal derived from the spots with the molecules of interest within the analyte can then be compared to the signal derived from the ICS. (Interpolation between measured values makes the process equivalent to comparison to a calibration curve.) The molecular density in the analyte can thus be determined by reference to information derived from the bio-chip itself. Such self-calibrating bio-chips may be employed in the cassettes described.

Other Bio-chip Formats

Biochips having the format of FIG. 16A may likewise be employed. In this case pre-established calibration data is employed by the instrument to calibrate the readings. Control deposits on the biochip enable verification of operation of the system, or adjustment of its sensitivity based upon the detected value of the known fluorescent value of the control deposits.

Biochips having the format of FIG. 16B may likewise be employed with pre-established calibration curve data employed by the instrument to calibrate the readings. In the embodiment of FIG. 16B, each analyte is accompanied by two reference deposits of ligand A and B at different predetermined dilutions. These are employed, in reference to the predetermined calibration curve for the respective manufacturing lot, to adjust the detected results to the calibration curve.

In Conclusion

While much of the detailed discussion has related to a particular example of an immunoassay, it will be understood that techniques described are applicable to the general class of assays employing ligand receptors attached to a solid substrate and ligands in the liquid flowing over it.

What is claimed is:

1. An assay cassette comprising: a capture surface having a generally planar bottom within a tunnel that carries an array of spaced-apart regions of ligand receptors, and a liquid passage system constructed with a widening flow transition section to direct over the array a sheet flow of liquids having Reynolds numbers less than about 1, the liquids including a ligand-containing liquid, each ligand receptor forming a round spot extending upwardly from the capture surface up in the tunnel, the round spot forming a capture area for capturing a ligand, the liquid passage system including a gas bubble removal system to which the liquids are exposed, the gas bubble removal system constructed and arranged to remove gas micro-bubbles from the liquids prior to exposure of the liquids to the array and the assay cassette having a generally planar extent with an upper end and lower end, the capture surface extending upwardly in the direction of liquid flow toward the upper end of the cassette, and a waste outlet extending from an upper end of the capture surface toward the lower end of the cassette for removing waste from the capture surface by gravity.

2. The assay cassette of claim 1 further comprising heat transfer surfaces to which flows of the liquids are exposed for heating the liquids prior to exposure of the liquids to the gas bubble removal system, whereby gas micro-bubbles produced in the liquid by heat delivered via the heat transfer surfaces of the cassette can be removed before the liquids are exposed to the array.

3. The assay cassette of claim 2 configured to receive heat from a heater of an external device, the cassette constructed and arranged to enable heat to flow through substance of the cassette to the heat transfer surfaces, thence to the liquid.

4. The assay cassette of claim 1 further comprising a site for storage of an agent useful in the assay, the cassette constructed to enable combining a liquid with the agent to produce an assay-supporting liquid, and, respectively, to enable flow of the assay-supporting liquid through the liquid passage system, or through the liquid passage system with exposure to a heat transfer surface, the cassette constructed to enable exposure of the assay-supporting liquid to the gas bubble removal system prior to reaching the array, whereby gas micro-bubbles previously produced in the assay supporting liquid can be removed before the assay-supporting liquid is directed over the array.

5. The assay cassette of claim 4 in which the agent is the ligand or a substance comprising a detectable tag.

6. The assay cassette of claim 4 in which the agent, prior to combining, is stored in dry state in a chamber of the cassette, with the agent exposed to air, the cassette constructed to enable introduction of the liquid to the chamber in combining action, and the gas bubble removal system is effective to remove micro-bubbles of the air produced by the combining action.

7. The assay cassette of claim 6 in which the chamber of the cassette has an elastically distensible wall portion adapted to elastically expand in response to the liquid displaced into the chamber, and to elastically contract when the liquid flows out of the chamber.

8. The assay cassette of claim 1 further comprising at least one liquid storage chamber, the liquid storage chamber associated with a displacement pump constructed to displace liquid in continuous flow from the storage chamber, respectively, to flow through the passage system or through the passage system with exposure to a heat transfer surface, the cassette constructed to enable exposure of the liquid to the gas bubble removal system prior to reaching the array, whereby gas micro-bubbles previously produced in the liquid can be removed before the liquid is directed in continuous flow over the array.

9. The assay cassette of claim 8 in which the displacement pump comprises an elastic diaphragm forming a wall portion of the liquid storage chamber and operable by an external, continuously movable actuator to produce the continuous flow.

10. The assay cassette of claim 9 in which an outlet to the passage system is located at the top of the liquid storage chamber exposed to air present in the liquid storage chamber, the cassette and diaphragm constructed and arranged to expel air from the liquid storage chamber followed by forcing liquid through the passage system in continuous flow via the gas bubble removal system and over the array.

11. The assay cassette of claim 8 in which the liquid storage chamber is constructed to contain a sealed pouch containing the liquid for the assay, the chamber associated with a device for puncturing the pouch to release the liquid.

12. The assay cassette of claim 8 in which the liquid storage chamber is constructed to receive and store a liquid introduced to the cassette from the exterior, whereby gas microbubbles produced in the liquid by the step of introduction of the liquid to the cassette can be removed by the gas bubble removal system before the liquid flows over the array.

13. The assay cassette of claim 12 in which the liquid storage chamber is constructed to receive the liquid from the exterior via a needle or pipette projected through a septum, the septum comprising an elastomeric mass that has a pierced passage, the elastomeric mass mounted under substantial compression relative to the pierced passage, the compression effective to maintain the pierced passage closed but enabling insertion and removal of a plastic liquid-supply needle or pipette through the pierced passage.

14. The assay cassette of claim 8 further comprising at least one waste chamber to which the liquid flows after being pumped in continuous flow by the displacement pump, exposed to the gas bubble removal system and directed over the array, whereby the liquid is contained within the cassette throughout the assay.

15. The assay cassette of claim 14 constructed and arranged so that during performance of the assay the capture surface and the liquid flow over it have an upward extent, and the waste chamber is positioned in the cassette to receive gravity flow of liquid from the waste outlet.

16. The assay cassette of claim 1 in which the liquid passage system includes at least one actuatable valve through which liquid flows prior to being exposed to the gas bubble removal system, whereby gas micro-bubbles produced in the liquid by passage through the valve can be removed before the liquid is directed over the array.

17. The assay cassette of claim 16 in which the valve comprises a valve seat across which liquid flows, the valve seat defining inlet and outlet passages, and an elastic diaphragm extends over the valve seat and is displaceable to engage the valve seat to interrupt the flow.

18. The assay cassette of claim 17 in which the valve is a stop valve followed by a surface-tension burst valve, the burst valve being capable of blocking migrating liquid that may leak past the stop valve when the valve is closed, but, at flow pressure, capable of transmitting liquid to flow over the array.

19. The assay cassette of claim 1 in which the liquid passage system is constructed and arranged to enable more than one flow of liquid of Reynolds number less than about 1 over the array after exposure of the liquids to the gas bubble removal system.

20. The assay cassette of claim 19 constructed to perform a sandwich assay in which liquid flows of the assay are exposed to the bubble removal system, the cassette comprising storage sites for liquid sample and all substances employed in the sandwich assay, the cassette having at least one waste chamber, the cassette being constructed and arranged to contain all liquids disposed therein throughout the performance of the sandwich assay.

21. The assay cassette of claim 20 wherein the array is two-dimensional and the spots have a diameter between about 50 μm and 500 μm.

22. The assay cassette of claim 21 in which the capture surface exposed to the liquid flow has dimensions of at least about 0.5 cm in the direction of the flow and in the direction transverse to the direction of flow.

23. The assay device of claim 21 in which the cross-section area of flow preceding the flow transition section is about 0.25 mm$^2$ or less and the cross-section area of the flow over the capture surface is at least 0.75 mm$^2$.

24. The assay cassette of claim 21 in which the capture surface carries at least 3 replicate regions of each of a multiplicity of ligand receptors arrayed transversely to the direction of flow of the liquid over the capture surface.

25. The assay cassette of claim 24 in which the array on the capture surface includes, in regions in proximity to the regions of a given ligand receptor, reference regions of known quantity of the ligand to which the receptor is specific.

26. The assay cassette of claim 1 in which the bubble removal system comprises at least one buoyancy chamber to which the liquid is exposed.

27. The assay cassette of claim 26 having a generally planar extent and constructed to be disposed at a substantial angle to the horizontal during performance of the assay to dispose the buoyancy chamber above a discharge outlet through which the liquid is directed to the capture surface.

28. The assay cassette of claim 27 in which the angle to the horizontal locates the capture surface above the flow transition section that receives liquid from the buoyancy chamber and spreads the liquid flow to a width corresponding with the width of the capture surface, the flow transition section constructed to direct the liquid in continuous upward flow over the capture surface.

29. The assay cassette of claim 28 further comprising a liquid storage chamber having an outlet passage, the angle to the horizontal locating the storage chamber below the capture surface, the storage chamber associated with an externally actuatable displacement pump that is effective to force liquid from the storage chamber in continuous flow through the buoyancy chamber and upwardly over the capture surface to the waste outlet.

30. The assay cassette of claim 26 in which, in operating orientation, the buoyancy chamber has a top and bottom, a liquid inlet and a liquid outlet, both the liquid inlet and outlet being located near the bottom, in flow-aligned relationship.

31. The assay cassette of claim 26 constructed to enable initial filling of the buoyancy chamber by a liquid stored in the cassette, and to have the liquids of the cassette flow through the buoyancy chamber in sequence, in laminar flow between the inlet and the outlet of the buoyancy chamber.

32. The assay cassette of claim 26 in which the buoyancy chamber comprises a depression molded in a face of a plastic body and channels molded in the face of the plastic body for liquid leading to and from the depression, and an adhesive sheet overlies the molded depression and the channels and is adhered to face portions of the molded body bounding the depression and the channels.

33. The assay cassette of claim 1 in which the bubble removal system, for a given flow, includes, in succession, at least two bubble capture zones to which the flow is exposed.

34. The assay cassette of claim 33 in which the bubble capture zones are constructed and arranged to enable bubbles to rise into the bubble capture zones by buoyancy effects.

35. The assay cassette of claim 34 comprising a buoyancy chamber constructed for liquid flow from an inlet, along a path exposed to enable bubbles to rise by buoyancy effects for capture, to an outlet, there being at least one divider wall spaced along and above the liquid path to define upstream and downstream bubble capture zones exposed to the path such that a large bubble in liquid flow at the inlet will tend to be trapped in the upstream capture zone, leaving the downstream capture zone free to receive liquid flow.

36. The assay cassette of claim 35 in which the divider wall terminates in an upward region above which liquid entering the downstream zone can fill the upstream zone above any bubble lodged in a lower portion of the upstream zone.

37. The assay cassette of claim 35 in which the buoyancy chamber comprises a depression molded in a plastic body, there being a molded upstanding rib defining the divider wall, and an adhesive sheet overlies the molded depression and is adhered to face portions of the molded body bounding the depression, and adhered to an outer edge of the molded rib.

38. The assay cassette of claim 3 having a molded body, the body defining at least one molded receptacle of depth suitable to hold an assay liquid and a molded face wall, the molded receptacle being open at a face-side plane and the molded face wall having an outer face generally aligned with the face-side plane, the outer face of the face wall having at least one molded channel forming a liquid passage for directing liquid from the molded receptacle to an assay region of the cassette, the face wall having a thickness substantially less than the depth of the molded receptacle and having a back surface at a heater cavity that is open from the backside of the body, the heater cavity constructed and arranged to removably receive the external heater to engage portions of the back surface of the face wall in surface-to-surface heat-transfer contact to heat liquid flowing in the molded channel by heat conduction through the thickness of the molded face wall.

39. The assay cassette of claim 38 having a chip-receiving opening defined in the face wall to receive and position an assay chip so that the chip bounds a reaction chamber into which a molded channel of the face wall directs liquid, the heater cavity in the molded body extending below the chip-receiving opening to expose the chip for surface-to-surface heat-transfer contact with the external heater to heat liquid in the reaction chamber by heat conduction through the thickness of the assay chip.

40. The assay cassette of claim 39 constructed to enable a portion of the backside of the chip to be exposed to a temperature sensor to control the energization of the heater.

41. The assay cassette of claim 38 in which the receptacle is an analyte-receiving receptacle arranged to discharge into a molded channel of heat-exchange contour, preferably of serpentine contour, in a portion of the face wall that is arranged to receive heat from the heater.

42. The assay cassette of claim 38 in which one side of at least one liquefying chamber is molded as a depression in a portion of the face wall through which a liquid channel directs liquid, this portion of the face wall having a back surface exposed for engagement by the external heater for surface-to-surface heat transfer contact to heat liquid in the liquefying chamber by heat conduction through the thickness of the molded face wall.

43. The assay cassette of claim 38 in which one side of the bubble removal system is molded as a depression in a portion of the face wall through which a liquid channel directs liquid, this portion of the face wall having a back surface exposed for engagement by the external heater for surface-to-surface heat transfer contact to heat liquid in the bubble removal system by heat conduction through the thickness of the molded face wall, preferably this bubble removal system comprising a liquid-filled bubble trap.

44. The assay cassette of claim 38 comprising a cover assembly secured over the receptacle and face-wall of the molded body, the cover assembly including an elastic diaphragm portion lying over the receptacle, the diaphragm portion adapted to be deflected to displace liquid from the receptacle through the molded channel, preferably another portion of the face wall is molded in the form of a valve seat and the cover assembly includes a diaphragm portion adapted to be deflected to engage the valve seat to stop flow.

45. The assay cassette of claim 38 in which the molded body is of generally planar extent and bound, at least substantially, by a perimeter wall of substantially constant depth extending between respective parallel planes.

46. The assay cassette of claim 38 in which the back surface of the face wall of the molded body is planar, preferably parallel to face-side and back-side planes of the cassette, and arranged to be engaged by the external planar heat-delivering face of a heater, preferably the heater comprising a flexible, sheet-form resistance heater mounted on a resilient planar pad carried on a rigid, planar plate that is mounted in floating manner enabling the corresponding planar surfaces of the molded body and the heater to self-adjust into face-to-face heat-transfer contact.

47. The assay cassette of claim 1 having a molded body, the body including at least one molded receptacle of depth suitable to hold an assay liquid and a molded face wall, the molded receptacle being open at a face-side plane and the molded face wall having an outer face generally aligned with the face-side plane, the outer face of the face wall having at least one molded channel forming a liquid passage for directing liquid from the receptacle to an assay region of the cassette, the front surface of the face wall being planar and adhered to an adhesive side of an adhesive sheet, portions of the adhesive sheet lying over the channel in the face wall, closing the respective side of the channel.

48. The assay cassette of claim 47 in which the adhesive sheet carries adhesive on its oppositely directed sides, the adhesive sheet having at least one window corresponding to a liquid receptacle or valve seat, one adhesive side of the adhesive sheet being adhered to the face wall, the oppositely directed adhesive side adhered to an elastic diaphragm sheet, a portion of the elastic diaphragm sheet lying over the window defining a deflectable pump or valve diaphragm at the respective receptacle or valve seat in the molded body.

49. The assay cassette of claim 48 including a second adhesive sheet carrying adhesive on its oppositely directed sides, one adhesive side of the second adhesive sheet being adhered to the outer side of the diaphragm sheet and the oppositely directed adhesive side adhered to a relatively rigid cover member.

50. The assay cassette of claim 49 in which there is a window in the second adhesive sheet overlying a pump receptacle, and a breakaway portion of the cover overlying the diaphragm at the pump receptacle is constructed to break from the cover to act as pump piston head for deflecting the respective portion of the diaphragm in response to externally applied actuation force, preferably the break away portion of the cover being adhered to a corresponding outer surface portion of the diaphragm sheet.

51. The assay cassette of claim 1 constructed for use with a protocol which produces light-emitting tags associated with complexes of receptor and ligand, the cassette having a window constructed and arranged to enable reading of light emitted from the tags.

52. The assay cassette of claim 51 in which the capture surface comprises a nitrocellulose layer of less than about 1 micron thickness.

53. The assay cassette of claim 1 constructed as a disposable sandwich assay cassette for optical reading,
the cassette operable by an external apparatus, and having:
a) a liquid storage chamber and associated displacement pump for producing a continuous flow of liquid sample containing an analyte ligand,
b) at least a second liquid storage chamber and an associated displacement pump for producing continuous flows of the liquids used for completing the assay, c) a flow-through reaction chamber in which the capture surface of extended width is situated,
d) at least one waste chamber for receiving waste liquid from the waste outlet,
e) the liquid passage system including the flow transition section which spreads the liquid flow to the width of the capture surface,
f) the capture surface carrying the array, wherein the array is a two-dimensional array which includes spaced-apart replicate regions of ligand receptors, the capture surface being positioned and arranged for optical reading,
g) the liquid passage system comprising a flow network for directing flows of the sample and the assay-supporting liquids through the reaction chamber, over the capture surface,
h) a venting arrangement for air displaced by liquid forced through the system,
i) and heat transfer surfaces arranged to receive heat to bring the liquids to about a desired assaying temperature prior to entering the bubble removal system and to maintain the reaction chamber at assaying temperature,
j) the liquid displacement pumps of the storage chambers, the flow network including the associated gas bubble removal system and the flow transition section, and the reaction chamber constructed to produce relatively widened flows of Reynolds numbers less than about 1 of a sequence of liquids over the capture surface, thence to the waste chamber.

54. The assay cassette of claim 53 in which the heat transfer surfaces to which the liquids are exposed are in heat-transfer relationship to an exterior surface of the cassette, the exterior surface of the cassette adapted to be placed in heat-receiving relationship with a heater member of the external apparatus.

55. The assay cassette of claim 53 in which an agent for use in the sandwich assay is stored in dry state in an agent storage chamber of the cassette, with the agent exposed to air, the cassette having a heat transfer surface arranged to heat the agent storage chamber to about the desired assaying temperature and to enable introduction of the liquid to the agent storage chamber in combining action, the gas bubble removal system being effective to remove micro-bubbles of air produced by the heating and the combining action in the agent storage chamber.

56. The assay cassette of claim 53 in which the capture surface carries at least 3 replicate regions of each of a multiplicity of the ligand receptors arrayed transversely to the direction of flow of the liquid through the reaction chamber.

57. The assay cassette of claim 56 in which the array on the capture surface includes, in regions in proximity to the regions of a given ligand receptor, reference regions of known quantity of the ligand to which the receptor is specific.

58. The assay cassette of claim 56 in which the ligand receptor is an antibody or antigen which is specific, respectively, to an antigen or antibody ligand in the sample.

59. The assay cassette of claim 1 in which the bubble removal system, in operating orientation, comprises an upwardly extending buoyancy chamber adapted to contain liquid and having a top, a liquid inlet and a liquid outlet, the outlet located lower than the top of the buoyancy chamber in position adapted to be submerged in liquid of the buoyancy chamber, there being a vent passage from the upper portion of the buoyancy chamber.

60. The assay cassette of claim 59 in which the buoyancy chamber communicates with an air vent associated with a waste chamber of the cassette until the buoyancy chamber receives liquid, a first surface-tension burst valve being associated with a passage leading from the liquid outlet from the buoyancy chamber, the first burst valve being constructed and arranged to be effective to prevent liquid flow beyond the buoyancy chamber until the chamber is filled with liquid, and the vent passage comprises an air-porous but liquid-blocked element located in the top region of the buoyancy chamber permitting air to exhaust from the chamber but blocking passage of liquid.

61. The assay cassette of claim 59 in which the buoyancy chamber communicates with an air vent associated with a waste chamber of the cassette until the buoyancy chamber is initially filled with liquid, a first surface-tension burst valve being associated with a passage leading from the liquid outlet from the buoyancy chamber, and a second surface-tension burst valve communicating with the top of the buoyancy chamber being associated with the vent passage, the first burst valve being constructed and arranged to be effective to prevent liquid flow beyond the buoyancy chamber until the chamber is filled with liquid, and the second burst valve being constructed and arranged to be effective to prevent liquid flow from the top of the buoyancy chamber after the buoyancy chamber is filled with liquid.

62. The assay cassette of claim 26 having a temperature control region constructed to enable all liquids associated with the assay to be brought approximately to an assaying temperature, the gas bubble removal system following the temperature control region to which the liquid is exposed prior to reaching the capture surface, and comprising an upwardly extending buoyancy chamber adapted to contain liquid and having a top, a liquid inlet and a liquid outlet, the outlet located lower than the top of the buoyancy chamber in position adapted to be submerged in liquid of the buoyancy chamber, there being a vent passage from the upper portion of the buoyancy chamber.

63. The assay cassette of claim 26 in which the liquid passage system is constructed to initially fill the buoyancy chamber with liquid from a first storage volume in a manner that a further flow passage to be connected to provide flow of another liquid through the buoyancy chamber can be isolated and remain empty during the filling of the buoyancy chamber, the buoyancy chamber sized to receive and contain air displaced from the empty passage when liquid is forced through the further passage on its way to the buoyancy chamber without exposing the liquid outlet from the buoyancy chamber to air filling the top of the buoyancy chamber.

64. The assay cassette of claim 1 comprising a generally planar molded body of rectangular form of length of about 8 cm or less and width of about 5 cm or less, constructed to be oriented with its longitudinal axis disposed at a substantial angle to the horizontal during use;
l) in such orientation, substantially the lower half of the body defining, in side-by-side manner, a storage chamber for a pouch of buffer liquid, a detection ligand chamber for a detection ligand stored therein in desiccated form, and an agent chamber for a fluorescent tag agent stored therein in desiccated form;
m) a reaction chamber containing the capture surface located adjacent the opposite longitudinal end of the molded body, at least one waste chamber disposed laterally to one side of the reaction chamber, positioned to receive gravity flow of waste from the reaction chamber; and
n) a temperature control region in the form of a heated region arranged to heat liquids prior to the liquids entering the gas bubble removal system.

65. The assay cassette of claim 1 constructed to be disposed at an angle in assaying position relative to a rest position, in which a venting arrangement comprises an air vent communicating with a waste chamber, the air vent comprised of material that is permeable to air until wetted, the material located not to be wetted by liquid in the waste chamber when the cassette is in assaying position and to be wetted by liquid from the waste chamber when the cassette is placed in the rest position after use.

66. The assay cassette of claim 1 constructed to be controllable by external apparatus the liquid passage system comprising a flow network which includes at least one sensing station adapted to receive an optical sensing beam and enable the beam to pass through a flow passage and thence to a detector in the manner that the beam at the detector is altered in detectable manner by arrival of a liquid-air interface in the flow passage at the sensing station, the altered beam useful as a control signal by the external apparatus during conduct of the assay.

67. A method of conducting an assay comprising providing the assay cassette of claim 1 and external apparatus suitable to control the assay, introducing a sample to a sample chamber of the cassette, and, according to a predetermined assay protocol, conducting the assay under control by the external apparatus, including continuously flowing the sample over the capture surface at Reynolds numbers less than about 1 for a selected duration, and reading the capture surface of the cassette.

68. A method of conducting a sandwich assay comprising providing the assay cassette of claim 43 and external apparatus suitable to control the assay, wherein the array comprises replicate regions of ligand receptor specific to a ligand of an analyte molecule, introducing the liquid sample that includes the analyte molecule to the sample chamber and, according to a predetermined sandwich assay protocol suitable for optical reading, under control of the external apparatus, at Reynolds numbers less than about 1, causing, sequentially, continuous flow through the reaction chamber of the sample at a predetermined flow rate for a predetermined time, and continuous flows of the assay-supporting liquids for appropriate times, and optically reading the capture surface of the cassette.

69. The method of claim 68 wherein the ligand receptors are in the form of an antigen or antibody specific to the analyte molecule.

70. The assay cassette of claim 1 enabling self-calibration, the spots of the array comprising a set of replicate deposits of a given ligand receptor for the assay and bearing, in association with that set, a set of calibration deposits that comprises a number of groups of replicate deposits of the ligand for which the ligand receptor is specific, the groups being of respectively different known dilutions of the ligand, the known dilutions selected, when developed, to be sufficient to define a calibration curve for assay measurements made at the deposits of the given ligand receptor after their exposure to a sample containing the ligand, the groups of calibration deposits being adapted to be developed by attachment of a readable tag to all ligand on the capture surface at the deposits of ligand.

71. The assay cassette of claim 70 including at least one row of control deposits of given measurable intensity on the capture surface for verification of operation of the measuring system.

72. The assay cassette of claim 70 in which the tag is a fluorescent tag.

73. The assay cassette of claim 70 constructed for exposure of the capture surface to a sheet-form stream of sample and reagent having a direction of flow, the replicate deposits being arranged in at least one row oriented transverse to the direction of the flow, and the groups of calibration deposits being spots arranged in rows transverse to the direction of the flow.

74. The assay cassette of claim 73 in which the replicate deposits of ligand receptor are in a single row transverse to the flow, and calibration deposits of each given dilution are arranged in a single respective row transverse to the flow.

75. An assay method comprising providing an assay cassette according to claim 70, exposing the capture surface to a flow of sample containing the ligand followed by exposing the capture surface to conditions by which the readable tag becomes attached to all ligand present in the sample, reading the tag by a reader to obtain measurements of each deposit, analyzing the data from the group of calibration deposits to develop a table of calibration values, comparing a value derived from the group of ligand receptors with values from that table and deriving therefrom a value representing the concentration of the ligand in the analyte.

76. The assay method of claim 75 in which the tag is a fluorescent tag, and the reader is a fluorescence reader.

77. The method of claim 75 in which the ligand receptor is an antigen or antibody and the analyte is respectively an antibody or antigen.

* * * * *